(12) United States Patent
Winter et al.

(10) Patent No.: US 12,137,690 B2
(45) Date of Patent: *Nov. 12, 2024

(54) HERBICIDAL MIXTURES COMPRISING L-glufosinate AND THEIR USE IN COTTON CULTURES

(71) Applicant: BASF SE, Ludwigshafen (DE)

(72) Inventors: Christian Harald Winter, Ludwigshafen (DE); Markus Gewehr, Limburgerhof (DE); Ryan Louis Nielson, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/140,211

(22) Filed: Apr. 27, 2023

(65) Prior Publication Data
US 2023/0255208 A1 Aug. 17, 2023

Related U.S. Application Data

(63) Continuation of application No. 16/636,840, filed as application No. PCT/EP2018/070933 on Aug. 2, 2018, now Pat. No. 11,666,053.

(30) Foreign Application Priority Data

Aug. 9, 2017 (EP) ..................................... 17185464

(51) Int. Cl.
*A01N 57/20* (2006.01)
(52) U.S. Cl.
CPC .................................. *A01N 57/20* (2013.01)
(58) Field of Classification Search
CPC ........ A01N 57/20; A01N 35/10; A01N 35/37; A01N 35/22; A01N 41/10; A01N 43/18; A01N 43/40; A61K 2800/58
See application file for complete search history.

(56) References Cited

U.S. PATENT DOCUMENTS

| | | | |
|---|---|---|---|
| 4,265,654 | A | 5/1981 | Takematsu et al. |
| 4,830,658 | A | 5/1989 | Bieringer et al. |

(Continued)

FOREIGN PATENT DOCUMENTS

| | | |
|---|---|---|
| CN | 102027992 A | 4/2011 |
| CN | 102715186 A | 10/2012 |

(Continued)

OTHER PUBLICATIONS

"New herbicidal combinations", Hoechst AG, The Industrial Standard Disclosure Publication Service, 1987, 3 pages.

(Continued)

Primary Examiner — Trevor Love
(74) Attorney, Agent, or Firm — MARSHALL, GERSTEIN & BORUN LLP

(57) ABSTRACT

The present invention relates to herbicidal mixtures and their methods and uses for controlling undesirable vegetation in conventional and tolerant, e.g. glufosinate-tolerant, cotton, wherein the herbicidal mixtures comprise L-glufosinate and and at least one herbicidal compound II selected from clethodim, fluazifop, fluazifop-butyl, fluazifop-P, fluazifop-P-butyl, haloxy-fop, halox-yfop-methyl, haloxyfop-P, haloxyfop-P-methyl, metamifop, quizalofop, quizalofop-ethyl, quizalo-fop-tefuryl, quizalofop-P, quizalofop-P-ethyl, quizalofop-P-tefuryl, chlorimuron, chlorimuron-ethyl, thifensulfuron, thifensulfuron-methyl, trifloxysulfuron, tritosulfuron, imazamethabenz, ima-zamethabenz-methyl, imazamox, imazamox ammonium, imazapic, imazapic ammonium, imaza-pyr, imazapyr isopropylammonium, imazaquin, imazethapyr, imazethapyr ammonium, pyrithiobac, pyrithiobac-sodium, amicarbazone, atrazine, prometryn, diuron, fluometuron, thiadiazuron, carfentrazone, carfentrazone-ethyl, flumiclorac, flumiclorac-pentyl, flumioxazin, fluthiacet, fluthiacet-methyl, fomesafen, pyraflufen, pyraf I uf en-ethyl, oxyfluorfen, saflufenacil, sulfentra-zone, tiafenacil, trifludimoxazin, norflurazon, picolinafen, clomazone, topramezone, fenquinotrione, mesotrione, bicyclopyrone, isoxaflutole, tembotrione, tolpyralate, glyphosate, glyphosate dimethylammonium, glyphosate-isopropylammonium, glyphosate-potassium, glyphosate-trimesium (sulfosate), pendimethalin, trifluralin, acetochlor, alachlor, butachlor, dimethenamid, dimethenamid-P, metazachlor, metolachlor, S-metolachlor, pyroxasulfone, 2,4-D and its salts and esters, dicamba and its salts and esters, fluroxypyr, fluroxypyr-butometyl, fluroxypyr-meptyl, quinclorac, quinclorac dimethylammonium, quinmerac, cinmethylin, endothal, cycloxydim, seth-oxydim, diflufenzopyr, diflufenzopyr-sodium, bentazone and bentazone-sodium and other com-pounds. The present invention relates to herbicidal mixtures and their methods and uses for controlling undesirable vegetation in conventional and tolerant, e.g. glufosinate-tolerant, cotton, wherein the herbicidal mixtures comprise L-glufosinate and and at least one herbicidal compound II selected from clethodim, fluazifop, fluazifop-butyl, fluazifop-P, fluazifop-P-butyl, haloxyfop, halox-yfop-methyl, haloxyfop-P, haloxyfop-P-methyl, metamifop, quizalofop, quizalofop-ethyl, quizalo-fop-tefuryl, quizalofop-P, quizalofop-P-ethyl, quizalofop-P-tefuryl, chlorimuron, chlorimuron-ethyl, thifensulfuron, thifensulfuron-methyl, trifloxysulfuron, tritosulfuron, imazamethabenz, ima-zamethabenz-methyl, imazamox, imazamox ammonium, imazapic, imazapic ammonium, imazapyr, imazapyr isopropylammonium, imazaquin, imazethapyr, imazethapyr ammonium, pyrithi-obac, pyrithiobac-sodium, amicarbazone, atrazine, prometryn, diuron, fluometuron, thiadiazuron, carfentrazone, carfentrazone-ethyl, flumiclorac, flumiclorac-pentyl, flumioxazin, fluthiac-et, fluthiacet-methyl, fomesafen, pyraflufen, pyraf I uf en-ethyl, oxyfluorfen, saflufenacil, sulfentra-zone, tiafenacil, trifludimoxazin, norflurazon, picolinafen, clomazone, topramezone, fenquinotri-one, mesotrione, bicyclopyrone, isoxaflutole, tembotrione, tolpyralate, glyphosate, glyphosate dimethylammonium, glyphosate-isopropylammonium, glyphosate- (Continued)

potassium, glyphosate-trimesium (sulfosate), pendimethalin, trifluralin, acetochlor, alachlor, butachlor, dimethenamid, dimethenamid-P, metazachlor, metolachlor, S-metolachlor, pyroxasulfone, 2,4-D and its salts and esters, dicamba and its salts and esters, fluroxypyr, fluroxypyr-butometyl, fluroxypyr-meptyl, quinclorac, quinclorac dimethylammonium, quinmerac, cinmethylin, endothal, cycloxydim, seth-oxydim, diflufenzopyr, diflufenzopyr-sodium, bentazone and bentazone-sodium and other compounds.

20 Claims, No Drawings

(56) References Cited

U.S. PATENT DOCUMENTS

| | | | |
|---|---|---|---|
| 5,530,142 | A | 6/1996 | Zeiss |
| 6,436,874 | B1 | 8/2002 | Kuah et al. |
| 6,569,809 | B1 | 5/2003 | Sato et al. |
| 6,677,276 | B1 | 1/2004 | Hacker et al. |
| 7,105,470 | B1 | 9/2006 | Hacker et al. |
| 2003/0022792 | A1 | 1/2003 | Hacker et al. |
| 2011/0224077 | A1 | 9/2011 | Hacker et al. |
| 2011/0287932 | A1 | 11/2011 | Hacker et al. |
| 2011/0287933 | A1 | 11/2011 | Hacker et al. |
| 2011/0287934 | A1 | 11/2011 | Hacker et al. |
| 2011/0294663 | A1 | 12/2011 | Hacker et al. |
| 2013/0023413 | A1 | 1/2013 | Hacker et al. |
| 2013/0079226 | A1 | 3/2013 | Hacker et al. |
| 2015/0024940 | A1 | 1/2015 | Kim et al. |
| 2015/0157022 | A1 | 6/2015 | Mann et al. |
| 2017/0253897 | A1 | 9/2017 | Green et al. |
| 2021/0022345 | A1 | 1/2021 | Winter et al. |

FOREIGN PATENT DOCUMENTS

| | | | |
|---|---|---|---|
| CN | 102763676 | A | 11/2012 |
| CN | 103053609 | A | 4/2013 |
| CN | 103053610 | A | 4/2013 |
| CN | 103371175 | A | 10/2013 |
| CN | 103688991 | A | 4/2014 |
| CN | 105660687 | A | 6/2016 |
| CN | 105935062 | A | 9/2016 |
| DE | 19501986 | A1 | 7/1996 |
| DE | 19815820 | A1 | 10/1999 |
| DE | 10033832 | A1 | 1/2002 |
| EP | 0127429 | A2 | 12/1984 |
| EP | 0413267 | A1 | 2/1991 |
| EP | 0 537 691 | A1 | 4/1993 |
| EP | 1122244 | B1 | 9/2004 |
| EP | 1459629 | A1 | 9/2004 |
| JP | S59219297 | A | 12/1984 |
| WO | WO-97/24930 | A1 | 7/1997 |
| WO | WO-03/024221 | A1 | 3/2003 |
| WO | WO-2003/028468 | A2 | 4/2003 |
| WO | WO-2006/104120 | A1 | 10/2006 |
| WO | WO-2009/141367 | A2 | 11/2009 |
| WO | WO-2010/067895 | A1 | 6/2010 |
| WO | WO-2012/024524 | A1 | 2/2012 |
| WO | WO-2013/149999 | A1 | 10/2013 |
| WO | WO-2013/154396 | A1 | 10/2013 |
| WO | WO-2016/113334 | A1 | 7/2016 |
| WO | WO-2016/120116 | A1 | 8/2016 |
| WO | WO-2017/007873 | A1 | 1/2017 |
| WO | WO-2017/202768 | A1 | 11/2017 |
| WO | WO-2018/108695 | A1 | 6/2018 |
| WO | WO-2019/030086 | A2 | 2/2019 |
| WO | WO-2019/030087 | A1 | 2/2019 |
| WO | WO-2019/030088 | A1 | 2/2019 |
| WO | WO-2019/030089 | A1 | 2/2019 |
| WO | WO-2019/030090 | A1 | 2/2019 |
| WO | WO-2019/030091 | A2 | 2/2019 |
| WO | WO-2019/030092 | A1 | 2/2019 |
| WO | WO-2019/030095 | A2 | 2/2019 |
| WO | WO-2019/030097 | A2 | 2/2019 |
| WO | WO-2019/030098 | A1 | 2/2019 |
| WO | WO-2019/030099 | A1 | 2/2019 |
| WO | WO-2019/030100 | A1 | 2/2019 |
| WO | WO-2019/030101 | A1 | 2/2019 |
| WO | WO-2019/030102 | A1 | 2/2019 |
| WO | WO-2019/030103 | A1 | 2/2019 |
| WO | WO-2019/030104 | A1 | 2/2019 |

OTHER PUBLICATIONS

Aulakh, et al., "Integrated Palmer Amaranth Management in Glufosinate-Resistant Cotton: II. Primary, Secondary and Conservation Tillage", Agronomy, vol. 3, Issue 1, Jan. 15, 2013, pp. 28-42.

Burke, et al., "Glufosinate Antagonizes Clethodim Control of Goosegrass (*Eleusine indica*)", Weed Technology, vol. 19, Issue 3, Sep. 2005, pp. 664-668.

Cao, et al., "Weeding composition for orchard and corn field weeds, comprises glufosinate or its salt compound and fluroxypyr or its ester compound as active ingredients and pesticide auxiliary agent", WPI / 2017 Clarivate Analytics, Database Accession No. 2013-N83423, XP002786085, Apr. 3, 2013, 2 pages.

Carbonari, et al., "Resistance to glufosinate is proportional to phosphinothricin acetyltransferase expression and activity in LibertyLink and WideStrike cotton", Planta, vol. 243, Issue 4, Jan. 5, 2016, pp. 925-933.

Chen, et al., "Herbicidal composition containing glufosinate-ammonium and aryloxy-phenoxy propionate herbicides, its formulation and application", Database Caplus [Online], Chemical Abstracts Service, Database accession No. 2013:637970, XP002774982, Apr. 24, 2013, 9 pages.

European Search Report for EP Patent Application No. 17185464.9, Issued on Feb. 27, 2018, 7 pages.

Everman, et al., "Weed Control and Yield with Flumioxazin, Fomesafen, and S-Metolachlor Systems for Glufosinate-Resistant Cotton Residual Weed Management", Weed Technology,, vol. 23, Issue 3, Sep. 2009, pp. 391-397.

Gao, et al., "L-glufosinate ammonium/dicamba complex composition", Database Caplus, Chemical Abstracts Service, Database Accession No. 2016:974414, XP002777858, Jun. 15, 2016, 2 pages.

Gardner, et al., "Weed Science—Glufosinate Antagonizes Postemergence Graminicides Applied to Annual Grasses and Johnsongrass", The Journal of Cotton Science, vol. 10, 2006, pp. 319-327.

International Search Report for PCT Patent Application No. PCT/EP2018/070933, Issued on Apr. 1, 2019, 18 pages.

Merchant, et al., "Weed Science: Weed Response to 2,4-D, 2,4-DB, and Dicamba Applied Alone or with Glufosinate", The Journal of Cotton Science, vol. 17, 2013, pp. 212-218.

Nie, et al., "Synergistic herbicidal composition comprising glufosinate-ammonium and dicamba specific for uncultivated area and orchard", Database Caplus (Online), Chemical Abstract Service, XP002781565, Database Accession No. 2011:537286, Apr. 27, 2011, 2 pages.

Regehr, et al., "Field pansy (*Viola rafinesquii* Greene) control in no-till fields with fall- and spring-applied herbicides", Database Caplus, Chemical Abstracts Service, Database Accession No. 2006:39141, XP002780393, Nov. 2, 2005, 2 pages.

Ruhland, et al., "Distribution and metabolism of D/L-, L- and D-glufosinate in transgenic, glufosinate-tolerant crops of maize (*Zea mays* L ssp *mays*) and oilseed rape (*Brassica napus* L var *napus*)", Pest Management Science, vol. 60, Issue 7, 2004, pp. 691-696.

Soloshonok, et al., "Asymmetric synthesis of phosphorus analogues of dicarboxylic ?- amino acids", Journal of the Chemical Society, Perkin Transactions 1, Issue 12, 1992, pp. 1525-1529.

Wang, et al., "Synergistic herbicidal composition containing glufosinate-ammonium and S-metolachlor", Database Caplus(Online), Chemical Abstract Service, XP002780607, Database Accession No. 2012:1492518, Oct. 10, 20122 pages.

(56) References Cited

OTHER PUBLICATIONS

Wang et al., "Glufosinate containing compound herbicide", Database Caplus (Online), Chemical Abstract Service, XP002777920, Database Accession No. 2012:1642498, Nov. 7, 2012, 2 pages.
Xing, et al., "A kind of herbicidal composition containing glufosinate ammonium and amicarbazone and the application thereof", Database Caplus, Chemical Abstracts Service, Database Accession No. 2016:1494642, XP002778246, Sep. 14, 2016, 2 pages.
Yi-yuan, et al., "Progresses in Biosynthesis of L-Phosphinothricin", 2009, 1 page.

HERBICIDAL MIXTURES COMPRISING L-glufosinate AND THEIR USE IN COTTON CULTURES

CROSS-REFERENCE TO RELATED APPLICATIONS

This application is a continuation of U.S. patent application Ser. No. 16/636,840 (filed Feb. 5, 2020), which is incorporated herein by reference in its entirety and is a national stage entry of International Patent Application No. PCT/EP2018/070933 (filed Aug. 2, 2018), which claims the priority benefit of EP application Ser. No. 17/185,464.9 (filed Aug. 9, 2017).

The present invention relates to herbicidal mixture comprising L-glufosinate and and a herbicidal compound II selected from clethodim, fluazifop, fluazifop-butyl, fluazifop-P, fluazifop-P-butyl, haloxyfop, haloxyfop-methyl, haloxyfop-P, haloxyfop-P-methyl, metamifop, quizalofop, quizalofop-ethyl, quizalofop-tefuryl, quizalofop-P, quizalofop-P-ethyl, quizalofop-P-tefuryl, chlorimuron, chlorimuron-ethyl, thifensulfuron, thifensulfuron-methyl, trifloxysulfuron, tritosulfuron, imaza-methabenz, imazamethabenz-methyl, imazamox, imazamox ammonium, imazapic, imazapic ammonium, imazapyr, imazapyr isopropylammonium, imazaquin, imazethapyr, imazethapyr ammonium, pyrithiobac, pyrithiobac-sodium, amicarbazone, atrazine, prometryn, diuron, fluometuron, thiadiazuron, carfentrazone, carfentrazone-ethyl, flumiclorac, flumiclorac-pentyl, flumioxazin, fluthiacet, fluthiacet-methyl, fomesafen, pyraflufen, pyraflufen-ethyl, oxyfluorfen, saflufenacil, sulfentrazone, tiafenacil, trifludimoxazin, norflurazon, picolinafen, clomazone, topramezone, fenquinotrione, mesotrione, bicyclopyrone, isoxaflutole, tembotrione, tolpyralate, glyphosate, glyphosate dimethylammonium, glyphosate-isopropylammonium, glyphosate-potassium, glyphosate-trimesium (sulfosate), pendimethalin, trifluralin, acetochlor, alachlor, butachlor, dimethenamid, dimethenamid-P, metazachlor, metolachlor, S-metolachlor, pyroxasulfone, 2,4-D and its salts and esters, dicamba and its salts and esters, fluroxypyr, fluroxypyrbutometyl, fluroxypyr-meptyl, quinclorac, quinclorac dimethylammonium, quinmerac, cinmethylin, endothal, cycloxydim, sethoxydim, diflufenzopyr, diflufenzopyr-sodium, bentazone, bentazone-sodium, II-83: ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6, S-3100), II-84: 2-[2-chloro-5-[3-chloro-5-(trifluoromethyl)-2-pyridinyl]-4-fluorophenoxy]-2-methoxy-acetic acid methyl ester (CAS 1970221-16-9), II-85: 2-[[3-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy]-N-(methylsulfonyl)acetamide (CAS 2158276-22-1), 11-86: 2-[[3-[[3-chloro-6-[3,6-dihydro-3-methyl-2,6-dioxo-4-(trifluoromethyl)-1(2H)-pyrimidinyl]-5-fluoro-2-pyridinyl] oxy]-2-pyridinyl]oxy]-acetic acid ethyl ester (CAS 2158274-56-5), 11-87: 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-N-(methylsulfonyl)acetamide (CAS 2158274-53-2), 11-88: 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-acetic acid ethyl ester (CAS 2158274-50-9), 11-89: ethyl 2-[[3-[2-chloro-5-[4-(difluoromethyl)-3-methyl-5-oxo-1,2,4-triazol-1-yl]-4-fluoro-phenoxy]-2-pyridyl]oxy]acetate, 11-90: 2-[[3-[[3-chloro-6-[3,6-dihydro-3-methyl-2,6-dioxo-4-(trifluoromethyl)-1(2H)-pyrimidinyl]-5-fluoro-2-pyridinyl] oxy]-2-pyridinyl]oxy]-acetic acid methyl ester (CAS 2158275-73-9), 11-91: 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-acetic acid methyl ester (CAS 2158274-96-3) and II-92: methyl 2-[[3-[2-chloro-5-[4-(difluoromethyl)-3-methyl-5-oxo-1,2,4-triazol-1-yl]-4-fluoro-phenoxy]-2-pyridyl]oxy]acetate.

The invention also relates to methods and uses for controlling undesirable vegetation in cotton, especially glufosinate-tolerant cotton.

Tolerant or resistant cotton varieties (e.g. transgenic cotton varieties) provide the option to use herbicides, which are originally not selective in respective tolerant or resistant cotton in addition to conventional weed control system. One example is glufosinate, which can not only be used for pre-plant burn-down both in conventional cotton and cotton that is tolerant against herbicides including glufosinate; but which can also achieve effective weed control by post-emergence application in conventional or glufosinate tolerant cotton. Glufosinate is a broad-spectrum herbicide that controls most grass and broadleaf herbicide species; however, there are a few tough to control species or resistant biotypes that it does not fully control. Another challenge is the duration of action, or the degradation rate of the herbicide. Furthermore, changes in the sensitivity of harmful plants, which may occur upon prolonged use of the herbicides or within a geographical limited area, must also be taken into consideration. The resulting loss of action against individual plants can sometimes compensated for to a certain extent by higher application rates of the herbicides. However, there is always a demand for methods to achieve the herbicidal effect with lower application rates of active compounds to reduce not only the amount of an active compound required for application, but also the amount of formulation auxiliaries. Thus, low application rates are for economic and environmental reasons an object eco-friendliness of the herbicide treatment.

One possibility for improving the use profile of a herbicide is the combination of the herbicide in question with one or more other active compounds which have the desired additional properties. However, the combined use of a plurality of active compounds may lead to phenomena of a chemical, physical and biological incompatibility (e.g. instability of a coformulation, decomposition of an active compound or antagonism in the biological action of the active compounds). Thus, finding effective glufosinate combinations with an additional herbicide faces the challenge that in many instances the effectiveness of such combinations is not satisfactory and high application rates are still required to achieve an acceptable weed control.

Thus, it is an object of the present invention to find combinations of active compounds with a favorable profile of action, high stability and, ideally, synergistically enhanced activity for application in glufosinate tolerant cotton, which allows the application rate to be reduced in comparison with solutions provided by prior art mixtures. Moreover, the persistence of the herbicidal activity of the mixture should be sufficiently long in order to achieve control of the weeds over a sufficient long time period thus allowing a more flexible application. The mixtures should also show an accelerated action on harmful plants and not affect the growth of the cotton plant.

Glufosinate is a racemate of two enantiomers, out of which only one shows sufficient herbicidal activity (see e.g. U.S. Pat. No. 4,265,654 and JP92448/83). Even though various methods to prepare L-glufosinate (and respective salts) are known, the mixtures known in the art do not point at the stereochemistry, meaning that the racemate is present (e.g. WO 2003024221, WO2009141367, WO2013154396, DE 19815820).

Surprisingly, it has been found that mixtures of L-glufosinate or its salt and the herbicidal compound II show enhanced herbicide action against undesirable vegetation pre-plant burn-down prior to planting of conventional cotton and cotton that is tolerant against herbicides including glufosinate and in post-emergence use in glufosinate tolerant cotton and/or show superior compatibility with cotton, i.e. their use leads to a reduced damage of the cotton plants and/or does not result in increased damage of the cotton plants, if compared to mixtures of racemic glufosinate and the herbicidal compound II, or if compared to L-glufosinate or its salts alone.

Thus, the present invention relates to herbicidal mixtures of
1) L-glufosinate or its salt as compound I and
2) a herbicidal compound II selected from clethodim, fluazifop, fluazifop-butyl, fluazifop-P, fluazifop-P-butyl, haloxyfop, haloxyfop-methyl, haloxyfop-P, haloxyfop-P-methyl, metamifop, quizalofop, quizalofop-ethyl, quizalofop-tefuryl, quizalofop-P, quizalofop-P-ethyl, quizalofop-P-tefuryl, chlorimuron, chlorimuron-ethyl, thifensulfuron, thifensulfuron-methyl, trifloxysulfuron, tritosulfuron, imazamethabenz, imazamethabenz-methyl, imazamox, imazamox ammonium, imazapic, imazapic ammonium, imazapyr, imazapyr isopropylammonium, imazaquin, imazethapyr, imazethapyr ammonium, pyrithiobac, pyrithiobac-sodium, amicarbazone, atrazine, prometryn, diuron, fluometuron, thiadiazuron, carfentrazone, carfentrazone-ethyl, flumiclorac, flumiclorac-pentyl, flumioxazin, fluthiacet, fluthiacet-methyl, fomesafen, pyraflufen, pyraflufen-ethyl, oxyfluorfen, saflufenacil, sulfentrazone, tiafenacil, trifludimoxazin, norflurazon, picolinafen, clomazone, topramezone, fenquinotrione, mesotrione, bicyclopyrone, isoxaflutole, tembotrione, tolpyralate, glyphosate, glyphosate dimethylammonium, glyphosate-isopropylammonium, glyphosate-potassium, glyphosate-trimesium (sulfosate), pendimethalin, trifluralin, acetochlor, alachlor, butachlor, dimethenamid, dimethenamid-P, metazachlor, metolachlor, S-metolachlor, pyroxasulfone, 2,4-D and its salts and esters, dicamba and its salts and esters, fluroxypyr, fluroxypyr-butometyl, fluroxypyr-meptyl, quinclorac, quinclorac dimethylammonium, quinmerac, cinmethylin, endothal, cycloxydim, sethoxydim, diflufenzopyr, diflufenzopyr-sodium, bentazone, bentazone-sodium, 11-83: ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6, S-3100), 11-84: 2-[2-chloro-5-[3-chloro-5-(trifluoromethyl)-2-pyridinyl]-4-fluorophenoxy]-2-methoxy-acetic acid methyl ester (CAS 1970221-16-9), 11-85: 2-[[3-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy]-N-(methylsulfonyl)-acetamide (CAS 2158276-22-1), 11-86: 2-[[3-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl] oxy]-acetic acid ethyl ester (CAS 2158274-56-5), 11-87: 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-N-(methylsulfonyl)acetamide (CAS 2158274-53-2), 11-88: 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-acetic acid ethyl ester (CAS 2158274-50-9) and II-89: ethyl 2-[[3-[2-chloro-5-[4-(difluoromethyl)-3-methyl-5-oxo-1,2,4-triazol-1-yl]-4-fluoro-phenoxy]-2-pyridyl] oxy]acetate (CAS 2230679-62-4), 11-90: 2-[[3-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy]-acetic acid methyl ester (CAS 2158275-73-9), 11-91: 2-[2-[[3-chloro-6-[3,6-dihydro-3-methyl-2,6-dioxo-4-(trifluoromethyl)-1 (2H)-pyrimidinyl]-5-fluoro-2-pyridinyl]oxy]phenoxy]-acetic acid methyl ester (CAS 2158274-96-3); and II-92: methyl 2-[[3-[2-chloro-5-[4-(difluoromethyl)-3-methyl-5-oxo-1,2,4-triazol-1-yl]-4-fluoro-phenoxy]-2-pyridyl]oxy]acetate.

Glufosinate [common name of DL-4-[hydroxyl(methyl) phosphinoyl]-DL-homoalaninate] and its salts such as glufosinate ammonium and its herbicidal activity have been described e.g. by F. Schwerdtle et al. Z. Pflanzenkr. Pflanzenschutz, 1981, Sonderheft IX, pp. 431-440. Racemic glufosinate and its salts are commercially available, e.g. from Bayer CropScience under the tradenames Basta™ and Liberty™.

L-Glufosinate, also called glufosinate-P, is (2S)-2-amino-4-[hydroxy(methyl)phosphinoyl]butyric acid (CAS Reg. No. 35597-44-5). Relevant salts of L-glufosinate are L-glufosinate-ammonium (also called glufosinate-P-ammonium), which is ammonium (2S)-2-amino-4-(methylphosphinato)butyric acid (CAS Reg. No. 73777-50-1); L-glufosinate-sodium (also called glufosinate-P-sodium), which is sodium (2S)-2-amino-4-(methylphosphinato)butyric acid (CAS Reg. No. 70033-13-5) and L-glufosinate-potassium (also called glufosinate-P-potassium), which is potassium (2S)-2-amino-4-(methylphosphinato)butyric acid.

L-Glufosinate as used in the present invention comprises more than 70% by weight of the L-enantiomer; preferably more than 80% by weight of the L-enantiomer; more preferably more than 90% of the L-enantiomer, most preferably more than 95% of the L-enantiomer and can be prepared as referred to above.

In a preferred embodiment, the abovementioned invention relates to herbicidal mixtures as described above, wherein L-glufosinate comprises more than 70% by weight of the L-enantiomer.

L-glufosinate can be prepared according to methods known in the art, e.g. as described in WO2006/104120, U.S. Pat. No. 5,530,142, EP0127429 and J. Chem. Soc. Perkin Trans. 1, 1992, 1525-1529.

Compounds II as well as their pesticidal action and methods for producing them are generally known, for example in the Pesticide Manual V5.2 (ISBN 978 1 901396 85 0) (2008-2011) amongst other sources. Compound II-83 is known from EP 1122244. Compound II-84 is known from WO2016/120116. Compounds 11-85, II-86, II-87, II-88, II-90, II-91 are known from WO2017/202768. Compounds 11-89 and II-92 is known from WO2018/108695.

In the inventive mixtures the weight ratio of compound I to compound II is preferably from 1000:1 to 1:500, 400:1 to 1:40, more preferably 500:1 to 1:250, in particular from 200:1 to 1:20, even more preferably from 100:1 to 1:10, most preferably 50:1 to 1:5.

Furthermore, mixtures are preferred, which contain L-glufosinate-ammonium or L-glufosinate-sodium as L-glufosinate salts or L-glufosinate as free acid. Especially preferred are mixtures, which contain L-glufosinate-ammonium as L-glufosinate salt.

In one embodiment, the present invention relates to herbicidal mixtures of
1) L-glufosinate and its salts, and
2) a herbicidal compound II selected from the group consisting of clethodim, fluazifop, fluazifop-butyl, fluazifop-P, fluazifop-P-butyl, haloxyfop, haloxyfop-methyl, haloxyfop-P, haloxyfop-P-methyl, metamifop, quizalofop, quizalofop-ethyl, quizalofop-tefuryl, quizalofop-P, quizalofop-P-ethyl, quizalofop-P-tefuryl, chlorimuron, chlorimuron-ethyl, thifensulfuron, thifensulfuron-methyl, trifloxysulfuron, tritosulfuron, imazamethabenz, imazamethabenz-methyl, imazamox, imazapic, imazapyr, imazaquin, imazethapyr, pyrithiobac, pyrithiobac-sodium, amicarbazone, atrazine, prometryn, diuron, fluometuron, carfentrazone, carfentrazone-ethyl, flumiclorac, flumiclorac-pentyl, flumioxazin, fluthiacet, fluthiacet-methyl, fomesafen, pyraflufen, pyraflufen-ethyl, saflufenacil, trifludimoxazin, norflurazon, picolinafen, clomazone, topramezone, fenquinotrione, glyphosate, glyphosate-isopropylammonium, glyphosate-potassium, glyphosate-trimesium (sulfosate), pendimethalin, trifluralin, acetochlor, alachlor, butachlor, dimethenamid, dimethenamid-P, metazachlor, metolachlor, metolachlor-S, pyroxasulfone, 2,4-D and its salts and esters, dicamba and its salts and esters, fluroxypyr, fluroxypyr-butometyl, fluroxypyr-meptyl, quinclorac, quinmerac, cinmethylin, endothal, cycloxydim, sethoxydim, diflufenzopyr, diflufenzopyr-sodium, bentazone and bentazone-sodium.

Preferably, the mixtures are mixtures of L-glufosinate and its salts, preferably L-glufosinate-ammonium, L-glufosinate-sodium or L-glufosinate as free acid, and a herbicidal compound II, wherein compound II is selected from the group consisting of clethodim, fluazifop, fluazi-fop-butyl, fluazifop-P, fluazifop-P-butyl, haloxyfop, haloxyfop-methyl, haloxyfop-P, halox-yfop-P-methyl, metamifop, quizalofop, quizalofop-ethyl, quizalofop-tefuryl, quizalofop-P, quizalofop-P-ethyl, quizalofop-P-tefuryl, chlorimuron, chlorimuron-ethyl, thifensulfuron, thif-ensulfuron-methyl, trifloxysulfuron, imazethapyr, pyrithiobac, pyrithiobac-sodium, ami-carbazone, atrazine, prometryn, diuron, fluometuron, carfentrazone, carfentrazone-ethyl, flumiclorac, flumiclorac-pentyl, flumioxazin, fluthiacet, fluthiacet-methyl, fomesafen, pyra-flufen, pyraflufen-ethyl, saflufenacil, trifludimoxazin, norflurazon, clomazone, Fenquinotrione, glyphosate, glyphosate-isopropylammonium, glyphosate-potassium, glyphosate-trimesium (sulfosate), pendimethalin, trifluralin, acetochlor, alachlor, butachlor, dimethena-mid, dimethenamid-P, metolachlor, metolachlor-S, pyroxasulfone, 2,4-D and its salts and esters, dicamba and its salts and esters, fluroxypyr, fluroxypyr-butometyl, fluroxypyr-meptyl, endothal, cycloxydim, sethoxydim, diflufenzopyr, diflufenzopyr-sodium, bentazone and bentazone-sodium;

preferably, wherein compound II is selected from the group consisting of clethodim, fluazifop, fluazifop-butyl, fluazifop-P, fluazifop-P-butyl, haloxyfop, haloxyfop-methyl, haloxyfop-P, haloxyfop-P-methyl, quizalofop, quizalofop-ethyl, quizalofop-tefuryl, quizalofop-P, quizalofop-P-ethyl, quizalofop-P-tefuryl, trifloxysulfuron, imazethapyr, pyrithiobac, pyrithiobac-sodium, atrazine, prometryn, diuron, flumioxazin, fomesafen, saflufenacil, trifludimoxazin, clomazone, Fenquinotrione, glyphosate, glyphosate-isopropylammonium, glyphosate-potassium, glyphosate-trimesium (sulfosate), pendimethalin, trifluralin, acetochlor, butachlor, dimethenamid, dimethenamid-P, metolachlor, metolachlor-S, pyroxasulfone, 2,4-D and its salts and esters, dicamba and its salts and esters, fluroxypyr, fluroxypyr-butometyl, fluroxypyr-meptyl, cycloxydim, sethox-ydim, diflufenzopyr, diflufenzopyr-sodium, bentazone and bentazone-sodium.

Preferred compounds II are clethodim, fluazifop, fluazifop-butyl, fluazifop-P, fluazifop-P-butyl, haloxyfop, haloxyfop-methyl, haloxyfop-P, haloxyfop-P-methyl, metamifop, quizalofop, quizalofop-ethyl, quizalofop-tefuryl, quizalofop-P, quizalofop-P-ethyl, quizalofop-P-tefuryl, chlorimuron, chlorimuron-ethyl, thifensulfuron, thifensulfuron-methyl, trifloxysulfuron, imazethapyr, imazethapyr ammonium, pyrithiobac, pyrithiobac-sodium, amicarbazone, atrazine, prometryn, diuron, fluometuron, thiadiazuron, carfentrazone, carfentrazone-ethyl, flumiclorac, flumiclorac-pentyl, flumioxazin, fluthiacet, fluthiacet-methyl, fomesafen, pyraflufen, pyraflufen-ethyl, oxyfluorfen, saflufenacil, sulfentrazone, tiafenacil, trifludimoxazin, norflurazon, clomazone, topramezone, fenquinotrione, mesotrione, bicyclopyrone, isoxaflutole, tembotrione, tolpyralate, glyphosate, glyphosate dimethylammonium, glyphosate-isopropylammonium, glyphosate-potassium, glyphosate-trimesium (sulfosate), pendimethalin, trifluralin, acetochlor, alachlor, butachlor, dimethenamid, dimethenamid-P, metolachlor, S-metolachlor, pyroxasulfone, 2,4-D and its salts and esters, dicamba and its salts and esters, fluroxypyr, fluroxypyr-butometyl, fluroxypyr-meptyl, endothal, cycloxydim, sethoxydim, diflufenzopyr, diflufenzopyr-sodium, bentazone, bentazone-sodium compounds II-83, II-84, II-85, II-86, II-87, II-88, II-89, II-90, II-91 and II-92. Thus, preferred mixtures of the present invention are mixtures of L-glufosinate-ammonium or L-glufosinate-sodium as L-glufosinate salts or L-glufosinate as free acid and a herbicidal compound II selected from the group consisting of clethodim, fluazifop, fluazifop-butyl, fluazifop-P, fluazifop-P-butyl, haloxyfop, haloxyfop-methyl, haloxyfop-P, haloxyfop-P-methyl, metamifop, quizalofop, quizalofop-ethyl, quizalofop-tefuryl, quizalofop-P, quizalofop-P-ethyl, quizalofop-P-tefuryl, chlorimuron, chlorimuron-ethyl, thifensulfuron, thifensulfuron-methyl, trifloxysulfuron, imazethapyr, imazethapyr ammonium, pyrithiobac, pyrithiobac-sodium, amicarbazone, atrazine, prometryn, diuron, fluometuron, thiadiazuron, carfentrazone, carfentrazone-ethyl, flumiclorac, flumiclorac-pentyl, flumioxazin, fluthiacet, fluthiacet-methyl, fomesafen, pyraflufen, pyraflufen-ethyl, oxyfluorfen, saflufenacil, sulfentrazone, tiafenacil, trifludimoxazin, norflurazon, clomazone, topramezone, fenquinotrione, mesotrione, bicyclopyrone, isoxaflutole, tembotrione, tolpyralate, glyphosate, glyphosate dimethylammonium, glyphosate-isopropylammonium, glyphosate-potassium, glyphosate-trimesium (sulfosate), pendimethalin, trifluralin, acetochlor, alachlor, butachlor, dimethenamid, dimethenamid-P, metolachlor, S-metolachlor, pyroxasulfone, 2,4-D and its salts and esters, dicamba and its salts and esters, fluroxypyr, fluroxypyr-butometyl, fluroxypyr-meptyl, endothal, cycloxydim, sethoxydim, diflufenzopyr, diflufenzopyr-sodium, bentazone, bentazone-sodium, compounds II-83, II-84, II-85, II-86, II-87, II-88, II-89, II-90, II-91 and II-92.

In one embodiment, the compounds II in the mixtures of the invention are selected from the group consisting of prometryn, diuron, fluometuron, thiadiazuron, carfentrazone, carfentrazone-ethyl, flumioxazin, fomesafen, pyraflufen, pyraflufen-ethyl, oxyfluorfen, saflufenacil, sulfentrazone, tiafenacil, trifludimoxazin, topramezone, fenquinotrione, mesotrione, bicyclopyrone, isoxaflutole, tembotrione, tolpyralate, pendimethalin, trifluralin, acetochlor, dimethenamid, dimethenamid-P, metolachlor, S-metolachlor, 2,4-D and its salts and esters, dicamba and its salts and esters, compounds II-83, II-84, II-85, II-86, II-87, II-88, II-89, II-90, II-91 and II-92.

In a further embodiment, the compounds II are selected from the group consisting of prometryn, diuron, fluometuron, thiadiazuron, flumioxazin, saflufenacil, sulfentrazone, tiafenacil, trifludimoxazin, topramezone, fenquinotrione, mesotrione, bicyclopyrone, isoxaflutole, tembotrione, tolpyralate, pendimethalin, dimethenamid, dimethenamid-P, 2,4-D and its salts and esters, dicamba and its salts and esters, compounds II-83, II-84, II-85, II-86, II-87, II-88, II-89, II-90, II-91 and II-92.

In another embodiment, the compounds II in the mixtures of the invention are selected from the group consisting of dimethenamid, dimethenamid-P, acetochlor, metolachlor, S-metolachlor; preferably from the group of dimethenamid and dimethenamid-P.

In another embodiment, the compounds II in the mixtures of the invention are selected from the group consisting of carfentrazone, carfentrazone-ethyl, pyraflufen, pyraflufen-ethyl, flumioxazin, fomesafen, oxyfluorfen, saflufenacil, sulfentrazone, tiafenacil, trifludimoxazin, compounds II-83, II-84, II-85, II-86, II-87, II-88, II-89, II-90, II-91 and II-92; preferably from the group of flumioxazin, saflufenacil, sulfentrazone, tiafenacil, trifludimoxazin, compounds II-83, II-84, II-85, II-86, II-87, II-88, II-89, II-90, II-91 and II-92.

In another embodiment, the compounds II in the mixtures of the invention are selected from the group consisting of topramezone, fenquinotrione, mesotrione, bicyclopyrone, isoxaflutole, tembotrione and tolpyralate.

In another embodiment, the compounds II in the mixtures of the invention are selected from the group consisting of pendimethalin and trifluralin; preferably pendimethalin.

In another embodiment, the compounds II in the mixtures of the invention are selected from the group consisting of prometryn, diuron, fluometuron and thiadiazuron.

In another embodiment, the compounds II in the mixtures of the invention are selected from the group consisting of 2,4-D and its salts and esters, dicamba and its salts and esters.

Thus, in one embodiment of the invention, the mixtures of the invention are mixtures of L-glufosinate-ammonium or L-glufosinate-sodium as L-glufosinate salts or L-glufosinate as free acid and a herbicidal compound II selected from the group consisting of prometryn, diuron, fluometuron, thiadiazuron, carfentrazone, carfentrazone-ethyl, flumioxazin, fomesafen, pyraflufen, pyraflufen-ethyl, oxyfluorfen, saflufenacil, sulfentrazone, tiafenacil, trifludimoxazin, topramezone, fenquinotrione, mesotrione, bicyclopyrone, isoxaflutole, tembotrione, tolpyralate, pendimethalin, trifluralin, acetochlor, dimethenamid, dimethenamid-P, metolachlor, S-metolachlor, 2,4-D and its salts and esters, dicamba and its salts and esters, compounds II-83, II-84, II-85, II-86, II-87, II-88, II-89, II-90, II-91 and II-92.

Preferred mixtures of the present invention are mixtures of L-glufosinate-ammonium or L-glufosinate-sodium as L-glufosinate salts or L-glufosinate as free acid and a herbicidal compound II selected from the group consisting of prometryn, diuron, fluometuron, thiadiazuron, flumioxazin, saflufenacil, sulfentrazone, tiafenacil, trifludimoxazin, topramezone, fenquinotrione, mesotrione, bicyclopyrone, isoxaflutole, tembotrione, tolpyralate, pendimethalin, dimethenamid, dimethenamid-P, 2,4-D and its salts and esters, dicamba and its salts and esters, compounds II-83, II-84, II-85, II-86, II-87, II-88, II-89, II-90, II-91 and II-92.

In one embodiment of the invention, the mixtures of the invention are mixtures of L-glufosinate-ammonium or L-glufosinate-sodium as L-glufosinate salts or L-glufosinate as free acid and a herbicidal compound II selected from the group consisting of dimethenamid, dimethenamid-P, acetochlor, metolachlor, S-metolachlor; preferably from the group of dimethenamid and dimethenamid-P.

In one embodiment of the invention, the mixtures of the invention are mixtures of L-glufosinate-ammonium or L-glufosinate-sodium as L-glufosinate salts or L-glufosinate as free acid and a herbicidal compound II selected from the group consisting of carfentrazone, carfentrazone-ethyl, pyraflufen, pyraflufen-ethyl, flumioxazin, fomesafen, oxyfluorfen, saflufenacil, sulfentrazone, tiafenacil, trifludimoxazin, compounds II-83, II-84, II-85, II-86, II-87, II-88, II-89, II-90, II-91 and II-92; preferably from the group of flumioxazin, saflufenacil, sulfentrazone, tiafenacil, trifludimoxazin, compounds II-83, II-84, II-85, II-86, II-87, II-88, II-89, II-90, II-91 and II-92.

In one embodiment of the invention, the mixtures of the invention are mixtures of L-glufosinate-ammonium or L-glufosinate-sodium as L-glufosinate salts or L-glufosinate as free acid and a herbicidal compound II selected from the group consisting of topramezone, fenquinotrione, mesotrione, bicyclopyrone, isoxaflutole, tembotrione and tolpyralate.

In one embodiment of the invention, the mixtures of the invention are mixtures of L-glufosinate-ammonium or L-glufosinate-sodium as L-glufosinate salts or L-glufosinate as free acid and a herbicidal compound II selected from the group consisting of pendimethalin and trifluralin; preferably pendimethalin.

In one embodiment of the invention, the mixtures of the invention are mixtures of L-glufosinate-ammonium or L-glufosinate-sodium as L-glufosinate salts or L-glufosinate as free acid and a herbicidal compound II selected from the group consisting of prometryn, diuron, fluometuron and thiadiazuron.

In one embodiment of the invention, the mixtures of the invention are mixtures of L-glufosinate-ammonium or L-glufosinate-sodium as L-glufosinate salts or L-glufosinate as free acid and a herbicidal compound II selected from the group consisting of 2,4-D and its salts and esters, dicamba and its salts and esters.

All preferred mixtures are listed in table 2, wherein the following abbreviations are used in table 1:

TABLE 1

| Compound | Abbreviation |
| --- | --- |
| L-glufosinate-ammonium | I-1 |
| L-glufosinate-sodium | I-2 |
| L-glufosinate as free acid | I-3 |
| clethodim | II-1 |
| fluazifop | II-2 |
| fluazifop-butyl | II-3 |
| fluazifop-P | II-4 |
| fluazifop-P-butyl | II-5 |
| haloxyfop | II-6 |
| haloxyfop-methyl | II-7 |
| haloxyfop-P | II-8 |
| haloxyfop-P-methyl | II-9 |
| quizalofop | II-10 |
| quizalofop-ethyl | II-11 |
| quizalofop-tefuryl | II-12 |

TABLE 1-continued

| Compound | Abbreviation |
| --- | --- |
| quizalofop-P | II-13 |
| quizalofop-P-ethyl | II-14 |
| quizalofop-P-tefuryl | II-15 |
| trifloxysulfuron | II-16 |
| imazethapyr | II-17 |
| pyrithiobac | II-18 |
| pyrithiobac-sodium | II-19 |
| atrazine | II-20 |
| prometryn | II-21 |
| diuron | II-22 |
| flumioxazin | II-23 |
| fomesafen | II-24 |
| saflufenacil | II-25 |
| trifludimoxazin | II-26 |
| clomazone | II-27 |
| fenquinotrione | II-28 |
| glyphosate | II-29 |
| glyphosate-isopropylammonium | II-30 |
| glyphosate-potassium | II-31 |
| glyphosate-trimesium (sulfosate) | II-32 |
| pendimethalin | II-33 |
| trifluralin | II-34 |
| acetochlor | II-35 |
| butachlor | II-36 |
| dimethenamid | II-37 |
| dimethen-amid-P | II-38 |
| metolachlor | II-39 |
| S-metolachlor | II-40 |
| pyroxasulfone | II-41 |
| 2,4-D and its salts and esters | II-42 |
| dicamba and its salts and esters | II-43 |
| fluroxypyr | II-44 |
| fluroxypyr-butometyl | II-45 |
| fluroxy-pyr-meptyl | II-46 |
| cycloxydim | II-47 |
| sethoxydim | II-48 |
| diflufenzopyr | II-49 |
| diflufenzopyr-sodium | II-50 |
| bentazone | II-51 |
| bentazone-sodium | II-52 |
| metamifop | II-53 |
| chlorimuron | II-54 |
| chlorimuron-ethyl | II-55 |
| thifensulfuron | II-56 |
| thifensulfuron-methyl | II-57 |
| fluometuron | II-58 |
| carfentrazone | II-59 |
| carfentrazone-ethyl | II-60 |
| flumiclorac | II-61 |
| flumiclorac-pentyl | II-62 |
| arnicarbazone | II-63 |
| fluthiacet | II-64 |
| fluthiacet-methyl | II-65 |
| pyraflufen | II-66 |
| pyraflufen-ethyl | II-67 |
| norflurazon | II-68 |
| alachlor | II-69 |
| endothal | II-70 |
| imazethapyr ammonium | II-71 |
| glyphosate dimethylammonium | II-72 |
| oxyfluorfen | II-73 |
| sulfentrazone | II-74 |
| tiafenacil | II-75 |
| thiadiazuron | II-76 |
| see below | II-83 |
| see below | II-84 |
| see below | II-85 |
| see below | II-86 |
| see below | II-87 |
| see below | II-88 |
| see below | II-89 |
| see below | II-90 |
| see below | II-91 |
| see below | II-92 |
| topramezone | II-93 |
| mesotrione | II-94 |
| bicyclopyrone | II-95 |
| isoxaflutole | II-96 |
| tembotrione | II-97 |
| tolpyralate | II-98 |

II-83: ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100).
II-84: 2-[2-chloro-5-[3-chloro-5-(trifluoromethyl)-2-pyridinyl]-4-fluorophenoxy]-2-methoxy-acetic acid methyl ester (CAS 1970221-16-9)
II-85: 2-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy]-N-(methylsulfonyl)-acetamide (CAS 2158276-22-1)
II-86: 2-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy]-acetic acid ethyl ester (CAS 2158274-56-5)
II-87: 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-N-(methylsulfonyl)-acetamide (CAS 2158274-53-2)
II-88: 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-acetic acid ethyl ester (CAS 2158274-50-9)
II-89: ethyl 2-[[3-[2-chloro-5-[4-(trifluoromethyl)-3-methyl-5-oxo-1,2,4-triazol-1-yl]-4-fluoro-phenoxy]-2-pyridyl]oxy]acetate
II-90: 2-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy]-acetic acid methyl ester (CAS 2158275-73-9)
II-91: 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-acetic acid methyl ester (CAS 2158274-96-3)
II-92: methyl 2-[[3-[2-chloro-5-[4-(difluoromethyl)-3-methyl-5-oxo-1,2,4-triazol-1-yl]-4-fluoro-phenoxy]-2-pyridyl]oxy]acetate

TABLE 2

| No | I | II |
| --- | --- | --- |
| M-1 | I-1 | II-1 |
| M-2 | I-1 | II-2 |
| M-3 | I-1 | II-3 |
| M-4 | I-1 | II-4 |
| M-5 | I-1 | II-5 |
| M-6 | I-1 | II-6 |
| M-7 | I-1 | II-7 |
| M-8 | I-1 | II-8 |
| M-9 | I-1 | II-9 |
| M-10 | I-1 | II-10 |
| M-11 | I-1 | II-11 |
| M-12 | I-1 | II-12 |
| M-13 | I-1 | II-13 |
| M-14 | I-1 | II-14 |
| M-15 | I-1 | II-15 |
| M-16 | I-1 | II-16 |
| M-17 | I-1 | II-17 |
| M-18 | I-1 | II-18 |
| M-19 | I-1 | II-19 |
| M-20 | I-1 | II-20 |
| M-21 | I-1 | II-21 |
| M-22 | I-1 | II-22 |
| M-23 | I-1 | II-23 |
| M-24 | I-1 | II-24 |
| M-25 | I-1 | II-25 |
| M-26 | I-1 | II-26 |
| M-27 | I-1 | II-27 |
| M-28 | I-1 | II-28 |
| M-29 | I-1 | II-29 |
| M-30 | I-1 | II-30 |
| M-31 | I-1 | II-31 |
| M-32 | I-1 | II-32 |
| M-33 | I-1 | II-33 |
| M-34 | I-1 | II-34 |
| M-35 | I-1 | II-35 |
| M-36 | I-1 | II-36 |
| M-37 | I-1 | II-37 |
| M-38 | I-1 | II-38 |
| M-39 | I-1 | II-39 |
| M-40 | I-1 | II-40 |
| M-41 | I-1 | II-41 |
| M-42 | I-1 | II-42 |
| M-43 | I-1 | II-43 |
| M-44 | I-1 | II-44 |
| M-45 | I-1 | II-45 |
| M-46 | I-1 | II-46 |
| M-47 | I-1 | II-47 |
| M-48 | I-1 | II-48 |
| M-49 | I-1 | II-49 |
| M-50 | I-1 | II-50 |

TABLE 2-continued

| No | I | II |
|---|---|---|
| M-51 | I-1 | II-51 |
| M-52 | I-1 | II-52 |
| M-53 | I-1 | II-53 |
| M-54 | I-1 | II-54 |
| M-55 | I-1 | II-55 |
| M-56 | I-1 | II-56 |
| M-57 | I-1 | II-57 |
| M-58 | I-1 | II-58 |
| M-59 | I-1 | II-59 |
| M-60 | I-1 | II-60 |
| M-61 | I-1 | II-61 |
| M-62 | I-1 | II-62 |
| M-63 | I-1 | II-63 |
| M-64 | I-1 | II-64 |
| M-65 | I-1 | II-65 |
| M-66 | I-1 | II-66 |
| M-67 | I-1 | II-67 |
| M-68 | I-1 | II-68 |
| M-69 | I-1 | II-69 |
| M-70 | I-1 | II-70 |
| M-71 | I-2 | II-1 |
| M-72 | I-2 | II-2 |
| M-73 | I-2 | II-3 |
| M-74 | I-2 | II-4 |
| M-75 | I-2 | II-5 |
| M-76 | I-2 | II-6 |
| M-77 | I-2 | II-7 |
| M-78 | I-2 | II-8 |
| M-79 | I-2 | II-9 |
| M-80 | I-2 | II-10 |
| M-81 | I-2 | II-11 |
| M-82 | I-2 | II-12 |
| M-83 | I-2 | II-13 |
| M-84 | I-2 | II-14 |
| M-85 | I-2 | II-15 |
| M-86 | I-2 | II-16 |
| M-87 | I-2 | II-17 |
| M-88 | I-2 | II-18 |
| M-89 | I-2 | II-19 |
| M-90 | I-2 | II-20 |
| M-91 | I-2 | II-21 |
| M-92 | I-2 | II-22 |
| M-93 | I-2 | II-23 |
| M-94 | I-2 | II-24 |
| M-95 | I-2 | II-25 |
| M-96 | I-2 | II-26 |
| M-97 | I-2 | II-27 |
| M-98 | I-2 | II-28 |
| M-99 | I-2 | II-29 |
| M-100 | I-2 | II-30 |
| M-101 | I-2 | II-31 |
| M-102 | I-2 | II-32 |
| M-103 | I-2 | II-33 |
| M-104 | I-2 | II-34 |
| M-105 | I-2 | II-35 |
| M-106 | I-2 | II-36 |
| M-107 | I-2 | II-37 |
| M-108 | I-2 | II-38 |
| M-109 | I-2 | II-39 |
| M-110 | I-2 | II-40 |
| M-111 | I-2 | II-41 |
| M-112 | I-2 | II-42 |
| M-113 | I-2 | II-43 |
| M-114 | I-2 | II-44 |
| M-115 | I-2 | II-45 |
| M-116 | I-2 | II-46 |
| M-117 | I-2 | II-47 |
| M-118 | I-2 | II-48 |
| M-119 | I-2 | II-49 |
| M-120 | I-2 | II-50 |
| M-121 | I-2 | II-51 |
| M-122 | I-2 | II-52 |
| M-123 | I-2 | II-53 |
| M-124 | I-2 | II-54 |
| M-125 | I-2 | II-55 |
| M-126 | I-2 | II-56 |
| M-127 | I-2 | II-57 |
| M-128 | I-2 | II-58 |
| M-129 | I-2 | II-59 |
| M-130 | I-2 | II-60 |
| M-131 | I-2 | II-61 |
| M-132 | I-2 | II-62 |
| M-133 | I-2 | II-63 |
| M-134 | I-2 | II-64 |
| M-135 | I-2 | II-65 |
| M-136 | I-2 | II-66 |
| M-137 | I-2 | II-67 |
| M-138 | I-2 | II-68 |
| M-139 | I-2 | II-69 |
| M-140 | I-2 | II-70 |
| M-141 | I-3 | II-1 |
| M-142 | I-3 | II-2 |
| M-143 | I-3 | II-3 |
| M-144 | I-3 | II-4 |
| M-145 | I-3 | II-5 |
| M-146 | I-3 | II-6 |
| M-147 | I-3 | II-7 |
| M-148 | I-3 | II-8 |
| M-149 | I-3 | II-9 |
| M-150 | I-3 | II-10 |
| M-151 | I-3 | II-11 |
| M-152 | I-3 | II-12 |
| M-153 | I-3 | II-13 |
| M-154 | I-3 | II-14 |
| M-155 | I-3 | II-15 |
| M-156 | I-3 | II-16 |
| M-157 | I-3 | II-17 |
| M-158 | I-3 | II-18 |
| M-159 | I-3 | II-19 |
| M-160 | I-3 | II-20 |
| M-161 | I-3 | II-21 |
| M-162 | I-3 | II-22 |
| M-163 | I-3 | II-23 |
| M-164 | I-3 | II-24 |
| M-165 | I-3 | II-25 |
| M-166 | I-3 | II-26 |
| M-167 | I-3 | II-27 |
| M-168 | I-3 | II-28 |
| M-169 | I-3 | II-29 |
| M-170 | I-3 | II-30 |
| M-171 | I-3 | II-31 |
| M-172 | I-3 | II-32 |
| M-173 | I-3 | II-33 |
| M-174 | I-3 | II-34 |
| M-175 | I-3 | II-35 |
| M-176 | I-3 | II-36 |
| M-177 | I-3 | II-37 |
| M-178 | I-3 | II-38 |
| M-179 | I-3 | II-39 |
| M-180 | I-3 | II-40 |
| M-181 | I-3 | II-41 |
| M-182 | I-3 | II-42 |
| M-183 | I-3 | II-43 |
| M-184 | I-3 | II-44 |
| M-185 | I-3 | II-45 |
| M-186 | I-3 | II-46 |
| M-187 | I-3 | II-47 |
| M-188 | I-3 | II-48 |
| M-189 | I-3 | II-49 |
| M-190 | I-3 | II-50 |
| M-191 | I-3 | II-51 |
| M-192 | I-3 | II-52 |
| M-193 | I-3 | II-53 |
| M-194 | I-3 | II-54 |
| M-195 | I-3 | II-55 |
| M-196 | I-3 | II-56 |
| M-197 | I-3 | II-57 |
| M-198 | I-3 | II-58 |
| M-199 | I-3 | II-59 |
| M-200 | I-3 | II-60 |
| M-201 | I-3 | II-61 |
| M-202 | I-3 | II-62 |
| M-203 | I-3 | II-63 |
| M-204 | I-3 | II-64 |
| M-205 | I-3 | II-65 |
| M-206 | I-3 | II-66 |

TABLE 2-continued

| No | I | II |
|---|---|---|
| M-207 | I-3 | II-67 |
| M-208 | I-3 | II-68 |
| M-209 | I-3 | II-69 |
| M-210 | I-3 | II-70 |
| M-211 | I-1 | II-71 |
| M-212 | I-1 | II-72 |
| M-213 | I-1 | II-73 |
| M-214 | I-1 | II-74 |
| M-215 | I-1 | II-75 |
| M-216 | I-1 | II-76 |
| M-217 | I-1 | II-83 |
| M-218 | I-1 | II-84 |
| M-219 | I-1 | II-85 |
| M-220 | I-1 | II-86 |
| M-221 | I-1 | II-87 |
| M-222 | I-1 | II-88 |
| M-223 | I-1 | II-89 |
| M-224 | I-1 | II-90 |
| M-225 | I-1 | II-91 |
| M-226 | I-1 | II-92 |
| M-227 | I-2 | II-71 |
| M-228 | I-2 | II-72 |
| M-229 | I-2 | II-73 |
| M-230 | I-2 | II-74 |
| M-231 | I-2 | II-75 |
| M-232 | I-2 | II-76 |
| M-233 | I-2 | II-83 |
| M-234 | I-2 | II-84 |
| M-235 | I-2 | II-85 |
| M-236 | I-2 | II-86 |
| M-237 | I-2 | II-87 |
| M-238 | I-2 | II-88 |
| M-239 | I-2 | II-89 |
| M-240 | I-2 | II-90 |
| M-241 | I-2 | II-91 |
| M-242 | I-2 | II-92 |
| M-243 | I-3 | II-71 |
| M-244 | I-3 | II-72 |
| M-245 | I-3 | II-73 |
| M-246 | I-3 | II-74 |
| M-247 | I-3 | II-75 |
| M-248 | I-3 | II-76 |
| M-249 | I-3 | II-83 |
| M-250 | I-3 | II-84 |
| M-251 | I-3 | II-85 |
| M-252 | I-3 | II-86 |
| M-253 | I-3 | II-87 |
| M-254 | I-3 | II-88 |
| M-255 | I-3 | II-89 |
| M-256 | I-3 | II-90 |
| M-257 | I-3 | II-91 |
| M-258 | I-3 | II-92 |
| M-259 | I-1 | II-93 |
| M-260 | I-1 | II-94 |
| M-261 | I-1 | II-95 |
| M-262 | I-1 | II-96 |
| M-263 | I-1 | II-97 |
| M-264 | I-1 | II-98 |
| M-265 | I-2 | II-93 |
| M-266 | I-2 | II-94 |
| M-267 | I-2 | II-95 |
| M-268 | I-2 | II-96 |
| M-269 | I-2 | II-97 |
| M-270 | I-2 | II-98 |
| M-271 | I-3 | II-93 |
| M-272 | I-3 | II-94 |
| M-273 | I-3 | II-95 |
| M-274 | I-3 | II-96 |
| M-275 | I-3 | II-97 |
| M-276 | I-3 | II-98 |

In one embodiment, the mixtures of the present invention are mixtures of L-glufosinate-ammonium or L-glufosinate-sodium as L-glufosinate salts or L-glufosinate as free acid and at least one compound II selected from the group consisting of clethodim, fluazifop, fluazifop-butyl, fluazifop-P, fluazifop-P-butyl, haloxyfop, haloxyfop-methyl, haloxyfop-P, haloxyfop-P-methyl, quizalofop, quizalofop-ethyl, quizalofop-tefuryl, quizalofop-P, quizalofop-P-ethyl, quizalofop-P-tefuryl, trifloxysulfuron, imazethapyr, imazethapyr ammonium, pyrithiobac, pyrithiobac-sodium, atrazine, prometryn, diuron, flumioxazin, fomesafen, saflufenacil, sulfentrazone, tiafenacil, trifludimoxazin, clomazone, topramezone fenquinotrione, mesotrione, bicyclopyrone, isoxaflutole, tembotrione, tolpyralate, glyphosate, glyphosate dimethylammonium, glyphosate-isopropylammonium, glyphosate-potassium, glyphosate-trimesium (sulfosate), pendimethalin, trifluralin, acetochlor, butachlor, dimethenamid, dimethenamid-P, metolachlor, S-metolachlor, pyroxasulfone, 2,4-D and its salts and esters, dicamba and its salts and esters, fluroxypyr, fluroxypyr-butometyl, fluroxypyr-meptyl, cycloxydim, sethoxydim, diflufenzopyr, diflufenzopyr-sodium, bentazone, bentazone-sodium, compounds II-83, II-84, II-85, II-86, II-87, II-88, II-89, II-90, II-91 and II-92.

In one embodiment, the mixtures of the invention are mixtures selected from the group consisting of M-1, M-2, M-3, M-4, M-5, M-6, M-7, M-8, M-9, M-10, M-11, M-12, M-13, M-14, M-15, M16, M-17, M-18, M-19, M-20, M-21, M-22, M-23, M-24, M-25, M-26, M-27, M-28, M-29, M-30, M31, M-32, M-33, M-34, M-35, M-36, M-37, M-38, M-39, M-40, M-41, M-42, M-43, M-44, M-45, M46, M-47, M-48, M-49, M-50, M-51, M-52, M-53, M-54, M-55, M-56, M-57, M-58, M-59, M-60, M61, M-62, M-63, M-64, M-65, M-66, M-67, M-68, M-69, M-70, M-71, M-72, M-73, M-74, M-75, M76, M-77, M-78, M-79, M-80, M-81, M-82, M-83, M-84, M-85, M-86, M-87, M-88, M-89, M-90, M91, M-92, M-93, M-94, M-95, M-96, M-97, M-98, M-99, M-100, M-101, M-102, M-103, M-104, M105, M-106, M-107, M-108, M-109, M-110, M-111, M-112, M-113, M-114, M-115, M-116, M117, M-118, M-119, M-120, M-121, M-122, M-123, M-124, M-125, M-126, M-127, M-128, M129, M-130, M-131, M-132, M-133, M-134, M-135, M-136, M-137, M-138, M-139, M-140, M141, M-142, M-143, M-144, M-145, M-146, M-147, M-148, M-149, M-150, M-151, M-152, M153, M-154, M-155, M-156, M-157, M-158, M-159, M-160, M-161, M-162, M-163, M-164, M165, M-166, M-167, M-168, M-169, M-170, M-171, M-172, M-173, M-174, M-175, M-176, M177, M-178, M-179, M-180, M-181, M-182, M-183, M-184, M-185, M-186, M-187, M-188, M189, M-190, M-191, M-192, M-193, M-194, M-195, M-196, M-197, M-198, M-199, M-200, M201, M-202, M-203, M-204, M-205, M-206, M-207, M-208, M-209, M-210, M-211, M-212, M213, M-214, M-215, M-216, M-217, M-218, M-219, M-220, M-221, M-222, M-223, M-224, M225, M-226, M-227, M-228, M-229, M-230, M-231, M-232, M-233, M-234, M-235, M-236, M237, M-238, M-239, M-240, M-241, M-242, M-243, M-244, M-245, M-246, M-247, M-248, M249, M-250, M-251, M-252, M-253, M-254, M-255, M-256, M-257, M-258, M-259, M-260, M261, M-262, M-263, M-264, M-265, M-266, M-267, M-268, M-269, M-270, M-271, M-272, M273, M-274, M-275, M-276.

In a preferred embodiment, the mixtures are selected from the group consisting of M-21, M-22, M-23, M-24, M-25, M-26, M-33, M-34, M-35, M-37, M-38, M-39, M-40, M-42, M-43, M-58, M-59, M-60, M-66, M-67, M-91, M-92, M-93, M-94, M-95, M-96, M-103, M-104, M-105, M-107, M-108, M-109, M-110, M-112, M-113, M-128, M-129, M-130, M-136, M-137, M-161, M-162, M-163, M164, M-165, M-166, M-173, M-174, M-175, M-177, M-178, M-179, M-180, M-182, M-183, M198, M-199, M-200, M-206, M-207, M-213, M-214, M-215, M-216, M-217, M-218, M-219, M220, M-221, M-222, M-223, M-224, M-225, M-226, M-229, M-230, M-231, M-232, M-233, M234, M-235, M-236, M-237, M-238, M-239, M-240, M-241, M-242, M-245, M-246, M-247, M248, M-249, M-250, M-251, M-252, M-253, M-254, M-255, M-256, M-257, M-258, M-259, M260, M-261, M-262, M-263, M-264, M-265, M-266, M-267, M-268, M-269, M-270, M-271, M272, M-273, M-274, M-275, M-276;

respectively the group of M-21, M-22, M-23, M-24, M-25, M-26, M-33, M-34, M-35, M-37, M-38, M-39, M-40, M-42, M-43, M-58, M-59, M-60, M-66, M-67, M-213, M-214, M-215, M-216, M-217, M-218, M-219, M-220, M-221, M-222, M-223, M-224, M-225, M-226, M-258, M-259, M-260, M261, M-262, M-263, M-264, M-265, M-266, M-267, M-268, M-269, M-270, M-271, M-272, M273, M-274, M-275, M-276;

respectively the group of M-21, M-22, M-23, M-24, M-25, M-26, M-33, M-34, M-35, M-37, M-38, M-39, M-40, M-42, M-43, M-58, M-59, M-60, M-66, M-67, M-213, M-214, M-215, M-216, M-217, M-218, M-219, M-220, M-221, M-222, M-223, M-224, M-225, M-226;

respectively the group of M-91, M-92, M-93, M-94, M-95, M-96, M-103, M-104, M-105, M-107, M-108, M-109, M-110, M-112, M-113, M-128, M-129, M-130, M-136, M-137, M-229, M-230, M231, M-232, M-233, M-234, M-235, M-236, M-237, M-238, M-239, M-240, M-241, M-242; respectively the group of M-161, M-162, M-163, M-164, M-165, M-166, M-173, M-174, M-175, M-177, M-178, M-179, M-180, M-182, M-183, M-198, M-199, M-200, M-206, M-207, M-245, M246, M-247, M-248, M-249, M-250, M-251, M-252, M-253, M-254, M-255, M-256, M-257, M-258.

In a preferred embodiment, the mixtures above further include the mixtures selected from the group consisting of M-258, M-259, M-260, M-261, M-262, M-263, M-264, M-265, M-266, M-267, M-268, M-269, M-270, M-271, M-272, M-273, M-274, M-275, M-276.

In a most preferred embodiment, the mixtures are selected from the group consisting of M-21, M-22, M-23, M-25, M-26, M-33, M-37, M-38, M-42, M-43, M-58, M-91, M-92, M-93, M-95, M-96, M-103, M-107, M-108, M-112, M-113, M-128, M-161, M-162, M-163, M-165, M-166, M-173, M177, M-178, M-182, M-183, M-198, M-214, M-215, M-216, M-217, M-218, M-219, M-220, M221, M-222, M-223, M-224, M-225, M-226, M-230, M-231, M-232, M-233, M-234, M-235, M236, M-237, M-238, M-239, M-240, M-241, M-242, M-246, M-247, M-248, M-249, M-250, M251, M-252, M-253, M-254, M-255, M-256, M-257, M-258, M-258, M-259, M-260, M-261, M262, M-263, M-264, M-265, M-266, M-267, M-268, M-269, M-270, M-271, M-272, M-273, M274, M-275, M-276;

respectively the group of M-21, M-22, M-23, M-25, M-26, M-33, M-37, M-38, M-42, M-43, M-58, M-214, M-215, M-216, M-217, M-218, M-219, M-220, M-221, M-222, M-223, M-224, M-225, M226;

respectively the group of M-91, M-92, M-93, M-95, M-96, M-103, M-107, M-108, M-112, M-113, M-128, M-230, M-231, M-232, M-233, M-234, M-235, M-236, M-237, M-238, M-239, M-240, M241, M-242;

respectively the group of M-161, M-162, M-163, M-165, M-166, M-173, M-177, M-178, M-182, M-183, M-198, M-246, M-247, M-248, M-249, M-250, M-251, M-252, M-253, M-254, M-255, M256, M-257, M-258.

In a preferred embodiment, the mixtures above further include the mixtures selected from the group consisting of M-258, M-259, M-260, M-261, M-262, M-263, M-264, M-265, M-266, M-267, M-268, M-269, M-270, M-271, M-272, M-273, M-274, M-275, M-276.

All above-referred mixtures are herein below referred to as "inventive mixtures".

The inventive mixtures can further contain one or more insecticides, fungicides, herbicides.

The inventive mixtures can be converted into customary types of agrochemical mixtures, e. g. solutions, emulsions, suspensions, dusts, powders, pastes, granules, pressings, capsules, and mixtures thereof. Examples for mixture types are suspensions (e.g. SC, OD, FS), emulsifiable concentrates (e.g. EC), emulsions (e.g. EW, EO, ES, ME), capsules (e.g. CS, ZC), pastes, pastilles, wetable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further mixtures types are defined in the "Catalogue of pesticide formulation types and international coding system", Technical Monograph No. 2, $6^{th}$ Ed. May 2008, CropLife International.

The mixtures are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005. Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders. Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides.

Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinylamines or polyethylene-amines.

Suitable adjuvants are compounds, which have a neglectable or even no pesticidal activity themselves, and which improve the biological performance of the inventive mixtures on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for mixture types and their preparation are:
i) Water-Soluble Concentrates (SL, LS)
10-60 wt % of an inventive mixture and 5-15 wt % wetting agent (e.g. alcohol alkoxylates) are dissolved in water and/or in a water-soluble solvent (e.g. alcohols) ad 100 wt %. The active substance dissolves upon dilution with water.
ii) Dispersible Concentrates (DC)
5-25 wt % of an inventive mixture and 1-10 wt % dispersant (e. g. polyvinylpyrrolidone) are dissolved in organic solvent (e.g. cyclohexanone) ad 100 wt %. Dilution with water gives a dispersion.
iii) Emulsifiable Concentrates (EC)
15-70 wt % of an inventive mixture and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.
iv) Emulsions (EW, EO, ES)
5-40 wt % of an inventive mixture and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.
v) Suspensions (SC, OD, FS)
In an agitated ball mill, 20-60 wt % of an inventive mixture are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type mixture up to 40 wt % binder (e.g. polyvinylalcohol) is added.
vi) Water-Dispersible Granules and Water-Soluble Granules (WG, SG)
50-80 wt % of an inventive mixture are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.
vii) Water-Dispersible Powders and Water-Soluble Powders (WP, SP, WS)
50-80 wt % of an inventive mixture are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.
viii) Gel (GW, GF)
In an agitated ball mill, 5-25 wt % of an inventive mixture are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.
ix) Microemulsion (ME)
5-20 wt % of an inventive mixture are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.
x) Microcapsules (CS)
An oil phase comprising 5-50 wt % of an inventive mixture, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of an inventive mixture according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS mixture.

xi) Dustable Powders (DP, DS)

1-10 wt % of an inventive mixture are ground finely and mixed intimately with solid carrier (e.g. finely divided kaolin) ad 100 wt %.

x) Granules (GR, FG)

0.5-30 wt % of an inventive mixture is ground finely and associated with solid carrier (e.g. silicate) ad 100 wt %. Granulation is achieved by extrusion, spray-drying or fluidized bed.

xii) Ultra-Low Volume Liquids (UL)

1-50 wt % of an inventive mixture are dissolved in organic solvent (e.g. aromatic hydrocarbon) ad 100 wt %.

The mixtures types i) to xii) may optionally comprise further auxiliaries, such as 0.1-1 wt % bactericides, 5-15 wt % anti-freezing agents, 0.1-1 wt % anti-foaming agents, and 0.1-1 wt % colorants.

The resulting agrochemical mixtures generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds.

The mixtures in question give, after two-to-tenfold dilution, active substance concentrations of from 0.01 to 60% by weight, preferably from 0.1 to 40%, in the ready-to-use preparations. Application can be carried out before or during sowing. Methods for applying the inventive mixtures and mixtures thereof, respectively, on to plant propagation material, especially seeds include dressing, coating, pelleting, dusting, soaking and in-furrow application methods of the propagation material. Preferably, the inventive mixtures or the mixtures thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the active substances or the inventive mixtures comprising them as premix or, if appropriate not until immediately prior to use (tank mix). These agents can be admixed with the inventive mixtures in a weight ratio of 1:100 to 100:1, preferably 1:10 to 10:1.

The user applies the mixture according to the invention usually from a predosage device, a knapsack sprayer, a spray tank, a spray plane, or an irrigation system. Usually, the agrochemical mixture is made up with water, buffer, and/or further auxiliaries to the desired application concentration and the ready-to-use spray liquor or the agrochemical mixture according to the invention is thus obtained. Usually, 20 to 2000 liters, preferably 50 to 400 liters, of the ready-to-use spray liquor are applied per hectare of agricultural useful area.

The inventive mixtures provide excellent pre-plant burn-down, pre- and post-emergence control of weeds in cotton, including cotton plants that are tolerant to herbicides including glufosinate.

Thus, in the methods and uses of the invention, the compounds present in the inventive mixtures can be applied for pre-plant burn-down (to control emerged weeds prior to planting), pre-emergence (before the emergence of undesirable vegetation) or post-emergence (i.e., during and/or after emergence of the undesirable vegetation).

Thus, the invention relates to a method of an inventive mixture for controlling undesirable vegetation in cotton, including cotton plants that are tolerant to herbicides including glufosinate, which comprises applying the compounds present in the inventive mixtures to a locus of planted crops where undesirable vegetation occurs or might occur. The application is done before the emergence of undesirable vegetation or during and/or after emergence of the undesirable vegetation.

The application can be done after seeding of the cotton plants or during and/or after emergence of the cotton plants.

The term "locus", as used herein, means the area in which the vegetation or plants are growing or will grow, typically a field.

As used herein, the terms "controlling" and "combating" are synonyms.

As used herein, the terms "undesirable vegetation", "undesirable species", "undesirable plants", "harmful plants", "undesirable weeds", or "harmful weeds" are synonyms.

When using the inventive mixtures in the methods of the present invention, the active compounds present in the inventive mixtures can be applied simultaneously or in succession, where undesirable vegetation may occur. Herein, it is immaterial whether compounds present in the inventive mixtures are formulated jointly or separately and applied jointly or separately, and, in the case of separate application, in which order the application takes place. It is only necessary, that the compounds present in the inventive mixtures are applied in a time frame, which allows simultaneous action of the active ingredients on the undesirable plants.

In the above-mentioned methods of controlling weeds by application of the inventive mixtures, the inventive mixtures have an outstanding herbicidal activity against a broad spectrum of economically important monocotyledonous and dicotyledonous harmful plants. The inventive mixtures also act efficiently on perennial weeds which produce shoots from rhizomes, rootstocks or other perennial organs and which are difficult to control. In this context, it does not matter whether the compounds of the inventive mixtures are applied before sowing, pre-emergence or post-emergence. Pre-plant burn-down, post-emergence application, or early pre-sowing or pre-emergence application, are preferred.

Both L-glufosinate alone as well as, in the methods of the present invention, the inventive mixtures are suitable for controlling a large number of harmful plants in agricultural crops, including monocotyledonous weeds, in particular annual weeds such as gramineous weeds (grasses) including *Echinochloa* species such as barnyardgrass (*Echinochloa crusgalli* var. *crus-galli*), *Echinchloa walteri* (Pursh) Heller, jungle rice (*Echinochloa colona*), *Echinochloa crus-pavonis*, *Echinochloa oryzicola*, *Digitaria* species such as crabgrass (*Digitaria sanguinalis*), *Digitaria horizontalis*, sourgrass (*Digitaria insularis*) or naked crabgrass (*Digitaria nuda*), *Setaria* species such as green foxtail (*Setaria viridis*), giant foxtail (*Setaria faberii*), yellow foxtail (*Setaria glauca* or *Setaria pumila*) or *Setaria verticillata*, *Sorghum* species such as johnsongrass (*Sorghum halepense* Pers.), *Avena* species such as wild oats (*Avena fatua*), *Avena sterillis* or *Avena strigosa*, *Cenchrus* species such as *Cenchrus* species such as field sandbur (*Cenchrus pauciflorus*) or *Cenchrus echinatus*, *Bromus* species such as *Bromus japonicus* Thunb, *Bromus sterilis* or *Bromus tectorum*, *Lolium* species, *Phalaris* species such as *Phalaris brachystachys*, *Phalaris minor* or *Phalaris persicaria*, *Eriochloa* species, *Panicum* species such as fall *panicum* (*Panicum dichotomiflorum*), *Panicum fasciculatum* or *Panicum maximum*, *Brachiaria* species, annual bluegrass (*Poa annua*), *Alopecurus* species such as blackgrass (*Alopecurus myosuroides*), *Alopecurus aequalis* Sobol or *Alopecurus japonicus* Steud, *Aegilops* species such as *Aegilops cylindrica* or *Aegylops tauschii*, *Apera spica-venti*, *Eleusine indica*, *Cynodon dactylon*, couch grass (*Agropyron repens* or *Elymus repens*), *Agrostis alba*, *Beckmannia syzigachne* (Steud.) Fernald, *Chloris* species such as *Chloris virgata*, *Commelina* species such as *Commelina benghalensis*, *Commelina communis*, *Commelina diffusa* or *Commelina erecta*, *Dactyloctenium aegyptium*, *Hordeum jubatum*, *Hordeum leporinum*, *Imperata cylindrica*, *Ischaemum rogusum*, *Ixophorus unisetus*, *Leerisa hexandra*, *Leersia japonica*, *Leptochloa* species such as *Leptochloa chinensis*, *Leptochloa fascicularis*, *Leptochloa filiformis* or *Leptochloa panicoides*, *Lolium* species such as *Lolium multiflorum*, *Lolium perenne*, *Lolium persicum* or rigid ryegrass (*Lolium rigidum*), *Luziola subintegra*, *Murdannia nudiflora* (L.) Brenan, *Oryza latifolia*, *Oryza rufipogon*, *Paspalum distichum*, *Paspalum* species, *Pennisetum americanum*, *Pennisetum purpureum*, *Phleum paniculatum*, *Phragmites australia*, *Ploypogon fugax*. N., *Poa* species such as *Poa annua* or *Poa trivialis* L., *Puccinellia distans*, *Rottboellia cochinchinensis*, *Sclerochloa kengiana* (Ohwi) Tzvel., *Trichloris crinita*, *Urochloa* or *Brachiaria* species such as *Brachiaria decumbens*, *Brachiaria plantaginea*, *Brachiaria platyphylla*, *Urochloa panicoides*, *Urochloa ramosa* and the like.

Both L-glufosinate alone as well as the inventive mixtures are also suitable for controlling a large number of dicotyledonous weeds, in particular broad leaf weeds including *Polygonum* species such as wild buckwheat (*Polygonum convolvolus*), *Polygonum pensilvanicum*, *Polygonum persicaria* or prostrate knotweed (*Polygonum aviculare*), *Amaranthus* species such as pigweed (*Amaranthus retroflexus*), Palmer amaranth (*Amaranthus palmeri*), tall waterhemp (*Amaranthus tuberculatus* or *Amaranthus rudis*), redroot pigweed (*Amaranthus retroflexus*), green amaranth (*Amaranthus hybridus*), purple amaranth (*Amaranthus lividus*), prickly amaranth (*Amaranthus spinosus*) or *Amaranthus quitensis*, *Chenopodium* species such as common lambsquarters (*Chenopodium album* L.), *Chenopodium serotinum* or *Quinoa* (*Chenopodium quinoa*), *Sida* species such as prickly *Sida* (*Sida spinosa* L.), *Ambrosia* species such as common ragweed (*Ambrosia artemisiifolia*) or giant ragweed (*Ambrosia trifida*), *Acanthospermum* species, *Anthemis* species such as *Anthemis arvensis* or *Anthemis cotula*, *Atriplex* species, *Cirsium* species such as *Cirsium arvense*, *Convolvulus* species such as field bindweed (*Convolvulus arvensis*), *Conyza* species such as horseweed (*Conyza canadensis*, *Erigeron canadensis*) or hairy fleabane (*Conyza bonariensis*, *Erigeron bonariensis*), *Cassia* species, *Datura* species such as jimsonweed (*Datura stramonium*), *Euphorbia* species such as toothed spurge (*Euphorbia dentata*), *Euphorbia hirta*, *Euphorbia helioscopia* or fireplant (*Euphorbia heterophylla*), *Geranium* species such as *Geranium donianum* or *Geranium pusillum*, *Galinsoga* species, morningglory (*Ipomoea* species), *Lamium* species such as henbit dead-nettle (*Lamium amplexicaule*), *Malva* species such as dwarf mallow (*Malva neglecta*) or cheeseweed (*Malwa parviflora*), *Matricaria* species such as chamomile (*Matricaria chamomilla*) or *Matricaria inodora*, *Sysimbrium* species, *Solanum* species such as black nightshade (*Solanum nigrum*), *Xanthium* species, *Veronica* species such as *Veronica polita*, *Viola* species, common chickweed (*Stellaria media*), velvetleaf (*Abutilon theophrasti*), *Sesbania* species such as *Sesbania exaltata*, *Sesbania herbacea* or hemp *Sesbania* (*Sesbania exaltata* Cory), *Anoda cristata*, *Bidens* species such as *Bidens frondosa* or *Bidens pilosa*, *Brassica kaber*, *Capsella* species such as *Capsella* media or *Capsella bursa-pastoris*, *Centaurea cyanus*, *Galeopsis tetrahit*, *Galium aparine*, *Helianthus annuus*, *Desmodium tortuosum*, *Kochia scoparia*, *Mercurialis annua*, *Myosotis arvensis*, *Papaver rhoeas*, *Raphanus* species such as wild radish (*Raphanus raphanistrum*), *Salsola* species such as *Salsola tragus* or *Salsola kali*, *Sinapis arvensis*, *Sonchus* species such as *Sonchus asper*, *Sonchus arvensis* or *Sonchus oleraceus*, *Thlaspi arvense*, *Tagetes minuta*, *Richardia* species such as *Richardia scabra* or *Richardia brasiliensis*, *Aeschynomeme* species such as *Aeschynomene denticulata*, *Aeschynomene indica* or *Aeschynomene rudis*, *Alisma* species such as *Alisma canaliculatum* or *Alisma plantagoaquatica*, *Borreria* species such as *Borreria verticillata*, *Brassica rapa*, *Carduus acanthoides*, *Parietaria debilis*, *Portulaca oleracea*, *Ipomoea* species such as *Ipomoea grandifolia*, *Ipomoea hederacea*, *Ipomoea indivisa*, *Ipomoea lacunose*, *Ipomoea lonchophylla* or *Ipomoea wrightii*, *Senna obtusifolia*, *Sida* species such as arrowleaf *sida* (*Sida rhombifolia*) or prickly *sida* (*Sida spinosa*), *Spermacoce latifolia*, *Tridax procumbens*, *Trianthema portulacastrum*, *Parthenium hysterophorus*, *Portulaca oleracea*, *Acalypha australis*, *Ammi majus*, *Atriplex* species, *Orobanche* species, *Mercurialis annua*, *Cirsium arvense*, *Calystegia sepium*, *Stellaria media*, *Lamium* species, *Viola* species, *Celosia argentea*, *Melampodium divaricatum*, *Cleome viscosa*, *Molugo verticilatus*, *Borhevia erecta*, *Gomphrena* species, *Nicandra physalodes*, *Ricinus communis*, *Geranium dissectum*, *Alternanthera* species such as *Althernanthera philoxeroides* or *Alternanthera tenella*, *Ammannia* species such as *Ammania coccinea*, *Anacamtodon fortunei* Mitt., *Anagallis arvensis*, *Aneilema keisak*, *Arenaria serpyllifolia*, *Argemone mexicana*, *Asphodelus tenuifolius*, *Atriplex patula*, *Bacopa rotundifolia*, *Brassica napus*, *Caperonia* species such as *Caperonia castaneifolia* or *Caperonia palustris*, *Cephalanoplos segetum*, *Corynopus didymus*, *Crepis capillaris*, *Crepis tectorum*, *Croton lobatus*, *Descuminia sophia* (L.), *Descurainia pinnata*, *Echinodorus grandiflorus*, *Eclipta alba*, *Eclipta prostrata*, *Eichhornia crassipes*, *Eleocharis* species, *Equisetum arvense*, *Fallopia convolvulus*, *Fallopia convolvulus*, *Heteranthera limosa*, *Jussiaea* species, *Kallstroemia maxima*, *Lactuca serriola*, *Lathyrus aphaca*, *Launea mudicaulis*, *Leucas chinensis*, *Limnocharis flava*, *Lindernia dubia*, *Lindernia pyxidaria*, *Litospermum arvense*, *Ludwigia* species such as *Ludwigia octovallis*, *Macroptilium lathyroides*, *Malachium aquaticum* (L.), *Melilotus* species, *Merremia aegyptia*, *Momordica charantia*, *Monochoria hastate*, *Monochoria vaginalis*, *Mucuna* species, *Murdannia nudiflora*, *Oxalis neaei*, *Phylanthus* species, *Physalis* species,

*Pistia stratiotes, Potamogeton distinctus, Rorippa islandica, Rotala indica, Rotala ramosior, Rumex dentatus, Rumex obtusifolius, Sagittaria montevidensis, Sagittaria pygmaea* Miq., *Sagittaria sagittifolia, Sagittaria trifolia* L., *Senecio vulgaris, Sicyos polyacanthus, Silene gallica,* chenopo *Sisymbrium* species such as *Sisymbrium oficinale, Solanum* species, *Spergula arvensis, Sphenoclea zeylanica, Trianthema* spp., *Tripleurospermum inodorum, Veronica* species such as *Veronica persica* or *Veronica polita Vicia sativa* and the like.

Both L-glufosinate alone as well as the inventive mixtures are also suitable for controlling a large number of annual and perennial sedge weeds including *Cyperus* species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), *Cyperus difformis, Cyperus difformis* L., *Cyperus esculentus, Cyperus ferax, Cyperus flavus, Cyperus iria, Cyperus lanceolatus, Cyperus odoratus, Cyperus rotundus, Cyperus serotinus* Rottb., *Eleocharis acicularis, Eleocharis kuroguwai, Fimbristylis dichotoma, Fimbristylis miliacea, Scirpus grossus, Scirpus juncoides, Scirpus juncoides* Roxb, *Scirpus* or *Bolboschoenus maritimus, Scirpus* or *Schoenoplectus mucronatus, Scirpus planiculmis* Fr. Schmidt and the like.

Both L-glufosinate alone as well as the inventive mixtures are also suitable for controlling weeds that are resistant to commonly used herbicides such as, for example, weeds that are resistant to glyphosate, weeds that are resistant to auxin inhibitor herbicides such as e. g. 2,4-D or dicamba, weeds that are resistant to photosynthesis inhibitors such as e. g. atrazine, weeds that are resistant to ALS inhibitors such as e. g. sulfonylureas, imidazolinones or triazolopyrimidines, weeds that are resistant to ACCase inhibitors such as e. g. clodinafop, clethodim or pinoxaden or weeds that are resistant to protoporphyrinogen-IX-oxidase inhibitors such as e. g. sulfentrazone, flumioxazine, fomesafen or acifluorfen, for example the weeds that are listed in the International Survey of Resistant Weeds (http://www.weedscience.org/Summary/SpeciesbySOATable.aspx). In particular, they are suitable for controlling the resistant weeds that are listed in the International Survey of Resistant Weeds, for example ACCase resistant *Echinochloa crus-galli, Avena fatua, Alopecurus myosuroides, Echinochloa colona, Alopecurus japonicus, Bromus tectorum, Hordeum murinum, Ischaemum rugosum, Setaria viridis, Sorghum halepense, Alopecurus aequalis, Apera spicaventi, Avena sterilis, Beckmannia szygachne, Bromus diandrus, Digitaria sanguinalis, Echinocloa oryzoides, Echinochloa phyllopogon, Phalaris minor, Phalaris paradoxa, Setaria faberi, Setaria viridis, Brachypodium distachyon, Bromus diandrus, Bromus sterilis, Cynosurus echinatus, Digitaria insularis, Digitaria ischaemum, Leptochloa chinensis, Phalaris brachystachis, Rotboellia cochinchinensis, Digitaria ciliaris, Ehrharta longiflora, Eriochloa punctata, Leptochloa panicoides, Lolium persicum, Polypogon fugax, Sclerochloa kengiana, Snowdenia polystacha, Sorghum sudanese* and *Brachiaria plantaginea,* ALS inhibitor resistant *Echinochloa crus-galli, Poa annua, Avena fatua, Alopecurus myosuroides, Echinochloa colona, Amaranthus hybridus, Amaranthus palmeri, Amaranthus rudis, Conyza sumatrensis, Amaranthus retroflexus, Ambrosia artemisifolia, Conyza canadensis, Kochia scoparia, Raphanus raphanistrum, Senecio vernalis, Alopecurus japonicus, Bidens pilosa, Bromus tectorum, Chenopodium album, Conyza bonariensis, Hordeum murinum, Ischaemum rugosum, Senecio vulgaris, Setaria viridis, Sisymbrium orientale, Sorghum halepense, Alopecurus aequalis, Amaranthus blitum, Amaranthus powellii, Apera spicaventi, Avena sterilis, Brassica rapa, Bromus diandrus, Descurainia sophia, Digitaria sanguinalis, Echinochloa oryzoides, Echinochloa phyllopogon, Euphorbia heterophylla, Lactuca serriola, Phalaris minor, Phalaris paradoxa, Setaria faberi, Setaria viridis, Sinapis arvensis, Solanum ptycanthum, Sonchus oleraceus, Stellaria media, Amaranthus blitoides, Amaranthus spinosus, Amaranthus viridis, Ambrosia trifida, Bidens subalternans, Bromus diandrus, Bromus sterilis, Capsella bursa-pastoris, Centaurea cyanus, Cynosurus echinatus, Cyperus difformis, Fimbristilis miliacea, Galeopsis tetrahit, Galium aparine, Galium spurium, Helianthus annuus, Hirschfeldia incana, Limnocharis flava, Limnophila erecta, Papaver rhoeas, Parthenium hysterophorus, Phalaris brachystachis, Polygonum convolvulus, Polygonum lapathifolium, Polygonum persicaria, Ranunculus acris, Rottboellia cochinchinensis, Sagittaria montevidensis, Salsola tragus, Schoenoplectus mucronatus, Setaria pumila, Sonchus asper, Xanthium strumarium, Ageratum conyzoides, Alisma canaliculatum, Alisma plantago-aquatica, Ammannia auriculata, Ammannia coccinea, Ammannia arvensis, Anthemis cotula, Bacopa rotundifolia, Bifora radians, Blyxa aubertii, Brassica tournefortii, Bromus japonicus, Bromus secalinus, Lithospermum arvense, Camelina microcarpa, Chamaesyce maculata, Chrysanthemum coronarium, Clidemia hirta, Crepis tectorum, Cuscuta pentagona, Cyperus brevifolis, Cyperus compressus, Cyperus esculentus, Cyperus iria, Cyperus odoratus, Damasonium minus, Diplotaxis erucoides, Diplotaxis tenuifolia, Dopatrum junceum, Echium plantagineum, Elatine triandra, Eleocharis acicularis, Erucaria hispanica, Erysimum repandum, Galium tricornutum, Iva xanthifolia, Ixophorus unisetus, Lamium amplexicaule, Limnophilia sessiliflora, Lindernia dubia, Lindernia micrantha, Lindernia procumbens, Ludwigia prostrata, Matricaria recutita, Mesembryanthemum crystallinum, Monochoria korsakowii, Monochoria vaginalis, Myosoton aquaticum, Neslia paniculata, Oryza sativa* var. *sylvatica, Pentzia suffruticosa, Picris hieracioides, Raphanus sativus, Rapistrum rugosum, Rorippa indica, Rotala indica, Rotala pusilla, Rumex dentatus, Sagittaria guayensis, Sagittaria pygmaea, Sagittaria trifolia, Schoenoplectus fluviatilis, Schoenoplectus juncoides, Schoenoplectus wallichii, Sida spinosa, Silene gallica, Sinapis alba, Sisymbrium thellungii, Sorghum bicolor, Spergula arvensis, Thlaspi arvense, Tripleurospermum perforatum, Vaccaria hispanica* and *Vicia sativa,* photosynthesis inhibitor resistant *Echinochloa crus-galli, Poa annua, Alopecurus myosuroides, Echinochloa colona, Amaranthus hybridus, Amaranthus palmeri, Amaranthus rudis, Conyza sumatrensis, Amaranthus retroflexus, Ambrosia artemisifolia, Conyza canadensis, Kochia scoparia, Raphanus raphanistrum, Senecio vernalis, Alopecurus japonicus, Bidens pilosa, Bromus tectorum, Chenopodium album, Conyza bonariensis, Ischaemum rugosum, Senecio vulgaris, Setaria viridis, Sisymbrium orientale, Amaranthus blitum, Amaranthus powellii, Apera spicaventi, Beckmannia syzigachne, Brassica rapa, Digitaria sanguinalis, Euphorbia heterophylla, Phalaris minor, Phalaris paradoxa, Setaria faberi, Setaria viridis, Sinapis arvensis, Solanum ptycanthum, Stellaria media, Amaranthus blitoides, Amaranthus viridis, Bidens subalternans, Brachypodium distachyon, Capsella bursa-pastoris, Chloris barbata, Cyperus difformis, Echinochloa erecta, Epilobium ciliatum, Polygonum aviculare, Polygonum convolvulus, Polygonum lapathifolium, Polygonum persicaria, Portulaca oleracea, Schoenoplectus mucronatus, Setaria pumila, Solanum nigrum, Sonchus asper, Urochloa panicoides, Vulpia*

*bromoides, Abutilon theophrasti, Amaranthus albus, Amaranthus cruentus, Arabidopsis thaliana, Arenaria serpyllifolia, Bidens tripartita, Chenopodium album, Chenopodium ficifolium, Chenopodium polyspermum, Crypsis schoenoides, Datura stramonium, Epilobium tetragonum, Galinsoga ciliata, Matricaria discoidea, Panicum capillare, Panicum dichotomiflorum, Plantago lagopus, Polygonum hydopiper, Polygonum pensylvanicum, Polygonum monspeliensis, Rostraria, smyrnacea, Rumex acetosella, Setaria verticillata* and *Urtica urens*, PS-1-electron diversion inhibitor resistant *Poa annua, Conyza sumatrensis, Conyza canadensis, Alopecurus japonicus, Bidens pilosa, Conyza bonariensis, Hordeum murinum, Ischaemum rugosum, Amaranthus blitum, Solanum ptycanthum, Arctotheca calendula, Epilobium ciliatum, Hedyotis verticillata, Solanum nigrum, Vulpia bromoides, Convolvulus arvensis, Crassocephalum crepidioides, Cuphea carthagensis, Erigeron philadelphicus, Gamochaeta pensylvanica, Landoltia punctata, Lepidium virginicum, Mazus fauriei, Mazus pumilus, Mitracarpus hirtus, Sclerochloa dura, Solanum americanum* and *Youngia japonica*, glyphosate resistant *Poa annua, Echinochloa colona, Amaranthus hybridus, Amaranthus palmeri, Amaranthus rudis, Conyza sumatrensis, Ambrosia artemisifolia, Conyza canadensis, Kochia scoparia, Raphanus raphanistrum, Bidens pilosa, Conyza bonariensis, Hordeum murinum, Sorghum halepense, Brassica rapa, Bromus diandrus, Lactuca serriola, Sonchus oleraceus, Amaranthus spinosus, Ambrosia trifida, Digitaria insularis, Hedyotis verticillata, Helianthus annuus, Parthenium hysterophorus, Plantago lanceolata, Salsola tragus, Urochloa panicoides, Brachiaria eruciformis, Bromus rubens, Chloris elata, Chloris truncata, Chloris virgata, Cynodon hirsutus, Lactuca saligna, Leptochloa virgata, Paspalum paniculatum* and *Tridax procumbens*, microtubule assembly inhibitor resistant *Echinochloa crusgalli, Poa annua, Avena fatua, Alopecurus myosuroides, Amaranthus palmeri, Setaria viridis, Sorghum halepense, Alopecurus aequalis, Beckmannia syzigachne* and *Fumaria densifloria*, auxin herbicide resistant *Echinochloa crus-galli, Echinochloa colona, Amaranthus hybridus, Amaranthus rudis, Conyza sumatrensis, Kochia scoparia, Raphanus raphanistrum, Chenopodim album, Sisymbrium orientale, Descurainia sophia, Lactuca serriola, Sinapis arvensis, Sonchus oleraceus, Stellaria media, Arctotheca calendula, Centaurea cyanus, Digitaria ischaemum, Fimbristylis miliacea, Galeopsis tetrahit, Galium aparine, Galium spurium, Hirschfeldia incana, Limnocharis flava, Limnocharis erecta, Papaver rhoeas, Plantago lanceolata, Ranunculus acris, Carduus nutans, Carduus pycnocephalus, Centaurea soltitialis, Centaurea stoebe* ssp. *Micranthos, Cirsium arvense, Commelina diffusa, Echinochloa crus-pavonis, Soliva sessilis* and *Sphenoclea zeylanica*, HPPD inhibitor resistant *Amaranthus palmeri* and *Amaranthus rudis*, PPO inhibitor resistant *Acalypha australis, Amaranthus hybridus, Amaranthus palmeri, Amaranthus retroflexus, Amaranthus rudis, Ambrosia artemisifolia, Avena fatua, Conyza sumatrensis, Descurainia sophia, Euphorbia heterophylla* and *Senecio vernalis*, carotenoid biosynthesis inhibitor resistant *Hydrilla verticillata, Raphanus raphanistrum, Senecio vernalis* and *Sisymbrium orientale*, VLCFA inhibitor resistant *Alopecurus myosuroides, Avena fatua* and *Echinochloa crus-galli*.

If the compounds of the inventive mixtures are applied to the soil surface before germination, then the weed seedlings are either prevented completely from emerging, or the weeds grow until they have reached the cotyledon stage but then their growth stops, and, eventually, after three to four weeks have elapsed, they die completely.

If the active compounds of the inventive mixtures are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the cotton plants, is eliminated at a very early point in time and in a sustained manner.

When the active compounds of the inventive mixtures are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and weed grasses to be controlled, the herbicidal effect to take place more rapidly, the duration of action to be longer, the harmful plants to be controlled better while using only one, or few, applications, and the application period which is possible to be extended. In some cases, uptake of the compositions also reduces the amount of harmful constituents in the crop plant, such as nitrogen or oleic acid.

The active compounds of the inventive mixtures can be used jointly or in succession. They can also conveniently be combined with further herbicide treatments to treatment combinations that ensure a more complete or long-lasting weed control, or to ensure control of weeds that are resistant against certain herbicides through combined action of multiple herbicides with different modes of action. In particular, the active compounds of the inventive mixtures and further herbicides can be used in any of the treatment combinations outlined below that consist of pre-plant burn down, pre-emergence, post-emergence and pre-harvest desiccation/defoliation treatments. These treatment combinations can be particularly suitable if the cotton crop is tolerant to the action of one or more herbicides present in the treatment combination, including tolerance that is a result of breeding and/or genetic modification. Such tolerant plants include glufosinate tolerant cotton, glyphosate tolerant cotton and cotton that is tolerant to HPPD herbicides (e. g. isoxaflutole, topramezone, mesotrione, tembotrione, bicyclopyrone), auxin herbicides (e. g. 2,4-D, dicamba) and/or PPO herbicides (e. g. carfentrazone-ethyl, saflufenacil, sulfentrazone, trifludimoxazin, pyraflufen-ethyl, oxyfluorfen). For post-emergence treatments, it is also possible to avoid direct contact between the herbicide spray solution and the cotton crop by means of shielding or directed spray; this can be particularly suitable for, amongst others, L-glufosinate and herbicides that are PSI inhibitors (e. g. fluometuron, thidiazuron, diuron), ALS inhibitors (e. g. pyrithiobac sodium) or PPO inhibitors (e. g. carfentrazone-ethyl, saflufenacil, sulfentrazone, trifludimoxazin, sulfentrazone, pyraflufen-ethyl, oxyfluorfen).

The following active compounds of the inventive mixtures and further herbicides are particularly suitable as pre-plant burn-down weed control components in such treatment combinations: L-Glufosinate, L-glufosinate ammonium, L-glufosinate sodium, glyphosate, glyphosate dimethylammonium, glyphosate potassium, glyphosate isopropylammonium, paraquat, trifludimoxazin, saflufenacil, 2,4-D, 2,4-D choline salt, dicamba, dicamba ethanolamine salt, dicamba diglycolamine salt, dicamba potassium and dicamba BAPMA salt (i. e. dicamba N,N-bis(3-aminopropyl)methylamine salt).

The following active compounds of the inventive mixtures and further herbicides are particularly suitable as pre-emergence weed control components in such treatment combinations: Prometryne, fluometuron, thidiazuron, diuron, acetochlor, metolachlor, (S)-metolachlor, dimethenamid, dimethenamid-P, pyroxasulfone, clomazone, pendimethalin, trifluralin, fomesafen, oxyfluorfen, trifludimoxazin, saflufenacil, flumioxazin, sulfentrazone, isoxaflutole, bicyclopyrone, tembotrione and mesotrione.

The following active compounds of the inventive mixtures and further herbicides are particularly suitable as post-emergence weed control components in such treatment combinations: L-Glufosinate, L-glufosinate ammonium, L-glufosinate sodium, glyphosate, glyphosate dimethylammonium, glyphosate potassium, glyphosate isopropylammonium, pyrithiobac sodium, acetochlor, metolachlor, (S)-metolachlor, dimethenamid, dimethenamid-P, pyroxasulfone, isoxaflutole, topramezone, bicyclopyrone, tembotrione, mesotrione, fenquinotrione, tolpyralate, carfentrazone-ethyl, saflufenacil, sulfentrazone, trifludimoxazin, pyraflufen-ethyl, fluthiacet-methyl, oxyfluorfen, fomesafen, clethodim, cycloxydim, sethoxydim, tepraloxydim, 2,4-D, 2,4-D choline salt, dicamba, dicamba sodium, dicamba ethanolamine salt, dicamba diglycolamine salt, dicamba potassium and dicamba BAPMA salt.

The following active compounds of the inventive mixtures and further herbicides are particularly suitable as pre-harvest desiccation/defoliation components in such treatment combinations: ethephon, cyclanilide, thidiazuron, diuron, tribufos, carfentrazone-ethyl, saflufenacil, trifludimoxazin, pyraflufen-ethyl, flumiclorac-pentyl, fluthiacet-methyl.

Particularly suitable treatment combinations of active compounds of the inventive mixtures and further herbicides are:

The treatment combinations 1.1 to 1.799 in which one of the treatment combinations listed in the following table is combined with post-emergence use of L-glufosinate.

| Treatment combination | Pre-plant burn-down | Pre-emergence | Pre-harvest desiccation/ defoliation |
|---|---|---|---|
| 1 | L-Glufosinate | Prometryn | — |
| 2 | L-Glufosinate | Fluometuron | — |
| 3 | L-Glufosinate | Thidiazuron | — |
| 4 | L-Glufosinate | Diuron | — |
| 5 | L-Glufosinate | Acetochlor | — |
| 6 | L-Glufosinate | Metolachlor | — |
| 7 | L-Glufosinate | (S)-Metolachlor | — |
| 8 | L-Glufosinate | Dimethenamid | — |
| 9 | L-Glufosinate | Dimethenamid-P | — |
| 10 | L-Glufosinate | Pyroxasulfone | — |
| 11 | L-Glufosinate | Clomazone | — |
| 12 | L-Glufosinate | Pendimethalin | — |
| 13 | L-Glufosinate | Trifluralin | — |
| 14 | L-Glufosinate | Fomesafen | — |
| 15 | L-Glufosinate | Oxyfluorfen | — |
| 16 | L-Glufosinate | Flumioxazin | — |
| 17 | L-Glufosinate | Sulfentrazone | — |
| 18 | L-Glufosinate | Trifludimoxazin | — |
| 19 | L-Glufosinate | Saflufenacil | — |
| 20 | L-Glufosinate | Saflufenacil + trifludimoxazin | — |
| 21 | L-Glufosinate | Isoxaflutole | — |
| 22 | L-Glufosinate | Bicyclopyrone | — |
| 23 | L-Glufosinate | Tembotrione | — |
| 24 | L-Glufosinate | Mesotrione | — |
| 25 | L-Glufosinate ammonium | Prometryn | — |
| 26 | L-Glufosinate ammonium | Fluometuron | — |
| 27 | L-Glufosinate ammonium | Thidiazuron | — |
| 28 | L-Glufosinate ammonium | Diuron | — |
| 29 | L-Glufosinate ammonium | Acetochlor | — |
| 30 | L-Glufosinate ammonium | Metolachlor | — |
| 31 | L-Glufosinate ammonium | (S)-Metolachlor | — |
| 32 | L-Glufosinate ammonium | Dimethenamid | — |
| 33 | L-Glufosinate ammonium | Dimethenamid-P | — |
| 34 | L-Glufosinate ammonium | Pyroxasulfone | — |
| 35 | L-Glufosinate ammonium | Clomazone | — |
| 36 | L-Glufosinate ammonium | Pendimethalin | — |
| 37 | L-Glufosinate ammonium | Trifluralin | — |
| 38 | L-Glufosinate ammonium | Fomesafen | — |
| 39 | L-Glufosinate ammonium | Oxyfluorfen | — |
| 40 | L-Glufosinate ammonium | Flumioxazin | — |
| 41 | L-Glufosinate ammonium | Sulfentrazone | — |
| 42 | L-Glufosinate ammonium | Trifludimoxazin | — |
| 43 | L-Glufosinate ammonium | Saflufenacil | — |
| 44 | L-Glufosinate ammonium | Saflufenacil + trifludimoxazin | — |
| 45 | L-Glufosinate ammonium | Isoxaflutole | — |
| 46 | L-Glufosinate ammonium | Bicyclopyrone | — |
| 47 | L-Glufosinate ammonium | Tembotrione | — |
| 48 | L-Glufosinate ammonium | Mesotrione | — |
| 49 | L-Glufosinate sodium | Prometryn | — |
| 50 | L-Glufosinate sodium | Fluometuron | — |
| 51 | L-Glufosinate sodium | Thidiazuron | — |
| 52 | L-Glufosinate sodium | Diuron | — |
| 53 | L-Glufosinate sodium | Acetochlor | — |
| 54 | L-Glufosinate sodium | Metolachlor | — |

-continued

| Treatment combination | Pre-plant burn-down | Pre-emergence | Pre-harvest desiccation/defoliation |
|---|---|---|---|
| 55 | L-Glufosinate sodium | (S)-Metolachlor | — |
| 56 | L-Glufosinate sodium | Dimethenamid | — |
| 57 | L-Glufosinate sodium | Dimethenamid-P | — |
| 58 | L-Glufosinate sodium | Pyroxasulfone | — |
| 59 | L-Glufosinate sodium | Clomazone | — |
| 60 | L-Glufosinate sodium | Pendimethalin | — |
| 61 | L-Glufosinate sodium | Trifluralin | — |
| 62 | L-Glufosinate sodium | Fomesafen | — |
| 63 | L-Glufosinate sodium | Oxyfluorfen | — |
| 64 | L-Glufosinate sodium | Flumioxazin | — |
| 65 | L-Glufosinate sodium | Sulfentrazone | — |
| 66 | L-Glufosinate sodium | Trifludimoxazin | — |
| 67 | L-Glufosinate sodium | Saflufenacil | — |
| 68 | L-Glufosinate sodium | Saflufenacil + trifludimoxazin | — |
| 69 | L-Glufosinate sodium | Isoxaflutole | — |
| 70 | L-Glufosinate sodium | Bicyclopyrone | — |
| 71 | L-Glufosinate sodium | Tembotrione | — |
| 72 | L-Glufosinate sodium | Mesotrione | — |
| 73 | Glyphosate | Prometryn | — |
| 74 | Glyphosate | Fluometuron | — |
| 75 | Glyphosate | Thidiazuron | — |
| 76 | Glyphosate | Diuron | — |
| 77 | Glyphosate | Acetochlor | — |
| 78 | Glyphosate | Metolachlor | — |
| 79 | Glyphosate | (S)-Metolachlor | — |
| 80 | Glyphosate | Dimethenamid | — |
| 81 | Glyphosate | Dimethenamid-P | — |
| 82 | Glyphosate | Pyroxasulfone | — |
| 83 | Glyphosate | Clomazone | — |
| 84 | Glyphosate | Pendimethalin | — |
| 85 | Glyphosate | Trifluralin | — |
| 86 | Glyphosate | Fomesafen | — |
| 87 | Glyphosate | Oxyfluorfen | — |
| 88 | Glyphosate | Flumioxazin | — |
| 89 | Glyphosate | Sulfentrazone | — |
| 90 | Glyphosate | Trifludimoxazin | — |
| 91 | Glyphosate | Saflufenacil | — |
| 92 | Glyphosate | Saflufenacil + trifludimoxazin | — |
| 93 | Glyphosate | Isoxaflutole | — |
| 94 | Glyphosate | Bicyclopyrone | — |
| 95 | Glyphosate | Tembotrione | — |
| 96 | Glyphosate | Mesotrione | — |
| 97 | Glyphosate dimethylammonium | Prometryn | — |
| 98 | Glyphosate dimethylammonium | Fluometuron | — |
| 99 | Glyphosate dimethylammonium | Thidiazuron | — |
| 100 | Glyphosate dimethylammonium | Diuron | — |
| 101 | Glyphosate dimethylammonium | Acetochlor | — |
| 102 | Glyphosate dimethylammonium | Metolachlor | — |
| 103 | Glyphosate dimethylammonium | (S)-Metolachlor | — |
| 104 | Glyphosate dimethylammonium | Dimethenamid | — |
| 105 | Glyphosate dimethylammonium | Dimethenamid-P | — |
| 106 | Glyphosate dimethylammonium | Pyroxasulfone | — |
| 107 | Glyphosate dimethylammonium | Clomazone | — |
| 108 | Glyphosate dimethylammonium | Pendimethalin | — |
| 109 | Glyphosate dimethylammonium | Trifluralin | — |
| 110 | Glyphosate dimethylammonium | Fomesafen | — |
| 111 | Glyphosate dimethylammonium | Oxyfluorfen | — |
| 112 | Glyphosate dimethylammonium | Flumioxazin | — |
| 113 | Glyphosate dimethylammonium | Sulfentrazone | — |
| 114 | Glyphosate dimethylammonium | Trifludimoxazin | — |
| 115 | Glyphosate dimethylammonium | Saflufenacil | — |
| 116 | Glyphosate dimethylammonium | Saflufenacil + trifludimoxazin | — |
| 117 | Glyphosate dimethylammonium | Isoxaflutole | — |
| 118 | Glyphosate dimethylammonium | Bicyclopyrone | — |
| 119 | Glyphosate dimethylammonium | Tembotrione | — |
| 120 | Glyphosate dimethylammonium | Mesotrione | — |
| 121 | Glyphosate potassium | Prometryn | — |
| 122 | Glyphosate potassium | Fluometuron | — |
| 123 | Glyphosate potassium | Thidiazuron | — |
| 124 | Glyphosate potassium | Diuron | — |
| 125 | Glyphosate potassium | Acetochlor | — |
| 126 | Glyphosate potassium | Metolachlor | — |
| 127 | Glyphosate potassium | (S)-Metolachlor | — |
| 128 | Glyphosate potassium | Dimethenamid | — |
| 129 | Glyphosate potassium | Dimethenamid-P | — |

-continued

| Treatment combination | Pre-plant burn-down | Pre-emergence | Pre-harvest desiccation/ defoliation |
|---|---|---|---|
| 130 | Glyphosate potassium | Pyroxasulfone | — |
| 131 | Glyphosate potassium | Clomazone | — |
| 132 | Glyphosate potassium | Pendimethalin | — |
| 133 | Glyphosate potassium | Trifluralin | — |
| 134 | Glyphosate potassium | Fomesafen | — |
| 135 | Glyphosate potassium | Oxyfluorfen | — |
| 136 | Glyphosate potassium | Flumioxazin | — |
| 137 | Glyphosate potassium | Sulfentrazone | — |
| 138 | Glyphosate potassium | Trifludimoxazin | — |
| 139 | Glyphosate potassium | Saflufenacil | — |
| 140 | Glyphosate potassium | Saflufenacil + trifludimoxazin | — |
| 141 | Glyphosate potassium | Isoxaflutole | — |
| 142 | Glyphosate potassium | Bicyclopyrone | — |
| 143 | Glyphosate potassium | Tembotrione | — |
| 144 | Glyphosate potassium | Mesotrione | — |
| 145 | Glyphosate isopropylammonium | Prometryn | — |
| 146 | Glyphosate isopropylammonium | Fluometuron | — |
| 147 | Glyphosate isopropylammonium | Thidiazuron | — |
| 148 | Glyphosate isopropylammonium | Diuron | — |
| 149 | Glyphosate isopropylammonium | Acetochlor | — |
| 150 | Glyphosate isopropylammonium | Metolachlor | — |
| 151 | Glyphosate isopropylammonium | (S)-Metolachlor | — |
| 152 | Glyphosate isopropylammonium | Dimethenamid | — |
| 153 | Glyphosate isopropylammonium | Dimethenamid-P | — |
| 154 | Glyphosate isopropylammonium | Pyroxasulfone | — |
| 155 | Glyphosate isopropylammonium | Clomazone | — |
| 156 | Glyphosate isopropylammonium | Pendimethalin | — |
| 157 | Glyphosate isopropylammonium | Trifluralin | — |
| 158 | Glyphosate isopropylammonium | Fomesafen | — |
| 159 | Glyphosate isopropylammonium | Oxyfluorfen | — |
| 160 | Glyphosate isopropylammonium | Flumioxazin | — |
| 161 | Glyphosate isopropylammonium | Sulfentrazone | — |
| 162 | Glyphosate isopropylammonium | Trifludimoxazin | — |
| 163 | Glyphosate isopropylammonium | Saflufenacil | — |
| 164 | Glyphosate isopropylammonium | Saflufenacil + trifludimoxazin | — |
| 165 | Glyphosate isopropylammonium | Isoxaflutole | — |
| 166 | Glyphosate isopropylammonium | Bicyclopyrone | — |
| 167 | Glyphosate isopropylammonium | Tembotrione | — |
| 168 | Glyphosate isopropylammonium | Mesotrione | — |
| 169 | Saflufenacil | Prometryn | — |
| 170 | Saflufenacil | Fluometuron | — |
| 171 | Saflufenacil | Thidiazuron | — |
| 172 | Saflufenacil | Diuron | — |
| 173 | Saflufenacil | Acetochlor | — |
| 174 | Saflufenacil | Metolachlor | — |
| 175 | Saflufenacil | (S)-Metolachlor | — |
| 176 | Saflufenacil | Dimethenamid | — |
| 177 | Saflufenacil | Dimethenamid-P | — |
| 178 | Saflufenacil | Pyroxasulfone | — |
| 179 | Saflufenacil | Clomazone | — |
| 180 | Saflufenacil | Pendimethalin | — |
| 181 | Saflufenacil | Trifluralin | — |
| 182 | Saflufenacil | Fomesafen | — |
| 183 | Saflufenacil | Oxyfluorfen | — |
| 184 | Saflufenacil | Flumioxazin | — |
| 185 | Saflufenacil | Sulfentrazone | — |
| 186 | Saflufenacil | Trifludimoxazin | — |
| 187 | Saflufenacil | Saflufenacil | — |
| 188 | Saflufenacil | Saflufenacil + trifludimoxazin | — |
| 189 | Saflufenacil | Isoxaflutole | — |
| 190 | Saflufenacil | Bicyclopyrone | — |
| 191 | Saflufenacil | Tembotrione | — |
| 192 | Saflufenacil | Mesotrione | — |
| 193 | Trifludimoxazin | Prometryn | — |
| 194 | Trifludimoxazin | Fluometuron | — |
| 195 | Trifludimoxazin | Thidiazuron | — |
| 196 | Trifludimoxazin | Diuron | — |
| 197 | Trifludimoxazin | Acetochlor | — |
| 198 | Trifludimoxazin | Metolachlor | — |
| 199 | Trifludimoxazin | (S)-Metolachlor | — |
| 200 | Trifludimoxazin | Dimethenamid | — |
| 201 | Trifludimoxazin | Dimethenamid-P | — |
| 202 | Trifludimoxazin | Pyroxasulfone | — |
| 203 | Trifludimoxazin | Clomazone | — |
| 204 | Trifludimoxazin | Pendimethalin | — |

-continued

| Treatment combination | Pre-plant burn-down | Pre-emergence | Pre-harvest desiccation/defoliation |
|---|---|---|---|
| 205 | Trifludimoxazin | Trifluralin | — |
| 206 | Trifludimoxazin | Fomesafen | — |
| 207 | Trifludimoxazin | Oxyfluorfen | — |
| 208 | Trifludimoxazin | Flumioxazin | — |
| 209 | Trifludimoxazin | Sulfentrazone | — |
| 210 | Trifludimoxazin | Trifludimoxazin | — |
| 211 | Trifludimoxazin | Saflufenacil | — |
| 212 | Trifludimoxazin | Saflufenacil + trifludimoxazin | — |
| 213 | Trifludimoxazin | Isoxaflutole | — |
| 214 | Trifludimoxazin | Bicyclopyrone | — |
| 215 | Trifludimoxazin | Tembotrione | — |
| 216 | Trifludimoxazin | Mesotrione | — |
| 217 | Saflufenacil + trifludimoxazin | Prometryn | — |
| 218 | Saflufenacil + trifludimoxazin | Fluometuron | — |
| 219 | Saflufenacil + trifludimoxazin | Thidiazuron | — |
| 220 | Saflufenacil + trifludimoxazin | Diuron | — |
| 221 | Saflufenacil + trifludimoxazin | Acetochlor | — |
| 222 | Saflufenacil + trifludimoxazin | Metolachlor | — |
| 223 | Saflufenacil + trifludimoxazin | (S)-Metolachlor | — |
| 224 | Saflufenacil + trifludimoxazin | Dimethenamid | — |
| 225 | Saflufenacil + trifludimoxazin | Dimethenamid-P | — |
| 226 | Saflufenacil + trifludimoxazin | Pyroxasulfone | — |
| 227 | Saflufenacil + trifludimoxazin | Clomazone | — |
| 228 | Saflufenacil + trifludimoxazin | Pendimethalin | — |
| 229 | Saflufenacil + trifludimoxazin | Trifluralin | — |
| 230 | Saflufenacil + trifludimoxazin | Fomesafen | — |
| 231 | Saflufenacil + trifludimoxazin | Oxyfluorfen | — |
| 232 | Saflufenacil + trifludimoxazin | Flumioxazin | — |
| 233 | Saflufenacil + trifludimoxazin | Sulfentrazone | — |
| 234 | Saflufenacil + trifludimoxazin | Trifludimoxazin | — |
| 235 | Saflufenacil + trifludimoxazin | Saflufenacil | — |
| 236 | Saflufenacil + trifludimoxazin | Saflufenacil + trifludimoxazin | — |
| 237 | Saflufenacil + trifludimoxazin | Isoxaflutole | — |
| 238 | Saflufenacil + trifludimoxazin | Bicyclopyrone | — |
| 239 | Saflufenacil + trifludimoxazin | Tembotrione | — |
| 240 | Saflufenacil + trifludimoxazin | Mesotrione | — |
| 241 | Dicamba | Prometryn | — |
| 242 | Dicamba | Fluometuron | — |
| 243 | Dicamba | Thidiazuron | — |
| 244 | Dicamba | Diuron | — |
| 245 | Dicamba | Acetochlor | — |
| 246 | Dicamba | Metolachlor | — |
| 247 | Dicamba | (S)-Metolachlor | — |
| 248 | Dicamba | Dimethenamid | — |
| 249 | Dicamba | Dimethenamid-P | — |
| 250 | Dicamba | Pyroxasulfone | — |
| 251 | Dicamba | Clomazone | — |
| 252 | Dicamba | Pendimethalin | — |
| 253 | Dicamba | Trifluralin | — |
| 254 | Dicamba | Fomesafen | — |
| 255 | Dicamba | Oxyfluorfen | — |
| 256 | Dicamba | Flumioxazin | — |
| 257 | Dicamba | Sulfentrazone | — |
| 258 | Dicamba | Trifludimoxazin | — |
| 259 | Dicamba | Saflufenacil | — |
| 260 | Dicamba | Saflufenacil + trifludimoxazin | — |
| 261 | Dicamba | Isoxaflutole | — |
| 262 | Dicamba | Bicyclopyrone | — |
| 263 | Dicamba | Tembotrione | — |
| 264 | Dicamba | Mesotrione | — |
| 265 | Dicamba ethanolamine salt | Prometryn | — |
| 266 | Dicamba ethanolamine salt | Fluometuron | — |
| 267 | Dicamba ethanolamine salt | Thidiazuron | — |
| 268 | Dicamba ethanolamine salt | Diuron | — |
| 269 | Dicamba ethanolamine salt | Acetochlor | — |
| 270 | Dicamba ethanolamine salt | Metolachlor | — |
| 271 | Dicamba ethanolamine salt | (S)-Metolachlor | — |
| 272 | Dicamba ethanolamine salt | Dimethenamid | — |
| 273 | Dicamba ethanolamine salt | Dimethenamid-P | — |
| 274 | Dicamba ethanolamine salt | Pyroxasulfone | — |
| 275 | Dicamba ethanolamine salt | Clomazone | — |
| 276 | Dicamba ethanolamine salt | Pendimethalin | — |
| 277 | Dicamba ethanolamine salt | Trifluralin | — |
| 278 | Dicamba ethanolamine salt | Fomesafen | — |
| 279 | Dicamba ethanolamine salt | Oxyfluorfen | — |

-continued

| Treatment combination | Pre-plant burn-down | Pre-emergence | Pre-harvest desiccation/ defoliation |
|---|---|---|---|
| 280 | Dicamba ethanolamine salt | Flumioxazin | — |
| 281 | Dicamba ethanolamine salt | Sulfentrazone | — |
| 282 | Dicamba ethanolamine salt | Trifludimoxazin | — |
| 283 | Dicamba ethanolamine salt | Saflufenacil | — |
| 284 | Dicamba ethanolamine salt | Saflufenacil + trifludimoxazin | — |
| 285 | Dicamba ethanolamine salt | Isoxaflutole | — |
| 286 | Dicamba ethanolamine salt | Bicyclopyrone | — |
| 287 | Dicamba ethanolamine salt | Tembotrione | — |
| 288 | Dicamba ethanolamine salt | Mesotrione | — |
| 289 | Dicamba diglycolamine salt | Prometryn | — |
| 290 | Dicamba diglycolamine salt | Fluometuron | — |
| 291 | Dicamba diglycolamine salt | Thidiazuron | — |
| 292 | Dicamba diglycolamine salt | Diuron | — |
| 293 | Dicamba diglycolamine salt | Acetochlor | — |
| 294 | Dicamba diglycolamine salt | Metolachlor | — |
| 295 | Dicamba diglycolamine salt | (S)-Metolachlor | — |
| 296 | Dicamba diglycolamine salt | Dimethenamid | — |
| 297 | Dicamba diglycolamine salt | Dimethenamid-P | — |
| 298 | Dicamba diglycolamine salt | Pyroxasulfone | — |
| 299 | Dicamba diglycolamine salt | Clomazone | — |
| 300 | Dicamba diglycolamine salt | Pendimethalin | — |
| 301 | Dicamba diglycolamine salt | Trifluralin | — |
| 302 | Dicamba diglycolamine salt | Fomesafen | — |
| 303 | Dicamba diglycolamine salt | Oxyfluorfen | — |
| 304 | Dicamba diglycolamine salt | Flumioxazin | — |
| 305 | Dicamba diglycolamine salt | Sulfentrazone | — |
| 306 | Dicamba diglycolamine salt | Trifludimoxazin | — |
| 307 | Dicamba diglycolamine salt | Saflufenacil | — |
| 308 | Dicamba diglycolamine salt | Saflufenacil + trifludimoxazin | — |
| 309 | Dicamba diglycolamine salt | Isoxaflutole | — |
| 310 | Dicamba diglycolamine salt | Bicyclopyrone | — |
| 311 | Dicamba diglycolamine salt | Tembotrione | — |
| 312 | Dicamba diglycolamine salt | Mesotrione | — |
| 313 | Dicamba potassium | Prometryn | — |
| 314 | Dicamba potassium | Fluometuron | — |
| 315 | Dicamba potassium | Thidiazuron | — |
| 316 | Dicamba potassium | Diuron | — |
| 317 | Dicamba potassium | Acetochlor | — |
| 318 | Dicamba potassium | Metolachlor | — |
| 319 | Dicamba potassium | (S)-Metolachlor | — |
| 320 | Dicamba potassium | Dimethenamid | — |
| 321 | Dicamba potassium | Dimethenamid-P | — |
| 322 | Dicamba potassium | Pyroxasulfone | — |
| 323 | Dicamba potassium | Clomazone | — |
| 324 | Dicamba potassium | Pendimethalin | — |
| 325 | Dicamba potassium | Trifluralin | — |
| 326 | Dicamba potassium | Fomesafen | — |
| 327 | Dicamba potassium | Oxyfluorfen | — |
| 328 | Dicamba potassium | Flumioxazin | — |
| 329 | Dicamba potassium | Sulfentrazone | — |
| 330 | Dicamba potassium | Trifludimoxazin | — |
| 331 | Dicamba potassium | Saflufenacil | — |
| 332 | Dicamba potassium | Saflufenacil + trifludimoxazin | — |
| 333 | Dicamba potassium | Isoxaflutole | — |
| 334 | Dicamba potassium | Bicyclopyrone | — |
| 335 | Dicamba potassium | Tembotrione | — |
| 336 | Dicamba potassium | Mesotrione | — |
| 337 | Dicamba BAPMA salt | Prometryn | — |
| 338 | Dicamba BAPMA salt | Fluometuron | — |
| 339 | Dicamba BAPMA salt | Thidiazuron | — |
| 340 | Dicamba BAPMA salt | Diuron | — |
| 341 | Dicamba BAPMA salt | Acetochlor | — |
| 342 | Dicamba BAPMA salt | Metolachlor | — |
| 343 | Dicamba BAPMA salt | (S)-Metolachlor | — |
| 344 | Dicamba BAPMA salt | Dimethenamid | — |
| 345 | Dicamba BAPMA salt | Dimethenamid-P | — |
| 346 | Dicamba BAPMA salt | Pyroxasulfone | — |
| 347 | Dicamba BAPMA salt | Clomazone | — |
| 348 | Dicamba BAPMA salt | Pendimethalin | — |
| 349 | Dicamba BAPMA salt | Trifluralin | — |
| 350 | Dicamba BAPMA salt | Fomesafen | — |
| 351 | Dicamba BAPMA salt | Oxyfluorfen | — |
| 352 | Dicamba BAPMA salt | Flumioxazin | — |
| 353 | Dicamba BAPMA salt | Sulfentrazone | — |
| 354 | Dicamba BAPMA salt | Trifludimoxazin | — |

| Treatment combination | Pre-plant burn-down | Pre-emergence | Pre-harvest desiccation/defoliation |
|---|---|---|---|
| 355 | Dicamba BAPMA salt | Saflufenacil | — |
| 356 | Dicamba BAPMA salt | Saflufenacil + trifludimoxazin | — |
| 357 | Dicamba BAPMA salt | Isoxaflutole | — |
| 358 | Dicamba BAPMA salt | Bicyclopyrone | — |
| 359 | Dicamba BAPMA salt | Tembotrione | — |
| 360 | Dicamba BAPMA salt | Mesotrione | — |
| 361 | — | Prometryn | — |
| 362 | — | Fluometuron | — |
| 363 | — | Thidiazuron | — |
| 364 | — | Diuron | — |
| 365 | — | Acetochlor | — |
| 366 | — | Metolachlor | — |
| 367 | — | (S)-Metolachlor | — |
| 368 | — | Dimethenamid | — |
| 369 | — | Dimethenamid-P | — |
| 370 | — | Pyroxasulfone | — |
| 371 | — | Clomazone | — |
| 372 | — | Pendimethalin | — |
| 373 | — | Trifluralin | — |
| 374 | — | Fomesafen | — |
| 375 | — | Oxyfluorfen | — |
| 376 | — | Flumioxazin | — |
| 377 | — | Sulfentrazone | — |
| 378 | — | Trifludimoxazin | — |
| 379 | — | Saflufenacil | — |
| 380 | — | Saflufenacil + trifludimoxazin | — |
| 381 | — | Isoxaflutole | — |
| 382 | — | Bicyclopyrone | — |
| 383 | — | Tembotrione | — |
| 384 | — | Mesotrione | — |
| 385 | L-Glufosinate | — | — |
| 386 | L-Glufosinate ammonium | — | — |
| 387 | L-Glufosinate sodium | — | — |
| 388 | Glyphosate | — | — |
| 389 | Glyphosate dimethylammonium | — | — |
| 390 | Glyphosate potassium | — | — |
| 391 | Glyphosate isopropylammonium | — | — |
| 392 | Saflufenacil | — | — |
| 393 | Trifludimoxazin | — | — |
| 394 | Saflufenacil + trifludimoxazin | — | — |
| 395 | Dicamba | — | — |
| 396 | Dicamba ethanolamine salt | — | — |
| 397 | Dicamba diglycolamine salt | — | — |
| 398 | Dicamba potassium | — | — |
| 399 | Dicamba BAPMA salt | — | — |
| 400 | L-Glufosinate | Prometryn | Saflufenacil |
| 401 | L-Glufosinate | Fluometuron | Saflufenacil |
| 402 | L-Glufosinate | Thidiazuron | Saflufenacil |
| 403 | L-Glufosinate | Diuron | Saflufenacil |
| 404 | L-Glufosinate | Acetochlor | Saflufenacil |
| 405 | L-Glufosinate | Metolachlor | Saflufenacil |
| 406 | L-Glufosinate | (S)-Metolachlor | Saflufenacil |
| 407 | L-Glufosinate | Dimethenamid | Saflufenacil |
| 408 | L-Glufosinate | Dimethenamid-P | Saflufenacil |
| 409 | L-Glufosinate | Pyroxasulfone | Saflufenacil |
| 410 | L-Glufosinate | Clomazone | Saflufenacil |
| 411 | L-Glufosinate | Pendimethalin | Saflufenacil |
| 412 | L-Glufosinate | Trifluralin | Saflufenacil |
| 413 | L-Glufosinate | Fomesafen | Saflufenacil |
| 414 | L-Glufosinate | Oxyfluorfen | Saflufenacil |
| 415 | L-Glufosinate | Flumioxazin | Saflufenacil |
| 416 | L-Glufosinate | Sulfentrazone | Saflufenacil |
| 417 | L-Glufosinate | Trifludimoxazin | Saflufenacil |
| 418 | L-Glufosinate | Saflufenacil | Saflufenacil |
| 419 | L-Glufosinate | Saflufenacil + trifludimoxazin | Saflufenacil |
| 420 | L-Glufosinate | Isoxaflutole | Saflufenacil |
| 421 | L-Glufosinate | Bicyclopyrone | Saflufenacil |
| 422 | L-Glufosinate | Tembotrione | Saflufenacil |
| 423 | L-Glufosinate | Mesotrione | Saflufenacil |
| 424 | L-Glufosinate ammonium | Prometryn | Saflufenacil |
| 425 | L-Glufosinate ammonium | Fluometuron | Saflufenacil |
| 426 | L-Glufosinate ammonium | Thidiazuron | Saflufenacil |
| 427 | L-Glufosinate ammonium | Diuron | Saflufenacil |
| 428 | L-Glufosinate ammonium | Acetochlor | Saflufenacil |
| 429 | L-Glufosinate ammonium | Metolachlor | Saflufenacil |

-continued

| Treatment combination | Pre-plant burn-down | Pre-emergence | Pre-harvest desiccation/ defoliation |
|---|---|---|---|
| 430 | L-Glufosinate ammonium | (S)-Metolachlor | Saflufenacil |
| 431 | L-Glufosinate ammonium | Dimethenamid | Saflufenacil |
| 432 | L-Glufosinate ammonium | Dimethenamid-P | Saflufenacil |
| 433 | L-Glufosinate ammonium | Pyroxasulfone | Saflufenacil |
| 434 | L-Glufosinate ammonium | Clomazone | Saflufenacil |
| 435 | L-Glufosinate ammonium | Pendimethalin | Saflufenacil |
| 436 | L-Glufosinate ammonium | Trifluralin | Saflufenacil |
| 437 | L-Glufosinate ammonium | Fomesafen | Saflufenacil |
| 438 | L-Glufosinate ammonium | Oxyfluorfen | Saflufenacil |
| 439 | L-Glufosinate ammonium | Flumioxazin | Saflufenacil |
| 440 | L-Glufosinate ammonium | Sulfentrazone | Saflufenacil |
| 441 | L-Glufosinate ammonium | Trifludimoxazin | Saflufenacil |
| 442 | L-Glufosinate ammonium | Saflufenacil | Saflufenacil |
| 443 | L-Glufosinate ammonium | Saflufenacil + trifludimoxazin | Saflufenacil |
| 444 | L-Glufosinate ammonium | Isoxaflutole | Saflufenacil |
| 445 | L-Glufosinate ammonium | Bicyclopyrone | Saflufenacil |
| 446 | L-Glufosinate ammonium | Tembotrione | Saflufenacil |
| 447 | L-Glufosinate ammonium | Mesotrione | Saflufenacil |
| 448 | L-Glufosinate sodium | Prometryn | Saflufenacil |
| 449 | L-Glufosinate sodium | Fluometuron | Saflufenacil |
| 450 | L-Glufosinate sodium | Thidiazuron | Saflufenacil |
| 451 | L-Glufosinate sodium | Diuron | Saflufenacil |
| 452 | L-Glufosinate sodium | Acetochlor | Saflufenacil |
| 453 | L-Glufosinate sodium | Metolachlor | Saflufenacil |
| 454 | L-Glufosinate sodium | (S)-Metolachlor | Saflufenacil |
| 455 | L-Glufosinate sodium | Dimethenamid | Saflufenacil |
| 456 | L-Glufosinate sodium | Dimethenamid-P | Saflufenacil |
| 457 | L-Glufosinate sodium | Pyroxasulfone | Saflufenacil |
| 458 | L-Glufosinate sodium | Clomazone | Saflufenacil |
| 459 | L-Glufosinate sodium | Pendimethalin | Saflufenacil |
| 460 | L-Glufosinate sodium | Trifluralin | Saflufenacil |
| 461 | L-Glufosinate sodium | Fomesafen | Saflufenacil |
| 462 | L-Glufosinate sodium | Oxyfluorfen | Saflufenacil |
| 463 | L-Glufosinate sodium | Flumioxazin | Saflufenacil |
| 464 | L-Glufosinate sodium | Sulfentrazone | Saflufenacil |
| 465 | L-Glufosinate sodium | Trifludimoxazin | Saflufenacil |
| 466 | L-Glufosinate sodium | Saflufenacil | Saflufenacil |
| 467 | L-Glufosinate sodium | Saflufenacil + trifludimoxazin | Saflufenacil |
| 468 | L-Glufosinate sodium | Isoxaflutole | Saflufenacil |
| 469 | L-Glufosinate sodium | Bicyclopyrone | Saflufenacil |
| 470 | L-Glufosinate sodium | Tembotrione | Saflufenacil |
| 471 | L-Glufosinate sodium | Mesotrione | Saflufenacil |
| 472 | Glyphosate | Prometryn | Saflufenacil |
| 473 | Glyphosate | Fluometuron | Saflufenacil |
| 474 | Glyphosate | Thidiazuron | Saflufenacil |
| 475 | Glyphosate | Diuron | Saflufenacil |
| 476 | Glyphosate | Acetochlor | Saflufenacil |
| 477 | Glyphosate | Metolachlor | Saflufenacil |
| 478 | Glyphosate | (S)-Metolachlor | Saflufenacil |
| 479 | Glyphosate | Dimethenamid | Saflufenacil |
| 480 | Glyphosate | Dimethenamid-P | Saflufenacil |
| 481 | Glyphosate | Pyroxasulfone | Saflufenacil |
| 482 | Glyphosate | Clomazone | Saflufenacil |
| 483 | Glyphosate | Pendimethalin | Saflufenacil |
| 484 | Glyphosate | Trifluralin | Saflufenacil |
| 485 | Glyphosate | Fomesafen | Saflufenacil |
| 486 | Glyphosate | Oxyfluorfen | Saflufenacil |
| 487 | Glyphosate | Flumioxazin | Saflufenacil |
| 488 | Glyphosate | Sulfentrazone | Saflufenacil |
| 489 | Glyphosate | Trifludimoxazin | Saflufenacil |
| 490 | Glyphosate | Saflufenacil | Saflufenacil |
| 491 | Glyphosate | Saflufenacil + trifludimoxazin | Saflufenacil |
| 492 | Glyphosate | Isoxaflutole | Saflufenacil |
| 493 | Glyphosate | Bicyclopyrone | Saflufenacil |
| 494 | Glyphosate | Tembotrione | Saflufenacil |
| 495 | Glyphosate | Mesotrione | Saflufenacil |
| 496 | Glyphosate dimethylammonium | Prometryn | Saflufenacil |
| 497 | Glyphosate dimethylammonium | Fluometuron | Saflufenacil |
| 498 | Glyphosate dimethylammonium | Thidiazuron | Saflufenacil |
| 499 | Glyphosate dimethylammonium | Diuron | Saflufenacil |
| 500 | Glyphosate dimethylammonium | Acetochlor | Saflufenacil |
| 501 | Glyphosate dimethylammonium | Metolachlor | Saflufenacil |
| 502 | Glyphosate dimethylammonium | (S)-Metolachlor | Saflufenacil |
| 503 | Glyphosate dimethylammonium | Dimethenamid | Saflufenacil |
| 504 | Glyphosate dimethylammonium | Dimethenamid-P | Saflufenacil |

-continued

| Treatment combination | Pre-plant burn-down | Pre-emergence | Pre-harvest desiccation/ defoliation |
|---|---|---|---|
| 505 | Glyphosate dimethylammonium | Pyroxasulfone | Saflufenacil |
| 506 | Glyphosate dimethylammonium | Clomazone | Saflufenacil |
| 507 | Glyphosate dimethylammonium | Pendimethalin | Saflufenacil |
| 508 | Glyphosate dimethylammonium | Trifluralin | Saflufenacil |
| 509 | Glyphosate dimethylammonium | Fomesafen | Saflufenacil |
| 510 | Glyphosate dimethylammonium | Oxyfluorfen | Saflufenacil |
| 511 | Glyphosate dimethylammonium | Flumioxazin | Saflufenacil |
| 512 | Glyphosate dimethylammonium | Sulfentrazone | Saflufenacil |
| 513 | Glyphosate dimethylammonium | Trifludimoxazin | Saflufenacil |
| 514 | Glyphosate dimethylammonium | Saflufenacil | Saflufenacil |
| 515 | Glyphosate dimethylammonium | Saflufenacil + trifludimoxazin | Saflufenacil |
| 516 | Glyphosate dimethylammonium | Isoxaflutole | Saflufenacil |
| 517 | Glyphosate dimethylammonium | Bicyclopyrone | Saflufenacil |
| 518 | Glyphosate dimethylammonium | Tembotrione | Saflufenacil |
| 519 | Glyphosate dimethylammonium | Mesotrione | Saflufenacil |
| 520 | Glyphosate potassium | Prometryn | Saflufenacil |
| 521 | Glyphosate potassium | Fluometuron | Saflufenacil |
| 522 | Glyphosate potassium | Thidiazuron | Saflufenacil |
| 523 | Glyphosate potassium | Diuron | Saflufenacil |
| 524 | Glyphosate potassium | Acetochlor | Saflufenacil |
| 525 | Glyphosate potassium | Metolachlor | Saflufenacil |
| 526 | Glyphosate potassium | (S)-Metolachlor | Saflufenacil |
| 527 | Glyphosate potassium | Dimethenamid | Saflufenacil |
| 528 | Glyphosate potassium | Dimethenamid-P | Saflufenacil |
| 529 | Glyphosate potassium | Pyroxasulfone | Saflufenacil |
| 530 | Glyphosate potassium | Clomazone | Saflufenacil |
| 531 | Glyphosate potassium | Pendimethalin | Saflufenacil |
| 532 | Glyphosate potassium | Trifluralin | Saflufenacil |
| 533 | Glyphosate potassium | Fomesafen | Saflufenacil |
| 534 | Glyphosate potassium | Oxyfluorfen | Saflufenacil |
| 535 | Glyphosate potassium | Flumioxazin | Saflufenacil |
| 536 | Glyphosate potassium | Sulfentrazone | Saflufenacil |
| 537 | Glyphosate potassium | Trifludimoxazin | Saflufenacil |
| 538 | Glyphosate potassium | Saflufenacil | Saflufenacil |
| 539 | Glyphosate potassium | Saflufenacil + trifludimoxazin | Saflufenacil |
| 540 | Glyphosate potassium | Isoxaflutole | Saflufenacil |
| 541 | Glyphosate potassium | Bicyclopyrone | Saflufenacil |
| 542 | Glyphosate potassium | Tembotrione | Saflufenacil |
| 543 | Glyphosate potassium | Mesotrione | Saflufenacil |
| 544 | Glyphosate isopropylammonium | Prometryn | Saflufenacil |
| 545 | Glyphosate isopropylammonium | Fluometuron | Saflufenacil |
| 546 | Glyphosate isopropylammonium | Thidiazuron | Saflufenacil |
| 547 | Glyphosate isopropylammonium | Diuron | Saflufenacil |
| 548 | Glyphosate isopropylammonium | Acetochlor | Saflufenacil |
| 549 | Glyphosate isopropylammonium | Metolachlor | Saflufenacil |
| 550 | Glyphosate isopropylammonium | (S)-Metolachlor | Saflufenacil |
| 551 | Glyphosate isopropylammonium | Dimethenamid | Saflufenacil |
| 552 | Glyphosate isopropylammonium | Dimethenamid-P | Saflufenacil |
| 553 | Glyphosate isopropylammonium | Pyroxasulfone | Saflufenacil |
| 554 | Glyphosate isopropylammonium | Clomazone | Saflufenacil |
| 555 | Glyphosate isopropylammonium | Pendimethalin | Saflufenacil |
| 556 | Glyphosate isopropylammonium | Trifluralin | Saflufenacil |
| 557 | Glyphosate isopropylammonium | Fomesafen | Saflufenacil |
| 558 | Glyphosate isopropylammonium | Oxyfluorfen | Saflufenacil |
| 559 | Glyphosate isopropylammonium | Flumioxazin | Saflufenacil |
| 560 | Glyphosate isopropylammonium | Sulfentrazone | Saflufenacil |
| 561 | Glyphosate isopropylammonium | Trifludimoxazin | Saflufenacil |
| 562 | Glyphosate isopropylammonium | Saflufenacil | Saflufenacil |
| 563 | Glyphosate isopropylammonium | Saflufenacil + trifludimoxazin | Saflufenacil |
| 564 | Glyphosate isopropylammonium | Isoxaflutole | Saflufenacil |
| 565 | Glyphosate isopropylammonium | Bicyclopyrone | Saflufenacil |
| 566 | Glyphosate isopropylammonium | Tembotrione | Saflufenacil |
| 567 | Glyphosate isopropylammonium | Mesotrione | Saflufenacil |
| 568 | Saflufenacil | Prometryn | Saflufenacil |
| 569 | Saflufenacil | Fluometuron | Saflufenacil |
| 570 | Saflufenacil | Thidiazuron | Saflufenacil |
| 571 | Saflufenacil | Diuron | Saflufenacil |
| 572 | Saflufenacil | Acetochlor | Saflufenacil |
| 573 | Saflufenacil | Metolachlor | Saflufenacil |
| 574 | Saflufenacil | (S)-Metolachlor | Saflufenacil |
| 575 | Saflufenacil | Dimethenamid | Saflufenacil |
| 576 | Saflufenacil | Dimethenamid-P | Saflufenacil |
| 577 | Saflufenacil | Pyroxasulfone | Saflufenacil |
| 578 | Saflufenacil | Clomazone | Saflufenacil |
| 579 | Saflufenacil | Pendimethalin | Saflufenacil |

-continued

| Treatment combination | Pre-plant burn-down | Pre-emergence | Pre-harvest desiccation/ defoliation |
|---|---|---|---|
| 580 | Saflufenacil | Trifluralin | Saflufenacil |
| 581 | Saflufenacil | Fomesafen | Saflufenacil |
| 582 | Saflufenacil | Oxyfluorfen | Saflufenacil |
| 583 | Saflufenacil | Flumioxazin | Saflufenacil |
| 584 | Saflufenacil | Sulfentrazone | Saflufenacil |
| 585 | Saflufenacil | Trifludimoxazin | Saflufenacil |
| 586 | Saflufenacil | Saflufenacil | Saflufenacil |
| 587 | Saflufenacil | Saflufenacil + trifludimoxazin | Saflufenacil |
| 588 | Saflufenacil | Isoxaflutole | Saflufenacil |
| 589 | Saflufenacil | Bicyclopyrone | Saflufenacil |
| 590 | Saflufenacil | Tembotrione | Saflufenacil |
| 591 | Saflufenacil | Mesotrione | Saflufenacil |
| 592 | Trifludimoxazin | Prometryn | Saflufenacil |
| 593 | Trifludimoxazin | Fluometuron | Saflufenacil |
| 594 | Trifludimoxazin | Thidiazuron | Saflufenacil |
| 595 | Trifludimoxazin | Diuron | Saflufenacil |
| 596 | Trifludimoxazin | Acetochlor | Saflufenacil |
| 597 | Trifludimoxazin | Metolachlor | Saflufenacil |
| 598 | Trifludimoxazin | (S)-Metolachlor | Saflufenacil |
| 599 | Trifludimoxazin | Dimethenamid | Saflufenacil |
| 600 | Trifludimoxazin | Dimethenamid-P | Saflufenacil |
| 601 | Trifludimoxazin | Pyroxasulfone | Saflufenacil |
| 602 | Trifludimoxazin | Clomazone | Saflufenacil |
| 603 | Trifludimoxazin | Pendimethalin | Saflufenacil |
| 604 | Trifludimoxazin | Trifluralin | Saflufenacil |
| 605 | Trifludimoxazin | Fomesafen | Saflufenacil |
| 606 | Trifludimoxazin | Oxyfluorfen | Saflufenacil |
| 607 | Trifludimoxazin | Flumioxazin | Saflufenacil |
| 608 | Trifludimoxazin | Sulfentrazone | Saflufenacil |
| 609 | Trifludimoxazin | Trifludimoxazin | Saflufenacil |
| 610 | Trifludimoxazin | Saflufenacil | Saflufenacil |
| 611 | Trifludimoxazin | Saflufenacil + trifludimoxazin | Saflufenacil |
| 612 | Trifludimoxazin | Isoxaflutole | Saflufenacil |
| 613 | Trifludimoxazin | Bicyclopyrone | Saflufenacil |
| 614 | Trifludimoxazin | Tembotrione | Saflufenacil |
| 615 | Trifludimoxazin | Mesotrione | Saflufenacil |
| 616 | Saflufenacil + trifludimoxazin | Prometryn | Saflufenacil |
| 617 | Saflufenacil + trifludimoxazin | Fluometuron | Saflufenacil |
| 618 | Saflufenacil + trifludimoxazin | Thidiazuron | Saflufenacil |
| 619 | Saflufenacil + trifludimoxazin | Diuron | Saflufenacil |
| 620 | Saflufenacil + trifludimoxazin | Acetochlor | Saflufenacil |
| 621 | Saflufenacil + trifludimoxazin | Metolachlor | Saflufenacil |
| 622 | Saflufenacil + trifludimoxazin | (S)-Metolachlor | Saflufenacil |
| 623 | Saflufenacil + trifludimoxazin | Dimethenamid | Saflufenacil |
| 624 | Saflufenacil + trifludimoxazin | Dimethenamid-P | Saflufenacil |
| 625 | Saflufenacil + trifludimoxazin | Pyroxasulfone | Saflufenacil |
| 626 | Saflufenacil + trifludimoxazin | Clomazone | Saflufenacil |
| 627 | Saflufenacil + trifludimoxazin | Pendimethalin | Saflufenacil |
| 628 | Saflufenacil + trifludimoxazin | Trifluralin | Saflufenacil |
| 629 | Saflufenacil + trifludimoxazin | Fomesafen | Saflufenacil |
| 630 | Saflufenacil + trifludimoxazin | Oxyfluorfen | Saflufenacil |
| 631 | Saflufenacil + trifludimoxazin | Flumioxazin | Saflufenacil |
| 632 | Saflufenacil + trifludimoxazin | Sulfentrazone | Saflufenacil |
| 633 | Saflufenacil + trifludimoxazin | Trifludimoxazin | Saflufenacil |
| 634 | Saflufenacil + trifludimoxazin | Saflufenacil | Saflufenacil |
| 635 | Saflufenacil + trifludimoxazin | Saflufenacil + trifludimoxazin | Saflufenacil |
| 636 | Saflufenacil + trifludimoxazin | Isoxaflutole | Saflufenacil |
| 637 | Saflufenacil + trifludimoxazin | Bicyclopyrone | Saflufenacil |
| 638 | Saflufenacil + trifludimoxazin | Tembotrione | Saflufenacil |
| 639 | Saflufenacil + trifludimoxazin | Mesotrione | Saflufenacil |
| 640 | Dicamba | Prometryn | Saflufenacil |
| 641 | Dicamba | Fluometuron | Saflufenacil |
| 642 | Dicamba | Thidiazuron | Saflufenacil |
| 643 | Dicamba | Diuron | Saflufenacil |
| 644 | Dicamba | Acetochlor | Saflufenacil |
| 645 | Dicamba | Metolachlor | Saflufenacil |
| 646 | Dicamba | (S)-Metolachlor | Saflufenacil |
| 647 | Dicamba | Dimethenamid | Saflufenacil |
| 648 | Dicamba | Dimethenamid-P | Saflufenacil |
| 649 | Dicamba | Pyroxasulfone | Saflufenacil |
| 650 | Dicamba | Clomazone | Saflufenacil |
| 651 | Dicamba | Pendimethalin | Saflufenacil |
| 652 | Dicamba | Trifluralin | Saflufenacil |
| 653 | Dicamba | Fomesafen | Saflufenacil |
| 654 | Dicamba | Oxyfluorfen | Saflufenacil |

| Treatment combination | Pre-plant burn-down | Pre-emergence | Pre-harvest desiccation/ defoliation |
|---|---|---|---|
| 655 | Dicamba | Flumioxazin | Saflufenacil |
| 656 | Dicamba | Sulfentrazone | Saflufenacil |
| 657 | Dicamba | Trifludimoxazin | Saflufenacil |
| 658 | Dicamba | Saflufenacil | Saflufenacil |
| 659 | Dicamba | Saflufenacil + trifludimoxazin | Saflufenacil |
| 660 | Dicamba | Isoxaflutole | Saflufenacil |
| 661 | Dicamba | Bicyclopyrone | Saflufenacil |
| 662 | Dicamba | Tembotrione | Saflufenacil |
| 663 | Dicamba | Mesotrione | Saflufenacil |
| 664 | Dicamba ethanolamine salt | Prometryn | Saflufenacil |
| 665 | Dicamba ethanolamine salt | Fluometuron | Saflufenacil |
| 666 | Dicamba ethanolamine salt | Thidiazuron | Saflufenacil |
| 667 | Dicamba ethanolamine salt | Diuron | Saflufenacil |
| 668 | Dicamba ethanolamine salt | Acetochlor | Saflufenacil |
| 669 | Dicamba ethanolamine salt | Metolachlor | Saflufenacil |
| 670 | Dicamba ethanolamine salt | (S)-Metolachlor | Saflufenacil |
| 671 | Dicamba ethanolamine salt | Dimethenamid | Saflufenacil |
| 672 | Dicamba ethanolamine salt | Dimethenamid-P | Saflufenacil |
| 673 | Dicamba ethanolamine salt | Pyroxasulfone | Saflufenacil |
| 674 | Dicamba ethanolamine salt | Clomazone | Saflufenacil |
| 675 | Dicamba ethanolamine salt | Pendimethalin | Saflufenacil |
| 676 | Dicamba ethanolamine salt | Trifluralin | Saflufenacil |
| 677 | Dicamba ethanolamine salt | Fomesafen | Saflufenacil |
| 678 | Dicamba ethanolamine salt | Oxyfluorfen | Saflufenacil |
| 679 | Dicamba ethanolamine salt | Flumioxazin | Saflufenacil |
| 680 | Dicamba ethanolamine salt | Sulfentrazone | Saflufenacil |
| 681 | Dicamba ethanolamine salt | Trifludimoxazin | Saflufenacil |
| 682 | Dicamba ethanolamine salt | Saflufenacil | Saflufenacil |
| 683 | Dicamba ethanolamine salt | Saflufenacil + trifludimoxazin | Saflufenacil |
| 684 | Dicamba ethanolamine salt | Isoxaflutole | Saflufenacil |
| 685 | Dicamba ethanolamine salt | Bicyclopyrone | Saflufenacil |
| 686 | Dicamba ethanolamine salt | Tembotrione | Saflufenacil |
| 687 | Dicamba ethanolamine salt | Mesotrione | Saflufenacil |
| 688 | Dicamba diglycolamine salt | Prometryn | Saflufenacil |
| 689 | Dicamba diglycolamine salt | Fluometuron | Saflufenacil |
| 690 | Dicamba diglycolamine salt | Thidiazuron | Saflufenacil |
| 691 | Dicamba diglycolamine salt | Diuron | Saflufenacil |
| 692 | Dicamba diglycolamine salt | Acetochlor | Saflufenacil |
| 693 | Dicamba diglycolamine salt | Metolachlor | Saflufenacil |
| 694 | Dicamba diglycolamine salt | (S)-Metolachlor | Saflufenacil |
| 695 | Dicamba diglycolamine salt | Dimethenamid | Saflufenacil |
| 696 | Dicamba diglycolamine salt | Dimethenamid-P | Saflufenacil |
| 697 | Dicamba diglycolamine salt | Pyroxasulfone | Saflufenacil |
| 698 | Dicamba diglycolamine salt | Clomazone | Saflufenacil |
| 699 | Dicamba diglycolamine salt | Pendimethalin | Saflufenacil |
| 700 | Dicamba diglycolamine salt | Trifluralin | Saflufenacil |
| 701 | Dicamba diglycolamine salt | Fomesafen | Saflufenacil |
| 702 | Dicamba diglycolamine salt | Oxyfluorfen | Saflufenacil |
| 703 | Dicamba diglycolamine salt | Flumioxazin | Saflufenacil |
| 704 | Dicamba diglycolamine salt | Sulfentrazone | Saflufenacil |
| 705 | Dicamba diglycolamine salt | Trifludimoxazin | Saflufenacil |
| 706 | Dicamba diglycolamine salt | Saflufenacil | Saflufenacil |
| 707 | Dicamba diglycolamine salt | Saflufenacil + trifludimoxazin | Saflufenacil |
| 708 | Dicamba diglycolamine salt | Isoxaflutole | Saflufenacil |
| 709 | Dicamba diglycolamine salt | Bicyclopyrone | Saflufenacil |
| 710 | Dicamba diglycolamine salt | Tembotrione | Saflufenacil |
| 711 | Dicamba diglycolamine salt | Mesotrione | Saflufenacil |
| 712 | Dicamba potassium | Prometryn | Saflufenacil |
| 713 | Dicamba potassium | Fluometuron | Saflufenacil |
| 714 | Dicamba potassium | Thidiazuron | Saflufenacil |
| 715 | Dicamba potassium | Diuron | Saflufenacil |
| 716 | Dicamba potassium | Acetochlor | Saflufenacil |
| 717 | Dicamba potassium | Metolachlor | Saflufenacil |
| 718 | Dicamba potassium | (S)-Metolachlor | Saflufenacil |
| 719 | Dicamba potassium | Dimethenamid | Saflufenacil |
| 720 | Dicamba potassium | Dimethenamid-P | Saflufenacil |
| 721 | Dicamba potassium | Pyroxasulfone | Saflufenacil |
| 722 | Dicamba potassium | Clomazone | Saflufenacil |
| 723 | Dicamba potassium | Pendimethalin | Saflufenacil |
| 724 | Dicamba potassium | Trifluralin | Saflufenacil |
| 725 | Dicamba potassium | Fomesafen | Saflufenacil |
| 726 | Dicamba potassium | Oxyfluorfen | Saflufenacil |
| 727 | Dicamba potassium | Flumioxazin | Saflufenacil |
| 728 | Dicamba potassium | Sulfentrazone | Saflufenacil |
| 729 | Dicamba potassium | Trifludimoxazin | Saflufenacil |

-continued

| Treatment combination | Pre-plant burn-down | Pre-emergence | Pre-harvest desiccation/defoliation |
|---|---|---|---|
| 730 | Dicamba potassium | Saflufenacil | Saflufenacil |
| 731 | Dicamba potassium | Saflufenacil + trifludimoxazin | Saflufenacil |
| 732 | Dicamba potassium | Isoxaflutole | Saflufenacil |
| 733 | Dicamba potassium | Bicyclopyrone | Saflufenacil |
| 734 | Dicamba potassium | Tembotrione | Saflufenacil |
| 735 | Dicamba potassium | Mesotrione | Saflufenacil |
| 736 | Dicamba BAPMA salt | Prometryn | Saflufenacil |
| 737 | Dicamba BAPMA salt | Fluometuron | Saflufenacil |
| 738 | Dicamba BAPMA salt | Thidiazuron | Saflufenacil |
| 739 | Dicamba BAPMA salt | Diuron | Saflufenacil |
| 740 | Dicamba BAPMA salt | Acetochlor | Saflufenacil |
| 741 | Dicamba BAPMA salt | Metolachlor | Saflufenacil |
| 742 | Dicamba BAPMA salt | (S)-Metolachlor | Saflufenacil |
| 743 | Dicamba BAPMA salt | Dimethenamid | Saflufenacil |
| 744 | Dicamba BAPMA salt | Dimethenamid-P | Saflufenacil |
| 745 | Dicamba BAPMA salt | Pyroxasulfone | Saflufenacil |
| 746 | Dicamba BAPMA salt | Clomazone | Saflufenacil |
| 747 | Dicamba BAPMA salt | Pendimethalin | Saflufenacil |
| 748 | Dicamba BAPMA salt | Trifluralin | Saflufenacil |
| 749 | Dicamba BAPMA salt | Fomesafen | Saflufenacil |
| 750 | Dicamba BAPMA salt | Oxyfluorfen | Saflufenacil |
| 751 | Dicamba BAPMA salt | Flumioxazin | Saflufenacil |
| 752 | Dicamba BAPMA salt | Sulfentrazone | Saflufenacil |
| 753 | Dicamba BAPMA salt | Trifludimoxazin | Saflufenacil |
| 754 | Dicamba BAPMA salt | Saflufenacil | Saflufenacil |
| 755 | Dicamba BAPMA salt | Saflufenacil + trifludimoxazin | Saflufenacil |
| 756 | Dicamba BAPMA salt | Isoxaflutole | Saflufenacil |
| 757 | Dicamba BAPMA salt | Bicyclopyrone | Saflufenacil |
| 758 | Dicamba BAPMA salt | Tembotrione | Saflufenacil |
| 759 | Dicamba BAPMA salt | Mesotrione | Saflufenacil |
| 760 | — | Prometryn | Saflufenacil |
| 761 | — | Fluometuron | Saflufenacil |
| 762 | — | Thidiazuron | Saflufenacil |
| 763 | — | Diuron | Saflufenacil |
| 764 | — | Acetochlor | Saflufenacil |
| 765 | — | Metolachlor | Saflufenacil |
| 766 | — | (S)-Metolachlor | Saflufenacil |
| 767 | — | Dimethenamid | Saflufenacil |
| 768 | — | Dimethenamid-P | Saflufenacil |
| 769 | — | Pyroxasulfone | Saflufenacil |
| 770 | — | Clomazone | Saflufenacil |
| 771 | — | Pendimethalin | Saflufenacil |
| 772 | — | Trifluralin | Saflufenacil |
| 773 | — | Fomesafen | Saflufenacil |
| 774 | — | Oxyfluorfen | Saflufenacil |
| 775 | — | Flumioxazin | Saflufenacil |
| 776 | — | Sulfentrazone | Saflufenacil |
| 777 | — | Trifludimoxazin | Saflufenacil |
| 778 | — | Saflufenacil | Saflufenacil |
| 779 | — | Saflufenacil + trifludimoxazin | Saflufenacil |
| 780 | — | Isoxaflutole | Saflufenacil |
| 781 | — | Bicyclopyrone | Saflufenacil |
| 782 | — | Tembotrione | Saflufenacil |
| 783 | — | Mesotrione | Saflufenacil |
| 784 | L-Glufosinate | — | Saflufenacil |
| 785 | L-Glufosinate ammonium | — | Saflufenacil |
| 786 | L-Glufosinate sodium | — | Saflufenacil |
| 787 | Glyphosate | — | Saflufenacil |
| 788 | Glyphosate dimethylammonium | — | Saflufenacil |
| 789 | Glyphosate potassium | — | Saflufenacil |
| 790 | Glyphosate isopropylammonium | — | Saflufenacil |
| 791 | Saflufenacil | — | Saflufenacil |
| 792 | Trifludimoxazin | — | Saflufenacil |
| 793 | Saflufenacil + trifludimoxazin | — | Saflufenacil |
| 794 | Dicamba | — | Saflufenacil |
| 795 | Dicamba ethanolamine salt | — | Saflufenacil |
| 796 | Dicamba diglycolamine salt | — | Saflufenacil |
| 797 | Dicamba potassium | — | Saflufenacil |
| 798 | Dicamba BAPMA salt | — | Saflufenacil |
| 799 | — | — | Saflufenacil |

The treatment combinations 2.1 to 2.799 in which one of the treatment combinations listed in the preceeding table is combined with post-emergence use of L-glufosinate ammonium.

The treatment combinations 3.1 to 3.799 in which one of the treatment combinations listed in the preceeding table is combined with post-emergence use of L-glufosinate sodium.

The treatment combinations 4.1 to 4.799 in which one of the treatment combinations listed in the preceeding table is combined with post-emergence use of L-glufosinate and acetochlor.

The treatment combinations 5.1 to 5.799 in which one of the treatment combinations listed in the preceeding table is combined with post-emergence use of L-glufosinate ammonium and acetochlor.

The treatment combinations 6.1 to 6.799 in which one of the treatment combinations listed in the preceeding table is combined with post-emergence use of L-glufosinate sodium and acetochlor.

The treatment combinations 7.1 to 7.799 in which one of the treatment combinations listed in the preceeding table is combined with post-emergence use of L-glufosinate and (S)-metolachlor.

The treatment combinations 8.1 to 8.799 in which one of the treatment combinations listed in the preceeding table is combined with post-emergence use of L-glufosinate ammonium and (S)-metolachlor.

The treatment combinations 9.1 to 9.799 in which one of the treatment combinations listed in the preceeding table is combined with post-emergence use of L-glufosinate sodium and (S)-metolachlor.

The treatment combinations 10.1 to 10.799 in which one of the treatment combinations listed in the preceeding table is combined with post-emergence use of L-glufosinate and dimethenamid-P.

The treatment combinations 11.1 to 11.799 in which one of the treatment combinations listed in the preceeding table is combined with post-emergence use of L-glufosinate ammonium and dimethenamid-P.

The treatment combinations 12.1 to 12.799 in which one of the treatment combinations listed in the preceeding table is combined with post-emergence use of L-glufosinate sodium and dimethenamid-P.

The treatment combinations 13.1 to 13.799 in which one of the treatment combinations listed in the preceeding table is combined with post-emergence use of L-glufosinate and pyroxasulfone.

The treatment combinations 14.1 to 14.799 in which one of the treatment combinations listed in the preceeding table is combined with post-emergence use of L-glufosinate ammonium and pyroxasulfone.

The treatment combinations 15.1 to 15.799 in which one of the treatment combinations listed in the preceeding table is combined with post-emergence use of L-glufosinate sodium and pyroxasulfone.

The treatment combinations 16.1 to 16.799 in which one of the treatment combinations listed in the preceeding table is combined with post-emergence use of L-glufosinate and isoxaflutole.

The treatment combinations 17.1 to 17.799 in which one of the treatment combinations listed in the preceeding table is combined with post-emergence use of L-glufosinate ammonium and isoxaflutole.

The treatment combinations 18.1 to 18.799 in which one of the treatment combinations listed in the preceeding table is combined with post-emergence use of L-glufosinate sodium and isoxaflutole.

The treatment combinations 19.1 to 19.799 in which one of the treatment combinations listed in the preceeding table is combined with post-emergence use of L-glufosinate and topramezone.

The treatment combinations 20.1 to 20.799 in which one of the treatment combinations listed in the preceeding table is combined with post-emergence use of L-glufosinate ammonium and topramezone.

The treatment combinations 21.1 to 21.799 in which one of the treatment combinations listed in the preceeding table is combined with post-emergence use of L-glufosinate sodium and topramezone.

The treatment combinations 22.1 to 22.799 in which one of the treatment combinations listed in the preceeding table is combined with post-emergence use of L-glufosinate and bicyclopyrone.

The treatment combinations 23.1 to 23.799 in which one of the treatment combinations listed in the preceeding table is combined with post-emergence use of L-glufosinate ammonium and bicyclopyrone.

The treatment combinations 24.1 to 24.799 in which one of the treatment combinations listed in the preceeding table is combined with post-emergence use of L-glufosinate sodium and bicyclopyrone.

The treatment combinations 25.1 to 25.799 in which one of the treatment combinations listed in the preceeding table is combined with post-emergence use of L-glufosinate and tembotrione.

The treatment combinations 26.1 to 26.799 in which one of the treatment combinations listed in the preceeding table is combined with post-emergence use of L-glufosinate ammonium and tembotrione.

The treatment combinations 27.1 to 27.799 in which one of the treatment combinations listed in the preceeding table is combined with post-emergence use of L-glufosinate sodium and tembotrione.

The treatment combinations 28.1 to 28.799 in which one of the treatment combinations listed in the preceeding table is combined with post-emergence use of L-glufosinate and mesotrione.

The treatment combinations 29.1 to 29.799 in which one of the treatment combinations listed in the preceeding table is combined with post-emergence use of L-glufosinate ammonium and mesotrione.

The treatment combinations 30.1 to 30.799 in which one of the treatment combinations listed in the preceeding table is combined with post-emergence use of L-glufosinate sodium and mesotrione.

The treatment combinations 31.1 to 31.799 in which one of the treatment combinations listed in the preceeding table is combined with post-emergence use of L-glufosinate and carfentrazone-ethyl.

The treatment combinations 32.1 to 32.799 in which one of the treatment combinations listed in the preceeding table is combined with post-emergence use of L-glufosinate ammonium and carfentrazone-ethyl.

The treatment combinations 33.1 to 33.799 in which one of the treatment combinations listed in the preceeding table is combined with post-emergence use of L-glufosinate sodium and carfentrazone-ethyl.

The treatment combinations 34.1 to 34.799 in which one of the treatment combinations listed in the preceeding table is combined with post-emergence use of L-glufosinate and sulfentrazone.

The treatment combinations 35.1 to 35.799 in which one of the treatment combinations listed in the preceeding table is combined with post-emergence use of L-glufosinate ammonium and sulfentrazone.

The treatment combinations 36.1 to 36.799 in which one of the treatment combinations listed in the preceeding table is combined with post-emergence use of L-glufosinate sodium and sulfentrazone.

The treatment combinations 37.1 to 37.799 in which one of the treatment combinations listed in the preceeding table is combined with post-emergence use of L-glufosinate and saflufenacil.

The treatment combinations 38.1 to 38.799 in which one of the treatment combinations listed in the preceeding table is combined with post-emergence use of L-glufosinate ammonium and saflufenacil.

The treatment combinations 39.1 to 39.799 in which one of the treatment combinations listed in the preceeding table is combined with post-emergence use of L-glufosinate sodium and saflufenacil.

The treatment combinations 40.1 to 40.799 in which one of the treatment combinations listed in the preceeding table is combined with post-emergence use of L-glufosinate and trifludimoxazin.

The treatment combinations 41.1 to 41.799 in which one of the treatment combinations listed in the preceeding table is combined with post-emergence use of L-glufosinate ammonium and trifludimoxazin.

The treatment combinations 42.1 to 42.799 in which one of the treatment combinations listed in the preceeding table is combined with post-emergence use of L-glufosinate sodium and trifludimoxazin.

The treatment combinations 43.1 to 43.799 in which one of the treatment combinations listed in the preceeding table is combined with post-emergence use of L-glufosinate, saflufenacil and trifludimoxazin.

The treatment combinations 44.1 to 44.799 in which one of the treatment combinations listed in the preceeding table is combined with post-emergence use of L-glufosinate ammonium, saflufenacil and trifludimoxazin.

The treatment combinations 45.1 to 45.799 in which one of the treatment combinations listed in the preceeding table is combined with post-emergence use of L-glufosinate sodium, saflufenacil and trifludimoxazin.

The treatment combinations 46.1 to 46.799 in which one of the treatment combinations listed in the preceeding table is combined with post-emergence use of L-glufosinate and pyraflufen-ethyl.

The treatment combinations 47.1 to 47.799 in which one of the treatment combinations listed in the preceeding table is combined with post-emergence use of L-glufosinate ammonium and pyraflufen-ethyl.

The treatment combinations 48.1 to 48.799 in which one of the treatment combinations listed in the preceeding table is combined with post-emergence use of L-glufosinate sodium and pyraflufen-ethyl.

The treatment combinations 49.1 to 49.799 in which one of the treatment combinations listed in the preceeding table is combined with post-emergence use of L-glufosinate and fluthiacet-methyl.

The treatment combinations 50.1 to 50.799 in which one of the treatment combinations listed in the preceeding table is combined with post-emergence use of L-glufosinate ammonium and fluthiacet-methyl.

The treatment combinations 51.1 to 51.799 in which one of the treatment combinations listed in the preceeding table is combined with post-emergence use of L-glufosinate sodium and fluthiacet-methyl.

The treatment combinations 52.1 to 52.799 in which one of the treatment combinations listed in the preceeding table is combined with post-emergence use of L-glufosinate and clethodim.

The treatment combinations 53.1 to 53.799 in which one of the treatment combinations listed in the preceeding table is combined with post-emergence use of L-glufosinate ammonium and clethodim.

The treatment combinations 54.1 to 54.799 in which one of the treatment combinations listed in the preceeding table is combined with post-emergence use of L-glufosinate sodium and clethodim.

The treatment combinations 55.1 to 55.799 in which one of the treatment combinations listed in the preceeding table is combined with post-emergence use of L-glufosinate and cycloxydim.

The treatment combinations 56.1 to 56.799 in which one of the treatment combinations listed in the preceeding table is combined with post-emergence use of L-glufosinate ammonium and cycloxydim.

The treatment combinations 57.1 to 57.799 in which one of the treatment combinations listed in the preceeding table is combined with post-emergence use of L-glufosinate sodium and cycloxydim.

The treatment combinations 58.1 to 58.799 in which one of the treatment combinations listed in the preceeding table is combined with post-emergence use of pyrithiobac sodium.

The treatment combinations 59.1 to 59.799 in which one of the treatment combinations listed in the preceeding table is combined with post-emergence use of acetochlor.

The treatment combinations 60.1 to 60.799 in which one of the treatment combinations listed in the preceeding table is combined with post-emergence use of metolachlor.

The treatment combinations 61.1 to 61.799 in which one of the treatment combinations listed in the preceeding table is combined with post-emergence use of (S)-metolachlor.

The treatment combinations 62.1 to 62.799 in which one of the treatment combinations listed in the preceeding table is combined with post-emergence use of dimethenamid.

The treatment combinations 63.1 to 63.799 in which one of the treatment combinations listed in the preceeding table is combined with post-emergence use of dimethenamid-P.

The treatment combinations 64.1 to 64.799 in which one of the treatment combinations listed in the preceeding table is combined with post-emergence use of pyroxasulfone.

The treatment combinations 65.1 to 65.799 in which one of the treatment combinations listed in the preceeding table is combined with post-emergence use of isoxaflutole.

The treatment combinations 66.1 to 66.799 in which one of the treatment combinations listed in the preceeding table is combined with post-emergence use of topramezone.

The treatment combinations 67.1 to 67.799 in which one of the treatment combinations listed in the preceeding table is combined with post-emergence use of bicyclopyrone.

The treatment combinations 68.1 to 68.799 in which one of the treatment combinations listed in the preceeding table is combined with post-emergence use of tembotrione.

The treatment combinations 69.1 to 69.799 in which one of the treatment combinations listed in the preceeding table is combined with post-emergence use of mesotrione.

The treatment combinations 70.1 to 70.799 in which one of the treatment combinations listed in the preceeding table is combined with post-emergence use of carfentrazone-ethyl.

The treatment combinations 71.1 to 71.799 in which one of the treatment combinations listed in the preceeding table is combined with post-emergence use of saflufenacil.

The treatment combinations 72.1 to 72.799 in which one of the treatment combinations listed in the preceeding table is combined with post-emergence use of trifludimoxazin.

The treatment combinations 73.1 to 73.799 in which one of the treatment combinations listed in the preceeding table is combined with post-emergence use of saflufenacil and trifludimoxazin.

The treatment combinations 74.1 to 74.799 in which one of the treatment combinations listed in the preceeding table is combined with post-emergence use of sulfentrazone.

The treatment combinations 75.1 to 75.799 in which one of the treatment combinations listed in the preceeding table is combined with post-emergence use of pyraflufen-ethyl.

The treatment combinations 76.1 to 76.799 in which one of the treatment combinations listed in the preceeding table is combined with post-emergence use of fluthiacet-methyl.

The treatment combinations 77.1 to 77.799 in which one of the treatment combinations listed in the preceeding table is combined with post-emergence use of flumioxazin.

The treatment combinations 78.1 to 78.799 in which one of the treatment combinations listed in the preceeding table is combined with post-emergence use of oxyfluorfen.

The treatment combinations 79.1 to 79.799 in which one of the treatment combinations listed in the preceeding table is combined with post-emergence use of fomesafen.

The treatment combinations 80.1 to 80.799 in which one of the treatment combinations listed in the preceeding table is combined with post-emergence use of clethodim.

The treatment combinations 81.1 to 81.799 in which one of the treatment combinations listed in the preceeding table is combined with post-emergence use of cycloxdim.

The treatment combinations 82.1 to 82.799 in which one of the treatment combinations listed in the preceeding table is combined with post-emergence use of sethoxydim.

The treatment combinations 83.1 to 83.799 in which one of the treatment combinations listed in the preceeding table is combined with post-emergence use of tepraloxydim.

The treatment combinations 84.1 to 84.799 in which one of the treatment combinations listed in the preceeding table is combined with post-emergence use of L-glufosinate and 2.4-D.

The treatment combinations 85.1 to 85.799 in which one of the treatment combinations listed in the preceeding table is combined with post-emergence use of L-glufosinate ammonium and 2.4-D.

The treatment combinations 86.1 to 86.799 in which one of the treatment combinations listed in the preceeding table is combined with post-emergence use of L-glufosinate sodium and 2.4-D.

The treatment combinations 87.1 to 87.799 in which one of the treatment combinations listed in the preceeding table is combined with post-emergence use of L-glufosinate and 2.4-D choline salt.

The treatment combinations 88.1 to 88.799 in which one of the treatment combinations listed in the preceeding table is combined with post-emergence use of L-glufosinate ammonium and 2.4-D choline salt.

The treatment combinations 89.1 to 89.799 in which one of the treatment combinations listed in the preceeding table is combined with post-emergence use L-glufosinate sodium and 2.4-D choline salt.

The treatment combinations 90.1 to 90.799 in which one of the treatment combinations listed in the preceeding table is combined with post-emergence use of 2,4-D.

The treatment combinations 91.1 to 91.799 in which one of the treatment combinations listed in the preceeding table is combined with post-emergence use of 2.4-D choline salt.

The treatment combinations 92.1 to 92.799 in which one of the treatment combinations listed in the preceeding table is combined with post-emergence use of L-glufosinate and dicamba.

The treatment combinations 93.1 to 93.799 in which one of the treatment combinations listed in the preceeding table is combined with post-emergence use of L-glufosinate and dicamba ethanolamine salt.

The treatment combinations 94.1 to 94.799 in which one of the treatment combinations listed in the preceeding table is combined with post-emergence use of L-glufosinate and dicamba diglycolamine salt.

The treatment combinations 95.1 to 95.799 in which one of the treatment combinations listed in the preceeding table is combined with post-emergence use of L-glufosinate and dicamba potassium.

The treatment combinations 96.1 to 96.799 in which one of the treatment combinations listed in the preceeding table is combined with post-emergence use of L-glufosinate and dicamba BAPMA salt.

The treatment combinations 97.1 to 97.799 in which one of the treatment combinations listed in the preceeding table is combined with post-emergence use of L-glufosinate ammonium and dicamba.

The treatment combinations 98.1 to 98.799 in which one of the treatment combinations listed in the preceeding table is combined with post-emergence use of L-glufosinate ammonium and dicamba ethanolamine salt.

The treatment combinations 99.1 to 99.799 in which one of the treatment combinations listed in the preceeding table is combined with post-emergence use of L-glufosinate ammonium and dicamba diglycolamine salt.

The treatment combinations 100.1 to 100.799 in which one of the treatment combinations listed in the preceeding table is combined with post-emergence use of L-glufosinate ammonium and dicamba potassium.

The treatment combinations 101.1 to 101.799 in which one of the treatment combinations listed in the preceeding table is combined with post-emergence use of L-glufosinate ammonium and dicamba BAPMA salt.

The treatment combinations 102.1 to 102.799 in which one of the treatment combinations listed in the preceeding table is combined with post-emergence use of L-glufosinate sodium and dicamba.

The treatment combinations 103.1 to 103.799 in which one of the treatment combinations listed in the preceeding table is combined with post-emergence use of L-glufosinate sodium and dicamba ethanolamine salt.

The treatment combinations 104.1 to 104.799 in which one of the treatment combinations listed in the preceeding table is combined with post-emergence use of L-glufosinate sodium and dicamba diglycolamine salt.

The treatment combinations 105.1 to 105.799 in which one of the treatment combinations listed in the preceeding table is combined with post-emergence use of L-glufosinate sodium and dicamba potassium.

The treatment combinations 106.1 to 106.799 in which one of the treatment combinations listed in the preceeding table is combined with post-emergence use of L-glufosinate sodium and dicamba BAPMA salt.

The treatment combinations 107.1 to 107.799 in which one of the treatment combinations listed in the preceeding table is combined with post-emergence use of L-glufosinate, glyphosate and dicamba.

The treatment combinations 108.1 to 108.799 in which one of the treatment combinations listed in the preceeding table is combined with post-emergence use of L-glufosinate, glyphosate and dicamba ethanolamine salt.

The treatment combinations 109.1 to 109.799 in which one of the treatment combinations listed in the preceeding table is combined with post-emergence use of L-glufosinate, glyphosate and dicamba diglycolamine salt.

The treatment combinations 110.1 to 110.799 in which one of the treatment combinations listed in the preceeding table is combined with post-emergence use of L-glufosinate, glyphosate and dicamba potassium.

The treatment combinations 111.1 to 111.799 in which one of the treatment combinations listed in the preceeding table is combined with post-emergence use of L-glufosinate, glyphosate and dicamba BAPMA salt.

The treatment combinations 112.1 to 112.799 in which one of the treatment combinations listed in the preceeding table is combined with post-emergence use of L-glufosinate ammonium, glyphosate and dicamba.

The treatment combinations 113.1 to 113.799 in which one of the treatment combinations listed in the preceeding table is combined with post-emergence use of L-glufosinate ammonium, glyphosate and dicamba ethanolamine salt.

The treatment combinations 114.1 to 114.799 in which one of the treatment combinations listed in the preceeding table is combined with post-emergence use of L-glufosinate ammonium, glyphosate and dicamba diglycolamine salt.

The treatment combinations 115.1 to 115.799 in which one of the treatment combinations listed in the preceeding table is combined with post-emergence use of L-glufosinate ammonium, glyphosate and dicamba potassium.

The treatment combinations 116.1 to 116.799 in which one of the treatment combinations listed in the preceeding table is combined with post-emergence use of L-glufosinate ammonium, glyphosate and dicamba BAPMA salt.

The treatment combinations 117.1 to 117.799 in which one of the treatment combinations listed in the preceeding table is combined with post-emergence use of L-glufosinate sodium, glyphosate and dicamba.

The treatment combinations 118.1 to 118.799 in which one of the treatment combinations listed in the preceeding table is combined with post-emergence use of L-glufosinate sodium, glyphosate and dicamba ethanolamine salt.

The treatment combinations 119.1 to 119.799 in which one of the treatment combinations listed in the preceeding table is combined with post-emergence use of L-glufosinate sodium, glyphosate and dicamba diglycolamine salt.

The treatment combinations 120.1 to 120.799 in which one of the treatment combinations listed in the preceeding table is combined with post-emergence use of L-glufosinate sodium, glyphosate and dicamba potassium.

The treatment combinations 121.1 to 121.799 in which one of the treatment combinations listed in the preceeding table is combined with post-emergence use of L-glufosinate sodium, glyphosate and dicamba BAPMA salt.

The treatment combinations 122.1 to 122.799 in which one of the treatment combinations listed in the preceeding table is combined with post-emergence use of L-glufosinate, glyphosate dimethylammonium and dicamba.

The treatment combinations 123.1 to 123.799 in which one of the treatment combinations listed in the preceeding table is combined with post-emergence use of L-glufosinate, glyphosate dimethylammonium and dicamba ethanolamine salt.

The treatment combinations 124.1 to 124.799 in which one of the treatment combinations listed in the preceeding table is combined with post-emergence use of L-glufosinate, glyphosate dimethylammonium and dicamba diglycolamine salt.

The treatment combinations 125.1 to 125.799 in which one of the treatment combinations listed in the preceeding table is combined with post-emergence use of L-glufosinate, glyphosate dimethylammonium and dicamba potassium.

The treatment combinations 126.1 to 126.799 in which one of the treatment combinations listed in the preceeding table is combined with post-emergence use of L-glufosinate, glyphosate dimethylammonium and dicamba BAPMA salt.

The treatment combinations 127.1 to 127.799 in which one of the treatment combinations listed in the preceeding table is combined with post-emergence use of L-glufosinate ammonium, glyphosate dimethylammonium and dicamba.

The treatment combinations 128.1 to 128.799 in which one of the treatment combinations listed in the preceeding table is combined with post-emergence use of L-glufosinate ammonium, glyphosate dimethylammonium and dicamba ethanolamine salt.

The treatment combinations 129.1 to 129.799 in which one of the treatment combinations listed in the preceeding table is combined with post-emergence use of L-glufosinate ammonium, glyphosate dimethylammonium and dicamba diglycolamine salt.

The treatment combinations 130.1 to 130.799 in which one of the treatment combinations listed in the preceeding table is combined with post-emergence use of L-glufosinate ammonium, glyphosate dimethylammonium and dicamba potassium.

The treatment combinations 131.1 to 131.799 in which one of the treatment combinations listed in the preceeding table is combined with post-emergence use of L-glufosinate ammonium, glyphosate dimethylammonium and dicamba BAPMA salt.

The treatment combinations 132.1 to 132.799 in which one of the treatment combinations listed in the preceeding table is combined with post-emergence use of L-glufosinate sodium, glyphosate dimethylammonium and dicamba.

The treatment combinations 133.1 to 133.799 in which one of the treatment combinations listed in the preceeding table is combined with post-emergence use of L-glufosinate sodium, glyphosate dimethylammonium and dicamba ethanolamine salt.

The treatment combinations 134.1 to 134.799 in which one of the treatment combinations listed in the preceeding table is combined with post-emergence use of L-glufosinate sodium, glyphosate dimethylammonium and dicamba diglycolamine salt.

The treatment combinations 135.1 to 135.799 in which one of the treatment combinations listed in the preceeding table is combined with post-emergence use of L-glufosinate sodium, glyphosate dimethylammonium and dicamba potassium.

The treatment combinations 136.1 to 136.799 in which one of the treatment combinations listed in the preceeding table is combined with post-emergence use of L-glufosinate sodium, glyphosate dimethylammonium and dicamba BAPMA salt.

The treatment combinations 137.1 to 137.799 in which one of the treatment combinations listed in the preceeding table is combined with post-emergence use of L-glufosinate, glyphosate potassium and dicamba.

The treatment combinations 138.1 to 138.799 in which one of the treatment combinations listed in the preceeding table is combined with post-emergence use of L-glufosinate, glyphosate potassium and dicamba ethanolamine salt.

The treatment combinations 139.1 to 139.799 in which one of the treatment combinations listed in the preceeding table is combined with post-emergence use of L-glufosinate, glyphosate potassium and dicamba diglycolamine salt.

The treatment combinations 140.1 to 140.799 in which one of the treatment combinations listed in the preceeding table is combined with post-emergence use of L-glufosinate, glyphosate potassium and dicamba potassium.

The treatment combinations 141.1 to 141.799 in which one of the treatment combinations listed in the preceeding table is combined with post-emergence use of L-glufosinate, glyphosate potassium and dicamba BAPMA salt.

The treatment combinations 142.1 to 142.799 in which one of the treatment combinations listed in the preceeding table is combined with post-emergence use of L-glufosinate ammonium, glyphosate potassium and dicamba.

The treatment combinations 143.1 to 143.799 in which one of the treatment combinations listed in the preceeding table is combined with post-emergence use of L-glufosinate ammonium, glyphosate potassium and dicamba ethanolamine salt.

The treatment combinations 144.1 to 144.799 in which one of the treatment combinations listed in the preceeding table is combined with post-emergence use of L-glufosinate ammonium, glyphosate potassium and dicamba diglycolamine salt.

The treatment combinations 145.1 to 145.799 in which one of the treatment combinations listed in the preceeding table is combined with post-emergence use of L-glufosinate ammonium, glyphosate potassium and dicamba potassium.

The treatment combinations 146.1 to 146.799 in which one of the treatment combinations listed in the preceeding table is combined with post-emergence use of L-glufosinate ammonium, glyphosate potassium and dicamba BAPMA salt.

The treatment combinations 147.1 to 147.799 in which one of the treatment combinations listed in the preceeding table is combined with post-emergence use of L-glufosinate sodium, glyphosate potassium and dicamba.

The treatment combinations 148.1 to 148.799 in which one of the treatment combinations listed in the preceeding table is combined with post-emergence use of L-glufosinate sodium, glyphosate potassium and dicamba ethanolamine salt.

The treatment combinations 149.1 to 149.799 in which one of the treatment combinations listed in the preceeding table is combined with post-emergence use of L-glufosinate sodium, glyphosate potassium and dicamba diglycolamine salt.

The treatment combinations 150.1 to 150.799 in which one of the treatment combinations listed in the preceeding table is combined with post-emergence use of L-glufosinate sodium, glyphosate potassium and dicamba potassium.

The treatment combinations 151.1 to 151.799 in which one of the treatment combinations listed in the preceeding table is combined with post-emergence use of L-glufosinate sodium, glyphosate potassium and dicamba BAPMA salt.

The treatment combinations 152.1 to 152.799 in which one of the treatment combinations listed in the preceeding table is combined with post-emergence use of L-glufosinate, glyphosate isopropylammonium and dicamba.

The treatment combinations 153.1 to 153.799 in which one of the treatment combinations listed in the preceeding table is combined with post-emergence use of L-glufosinate, glyphosate isopropylammonium and dicamba ethanolamine salt.

The treatment combinations 154.1 to 154.799 in which one of the treatment combinations listed in the preceeding table is combined with post-emergence use of L-glufosinate, glyphosate isopropylammonium and dicamba diglycolamine salt.

The treatment combinations 155.1 to 155.799 in which one of the treatment combinations listed in the preceeding table is combined with post-emergence use of L-glufosinate, glyphosate isopropylammonium and dicamba potassium.

The treatment combinations 156.1 to 156.799 in which one of the treatment combinations listed in the preceeding table is combined with post-emergence use of L-glufosinate, glyphosate isopropylammonium and dicamba BAPMA salt.

The treatment combinations 157.1 to 157.799 in which one of the treatment combinations listed in the preceeding table is combined with post-emergence use of L-glufosinate ammonium, glyphosate isopropylammonium and dicamba.

The treatment combinations 158.1 to 158.799 in which one of the treatment combinations listed in the preceeding table is combined with post-emergence use of L-glufosinate ammonium, glyphosate isopropylammonium and dicamba ethanolamine salt.

The treatment combinations 159.1 to 159.799 in which one of the treatment combinations listed in the preceeding table is combined with post-emergence use of L-glufosinate ammonium, glyphosate isopropylammonium and dicamba diglycolamine salt.

The treatment combinations 160.1 to 160.799 in which one of the treatment combinations listed in the preceeding table is combined with post-emergence use of L-glufosinate ammonium, glyphosate isopropylammonium and dicamba potassium.

The treatment combinations 161.1 to 161.799 in which one of the treatment combinations listed in the preceeding table is combined with post-emergence use of L-glufosinate ammonium, glyphosate isopropylammonium and dicamba BAPMA salt.

The treatment combinations 162.1 to 162.799 in which one of the treatment combinations listed in the preceeding table is combined with post-emergence use of L-glufosinate sodium, glyphosate isopropylammonium and dicamba.

The treatment combinations 163.1 to 163.799 in which one of the treatment combinations listed in the preceeding table is combined with post-emergence use of L-glufosinate sodium, glyphosate isopropylammonium and dicamba ethanolamine salt.

The treatment combinations 164.1 to 164.799 in which one of the treatment combinations listed in the preceeding table is combined with post-emergence use of L-glufosinate sodium, glyphosate isopropylammonium and dicamba diglycolamine salt.

The treatment combinations 165.1 to 165.799 in which one of the treatment combinations listed in the preceeding table is combined with post-emergence use of L-glufosinate sodium, glyphosate isopropylammonium and dicamba potassium.

The treatment combinations 166.1 to 166.799 in which one of the treatment combinations listed in the preceeding table is combined with post-emergence use of L-glufosinate sodium, glyphosate isopropylammonium and dicamba BAPMA salt.

The treatment combinations 167.1 to 167.799 in which one of the treatment combinations listed in the preceeding table is combined with post-emergence use of glyphosate.

The treatment combinations 168.1 to 168.799 in which one of the treatment combinations listed in the preceeding table is combined with post-emergence use of glyphosate and dicamba.

The treatment combinations 169.1 to 169.799 in which one of the treatment combinations listed in the preceeding table is combined with post-emergence use of glyphosate and dicamba ethanolamine salt.

The treatment combinations 170.1 to 170.799 in which one of the treatment combinations listed in the preceeding table is combined with post-emergence use of glyphosate and dicamba diglycolamine salt.

The treatment combinations 171.1 to 171.799 in which one of the treatment combinations listed in the preceeding table is combined with post-emergence use of glyphosate and dicamba potassium.

The treatment combinations 172.1 to 172.799 in which one of the treatment combinations listed in the preceeding table is combined with post-emergence use of glyphosate and dicamba BAPMA salt.

The treatment combinations 173.1 to 173.799 in which one of the treatment combinations listed in the preceeding table is combined with post-emergence use of glyphosate potassium.

The treatment combinations 174.1 to 174.799 in which one of the treatment combinations listed in the preceeding table is combined with post-emergence use of glyphosate potassium and dicamba.

The treatment combinations 175.1 to 175.799 in which one of the treatment combinations listed in the preceeding table is combined with post-emergence use of glyphosate potassium and dicamba ethanolamine salt.

The treatment combinations 176.1 to 176.799 in which one of the treatment combinations listed in the preceeding table is combined with post-emergence use of glyphosate potassium and dicamba diglycolamine salt.

The treatment combinations 177.1 to 177.799 in which one of the treatment combinations listed in the preceeding table is combined with post-emergence use of glyphosate potassium and dicamba potassium.

The treatment combinations 178.1 to 178.799 in which one of the treatment combinations listed in the preceeding table is combined with post-emergence use of glyphosate potassium and dicamba BAPMA salt.

The treatment combinations 179.1 to 179.799 in which one of the treatment combinations listed in the preceeding table is combined with post-emergence use of glyphosate isopropylammonium.

The treatment combinations 180.1 to 180.799 in which one of the treatment combinations listed in the preceeding table is combined with post-emergence use of glyphosate isopropylammonium and dicamba.

The treatment combinations 181.1 to 181.799 in which one of the treatment combinations listed in the preceeding table is combined with post-emergence use of glyphosate isopropylammonium and dicamba ethanolamine salt.

The treatment combinations 182.1 to 182.799 in which one of the treatment combinations listed in the preceeding table is combined with post-emergence use of glyphosate isopropylammonium and dicamba diglycolamine salt.

The treatment combinations 183.1 to 183.799 in which one of the treatment combinations listed in the preceeding table is combined with post-emergence use of glyphosate isopropylammonium and dicamba potassium.

The treatment combinations 184.1 to 184.799 in which one of the treatment combinations listed in the preceeding table is combined with post-emergence use of glyphosate isopropylammonium and dicamba BAPMA salt.

The treatment combinations 185.1 to 185.799 in which one of the treatment combinations listed in the preceeding table is combined with post-emergence use of L-glufosinate and fenquinotrione.

The treatment combinations 186.1 to 186.799 in which one of the treatment combinations listed in the preceeding table is combined with post-emergence use of L-glufosinate ammonium and fenquinotrione.

The treatment combinations 187.1 to 187.799 in which one of the treatment combinations listed in the preceeding table is combined with post-emergence use of L-glufosinate sodium and fenquinotrione.

The treatment combinations 188.1 to 188.799 in which one of the treatment combinations listed in the preceeding table is combined with post-emergence use of L-glufosinate and tolpyralate.

The treatment combinations 189.1 to 189.799 in which one of the treatment combinations listed in the preceeding table is combined with post-emergence use of L-glufosinate ammonium and tolpyralate.

The treatment combinations 190.1 to 190.799 in which one of the treatment combinations listed in the preceeding table is combined with post-emergence use of L-glufosinate sodium and tolpyralate.

The treatment combinations 191.1 to 191.799 in which one of the treatment combinations listed in the preceeding table is combined with post-emergence use of fenquinotrione.

The treatment combinations 192.1 to 192.799 in which one of the treatment combinations listed in the preceeding table is combined with post-emergence use of tolpyralate.

The abovementioned properties and advantages are necessary under practical weed control conditions to keep the cotton free from undesired competing plants and thus to guarantee and/or increase the yields from the qualitative and quantitative point of view. These novel combinations markedly exceed the technical state of the art with a view to the properties described.

While the active compounds of the inventive mixtures have an outstanding herbicidal activity against monocotyledonous and dicotyledonous weeds, the tolerant, or cross-tolerant, glufosinate tolerant cotton are damaged only to a minor extent, or not at all.

As mentioned above, the inventive mixtures are suitable for controlling a large number of harmful plants in glufosinate tolerant cotton.

Thus, the term "glufosinate tolerant cotton" as used herein includes also (cotton) plants which have been modified by mutagenesis, genetic engineering or breeding and mutation selection techniques in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name.

Glufosinate tolerance has been created by using mutagenesis as well as using genetic engineering. Transgenic cotton events comprising glufosinate tolerance genes are for example, but not excluding others, 3006-210-23×281-24-236×MON1445 (event code: DAS-21Ø23-5×DAS-24236-5×MON-Ø1445-2, gene: bar, e.g. commercially available as WideStrike™ Roundup Ready™ Cotton), 3006-210-23×281-24-236×MON88913 (event code: DAS-21Ø23-5×DAS-24236-5×MON-88913-8, gene: bar, e.g. commercially available as Widestrike™ Roundup Ready Flex™ Cotton), 3006-210-23×281-24-236×MON88913×COT102 (event code: DAS-21Ø23-5×DAS-24236-5×MON-88913-8×SYN-IR1Ø2-7, gene: pat, e.g. commercially available as Widestrike™×Roundup Ready Flex™×VIPCOT™ Cotton), GHB614×LLCotton25 (event code: BCS-GHØØ2-5×ACS-GHØØ1-3, gene: bar, e.g. commercially available as GlyTol™ Liberty Link™), GHB614×T304-40×GHB119 (event code: BCS-GHØØ2-5×BCS-GHØØ4-7×BCS-GHØØ5-8, gene: bar, e.g. commercially available as Glytol™×Twinlink™), LLCotton25 (event code: ACS-GHØØ1-3, gene: bar, e.g. commercially available as ACS-GHØØ1-3), GHB614×T304-40×GHB119×COT102 (event code: BCS-GHØØ2-5×BCS-GHØØ4-7×BCS-GHØØ5-8×SYN-IR1Ø2-7, gene: bar, e.g. commercially available as Glytol™×Twinlink™×VIPCOT™ Cotton), LLCotton25×MON15985 (event code: ACS-GHØØ1-3×MON-15985-7, gene: bar, e.g. commercially available as Fibermax™ Liberty Link™ Bollgard II™), T304-40×GHB119 (event code: BCS-GHØØ4-7×BCS-GHØØ5-8, gene: bar, e.g. commercially available as TwinLink™ Cotton), GHB614×T304-40×GHB119×COT102 (event code: BCS-GHØØ2-5×BCS-GHØØ4-7×BCS-GHØØ5-8×SYN-IR1Ø2-7, gene: bar, e.g. commercially available as Glytol™×Twinlink™×VIPCOT™ Cotton), GHB119 (event code: BCS-GHØØ5-8, gene: bar), GHB614×LLCotton25×MON15985 (event code: CS-GHØØ2-5×ACS-GHØØ1-3×MON-15985-7, gene: bar), MON 88701-3 (event code: MON88701, gene: bar), T303-3 (event code: BCS-GHØØ3-6, gene: bar), T304-40 (event code: BCS-GHØØ3-6, gene: bar), (event code: BCS-GHØØ4-7, gene: bar), 81910 (event code: DAS-81910-7, gene: pat), MON8870 (event code: MON 887Ø1-3, gene: bar), MON88701×MON88913 (event code: MON 887Ø1-3×MON-88913-8, gene: bar), MON88701×MON88913×MON15985 (event code: MON 887Ø1-3×MON-88913-8×MON-15985-7, gene: bar), 281-24-236×3006-210-23×COT102×81910 (event code: DAS-24236-5×DAS-21Ø23-5×SYN-IR1Ø2-7×DAS-81910-7, gene: pat), COT102×MON15985×MON88913×MON88701 (event code: SYN-IR1Ø2-7×MON-15985-7×MON-88913-8×MON 887Ø1-3, gene: bar) and 3006-210-23×281-24-236×MON88913×COT102×81910 (event code: DAS-21Ø23-5×DAS-24236-5×MON-88913-8×SYN-IR1Ø2-7×DAS-81910-7, gene: pat).

In other aspects, cotton plants of the invention include those plants which have been subjected to genetic modifications other than glufosinate tolerance by breeding, mutagenesis or genetic engineering, e.g. have been rendered tolerant to applications of specific other classes of herbicides, such as PPO inhibitors (e. g. saflufenacil, trifludimoxazin), AHAS inhibitors; auxinic herbicides such as dicamba or 2,4-D; bleaching herbicides such as hydroxyphenylpyruvate dioxygenase (HPPD) inhibitors (e. g. isoxaflutole, mesotrione, tembotrione, topramezone, bicyclopyrone) or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); or oxynil {i.e. bromoxynil or ioxynil) herbicides as a result of conventional methods of breeding or genetic engineering, Thus, cotton plants of the invention can be made resistant to multiple classes of herbicides through multiple genetic modifications, such as for example resistance to both glyphosate and dicamba; glyphosate, 2,4-D and glufosinate (e. g. Enlist® cotton); glyphosate and glufosinate (GlyTol® LibertyLink® cotton); glyphosate and HPPD inhibitors such as isoxaflutole; glyphosate, glufosinate and HPPD inhibitors such as isoxaflutole; glufosinate and HPPD inhibitors such as isoxaflutole; glyphosate, glufosinate, dicamba and HPPD inhibitors such as isoxaflutole; glyphosate, dicamba and glufosinate (XtendFlex® cotton); glyphosate and PPO inhibitors; glufosinate and PPO inhibitors; glyphosate, glufosinate and PPO inhibitors; glyphosate, dicamba and PPO inhibitors; glyphosate, 2,4-D, glufosinate and PPO inhibitors; glyphosate, dicamba, glufosinate and PPO inhibitors; glyphosate, 2,4-D, glufosinate and PPO inhibitors; glyphosate, PPO inhibitors and HPPD inhibitors; glufosinate, HPPD inhibitors and PPO inhibitors; glyphosate, glufosinate, HPPD inhibitors and PPO inhibitors; glyphosate, dicamba, HPPD inhibitors and PPO inhibitors; glyphosate, 2,4-D, glufosinate, HPPD inhibitors and PPO inhibitors; glyphosate, dicamba, glufosinate, HPPD inhibitors and PPO inhibitors; or to one of the aforementioned cotton plants that are tolerant to further classes of herbicides such as AHAS inhibitors or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein.

In addition to these classes of inhibitors, cotton plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such additional tolerance traits may be expressed, e.g.: as mutant or wildtype PPO proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity.

Glufosinate tolerant cotton plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

In all treatments according to the methods of the present invention, the inventive mixtures can be applied in conventional manner by using techniques as skilled person is familiar with. Suitable techniques include spraying, atomizing, dusting, spreading or watering. The type of application depends on the intended purpose in a well known manner; in any case, they should ensure the finest possible distribution of the active ingredients according to the invention.

In one embodiment, the inventive mixtures are applied to locus mainly by spraying, in particular foliar spraying of an aqueous dilution of the active ingredients of the mixture. Application can be carried out by customary spraying techniques using, for example, water as carrier and spray liquor rates of from about 10 to 2000 l/ha or 50 to 1000 l/ha (for example from 100 to 500 l/ha). Application of the inventive mixtures by the low-volume and the ultra-low-volume method is possible, as is their application in the form of microgranules.

The required application rate of the mixture of the pure active compounds depends on the density of the undesired vegetation, on the development stage of the plants, on the climatic conditions of the location where the mixture is used and on the application method.

In general, the rate of application of L-glufosinate is usually from 50 g/ha to 3000 g/ha and preferably in the range from 100 g/ha to 2000 g/ha or from 200 g/ha to 1500 g/ha of active substance (a.i.), and the rate of application of the second herbicida compound II is from 1 g/ha to 2000 g/ha and preferably in the range from 5 g/ha to 1500 g/ha, more preferably from 25 g/ha to 900 g/ha of active substance (a.i.).

The examples which follow illustrate the invention without imposing any limitation.

BIOLOGICAL EXAMPLES

Synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, Weeds, 15, 21-22):

$$E = X + Y - \frac{XY}{100}$$

When the observed combined control effect is greater than the expected (calculated) combined control effect (E), then the combined effect is synergistic.

The following tests demonstrate the control efficacy of compounds, mixtures or compositions of this invention on specific weeds. However, the weed control afforded by the compounds, mixtures or compositions is not limited to these species. The analysis of synergism or antagonism between the mixtures or compositions was determined using Colby's equation.

Test Method:

The culture containers used were plastic flowerpots containing loamy sand with approximately 3.0% of humus as the substrate. The seeds of the test plants were sown separately for each species and/or resistant biotype. For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients. For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. Depending on the species, the plants were kept at 10-25° C. or 20-35° C., respectively. The test period extended to 20 days after treatment. During this time, the plants were tended, and their response to the individual treatments was evaluated. The evaluation was carried out by using a scale from 0 to 100. 100 means no emergence of the plants or complete destruction of at least the above-ground parts, and 0 means no damage, or normal course of growth. Data shown are the mean of two replications.

Products:

L-Glufosinate: 5% EC formulation

Diuron: 5% EC formulation

Fluometuron: 5% EC formulation

Thidiazuron: 500 g/l SC formulation

Saflufenacil: 342 g/l SC formulation

Compound II-83: 5% EC formulation (Compound II-83: ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate)

Trifludimoxazin: 500 g/l SC formulation

Sulfentrazone: 480 g/l SC formulation 2,4-D dimethylammonium salt: 500 g/l SL formulation (concentration calculated for 2,4-D acid)

Dicamba dimethylammonium salt: 480 g/l SL formulation (concentration calculated for dicamba acid)

Dimethenamid-P: 720 g/l EC formulation

S-Metolachlor: 960 g/l EC formulation

Tembotrione: 44 g/l OD formulation

Bicyclopyrone: 5% EC formulation

Topramezone: 336 g/l SC formulation

Weeds in the Study:

| EPPO Code | Scientific Name |
|---|---|
| AVEFA | Avena fatua |
| ABUTH | Abutilon theophrasti |
| SETVI | Setaria viridis |
| ECHCG | Echinochloa crus-galli |
| CYPIR | Cyperus iria |
| ERICA | Erigeron Canadensis, Conyza canadensis |
| KCHSC | Kochia scoparia |
| CHEAL | Chenopodium album |

Example 1: Post Emergence Treatment with the Mixture of L-Glufosinate with Diuron

| Application rate in g ai/ha | | Herbicidal activity against AVEFA | |
| --- | --- | --- | --- |
| L-Glufosinate | Diuron | Found | Calculated |
| 300 | — | 20 | — |
| — | 250 | 30 | — |
| 300 | 250 | 70 | 44 |
| 300 | — | 20 | — |
| — | 125 | 20 | — |
| 300 | 125 | 50 | 36 |

Example 2: Post Emergence Treatment with the Mixture of L-Glufosinate with Fluometuron

| Application rate in g ai/ha | | Herbicidal activity against ABUTH | |
| --- | --- | --- | --- |
| L-Glufosinate | Fluometuron | Found | Calculated |
| 75 | — | 0 | — |
| — | 250 | 20 | — |
| 75 | 250 | 35 | 20 |
| 75 | — | 0 | — |
| — | 125 | 0 | — |
| 75 | 125 | 35 | 0 |

Example 3: Post Emergence Treatment with the Mixture of L-Glufosinate with Thidiazuron

| Application rate in g ai/ha | | Herbicidal activity against SETVI | |
| --- | --- | --- | --- |
| L-Glufosinate | Thidiazuron | Found | Calculated |
| 150 | — | 70 | — |
| — | 50 | 0 | — |
| 150 | 50 | 80 | 70 |
| 75 | — | 0 | — |
| — | 50 | 0 | — |
| 75 | 50 | 10 | 0 |

Example 4: Post Emergence Treatment with the Mixture of L-Glufosinate with Saflufenacil

| Application rate in g ai/ha | | Herbicidal activity against ECHCG | |
| --- | --- | --- | --- |
| L-Glufosinate | Saflufenacil | Found | Calculated |
| 400 | — | 65 | — |
| — | 0.5 | 0 | — |
| 400 | 0.5 | 97 | 65 |
| 200 | — | 0 | — |
| — | 0.5 | 0 | — |
| 200 | 0.5 | 35 | 0 |

Example 5: Post Emergence Treatment with the Mixture of L-Glufosinate with Compound II-83 (ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate)

| Application rate in g ai/ha | | Herbicidal activity against CYPIR | |
| --- | --- | --- | --- |
| L-Glufosinate | Compound II-83 | Found | Calculated |
| 200 | — | 0 | — |
| — | 0.25 | 0 | — |
| 200 | 0.25 | 35 | 0 |

Example 6: Post Emergence Treatment with the Mixture of L-Glufosinate with Trifludimoxazin

| Application rate in g ai/ha | | Herbicidal activity against ECHCG | |
| --- | --- | --- | --- |
| L-Glufosinate | Trifludimoxazin | Found | Calculated |
| 400 | — | 65 | — |
| — | 0.25 | 10 | — |
| 400 | 0.25 | 75 | 69 |
| 200 | — | 0 | — |
| — | 0.25 | 10 | — |
| 200 | 0.25 | 33 | 10 |

Example 7: Post Emergence Treatment with the Mixture of L-Glufosinate with Sulfentrazone

| Application rate in g ai/ha | | Herbicidal activity against ERICA | |
| --- | --- | --- | --- |
| L-Glufosinate | Sulfentrazone | Found | Calculated |
| 75 | — | 90 | — |
| — | 2.5 | 0 | — |
| 75 | 2.5 | 100 | 90 |
| 75 | — | 90 | — |
| — | 1.25 | 0 | — |
| 75 | 1.25 | 100 | 90 |

Example 8: Post Emergence Treatment with the Mixture of L-Glufosinate with 2,4-D Dimethylammonium Salt

| Application rate in g ai/ha | | Herbicidal activity against | | | |
| --- | --- | --- | --- | --- | --- |
| | 2,4-D as dimethyl- | | | | |
| | ammonium | AVEFA | | SETVI | |
| L-Glufosinate | salt | Found | Calculated | Found | Calculated |
| 100 | — | 35 | — | 30 | — |
| — | 140 | 0 | — | 0 | — |
| 100 | 140 | 65 | 35 | 65 | 30 |
| 100 | — | 35 | — | 30 | — |

-continued

| Application rate in g ai/ha | | Herbicidal activity against | | | |
|---|---|---|---|---|---|
| | 2,4-D as dimethyl-ammonium | AVEFA | | SETVI | |
| L-Glufosinate | salt | Found | Calculated | Found | Calculated |
| — | 70 | 0 | — | 0 | — |
| 100 | 70 | 40 | 35 | 65 | 30 |

Example 9: Post Emergence Treatment with the Mixture of L-Glufosinate with Dicamba Dimethylammonium Salt

| Application rate in g ai/ha | | Herbicidal activity against SETVI | |
|---|---|---|---|
| L-Glufosinate | Dicamba as dimethyl-ammonium salt | Found | Calculated |
| 100 | — | 30 | — |
| — | 140 | 30 | — |
| 100 | 140 | 80 | 51 |
| 100 | — | 30 | — |
| — | 70 | 0 | — |
| 100 | 70 | 65 | 30 |
| 100 | — | 30 | — |
| — | 35 | 0 | — |
| 100 | 35 | 60 | 30 |

Example 10: Post Emergence Treatment with the Mixture of L-Glufosinate with Dimethenamid-P

| Application rate in g ai/ha | | Herbicidal activity against KCHSC | |
|---|---|---|---|
| L-Glufosinate | Dimethenamid-P | Found | Calculated |
| 200 | — | 90 | — |
| — | 1000 | 70 | — |
| 200 | 1000 | 100 | 97 |
| 200 | — | 90 | — |
| — | 500 | 0 | — |
| 200 | 500 | 100 | 90 |

Example 11: Post Emergence Treatment with the Mixture of L-Glufosinate with S-Metolachlor

| Application rate in g ai/ha | | Herbicidal activity against CHEAL | |
|---|---|---|---|
| L-Glufosinate | S-Metolachlor | Found | Calculated |
| 100 | — | 0 | — |
| — | 1000 | 75 | — |
| 100 | 1000 | 85 | 75 |
| 100 | — | 0 | — |
| — | 500 | 20 | — |
| 100 | 500 | 85 | 20 |

Example 12: Post Emergence Treatment with the Mixture of L-Glufosinate with Tembotrione

| Application rate in g ai/ha | | Herbicidal activity against ECHCG | |
|---|---|---|---|
| L-Glufosinate | Tembotrione | Found | Calculated |
| 200 | — | 0 | — |
| — | 0.5 | 0 | — |
| 200 | 0.5 | 50 | 0 |
| 100 | — | 0 | — |
| — | 0.5 | 0 | — |
| 100 | 0.5 | 40 | 0 |

Example 13: Post Emergence Treatment with the Mixture of L-Glufosinate with Bicyclopyrone

| Application rate in g ai/ha | | Herbicidal activity against ECHCG | |
|---|---|---|---|
| L-Glufosinate | Bicyclopyrone | Found | Calculated |
| 200 | — | 0 | — |
| — | 2 | 0 | — |
| 200 | 2 | 60 | 0 |
| 100 | — | 0 | — |
| — | 2 | 0 | — |
| 100 | 2 | 55 | 0 |

Example 14: Post Emergence Treatment with the Mixture of L-Glufosinate with Topramezone

| Application rate in g ai/ha | | Herbicidal activity against ECHCG | |
|---|---|---|---|
| L-Glufosinate | Topramezone | Found | Calculated |
| 200 | — | 0 | — |
| — | 1 | 0 | — |
| 200 | 1 | 90 | 0 |
| 100 | — | 0 | — |
| — | 1 | 0 | — |
| 100 | 1 | 35 | 0 |

The invention claimed is:

1. A method for controlling undesirable vegetation in cotton, the method comprising:
    applying to the undesirable vegetation or a locus thereof or applying to soil or water a mixture comprising
    a) L-glufosinate and its salts as compound I, and
    b) isoxaflutole as compound II;
    wherein:
        L-glufosinate comprises more than 70% by weight of the L-enantiomer; and
        the weight ratio of compound I to compound II is from 1000:1 to 1:500.

2. The method of claim 1, wherein compound I in the herbicidal mixture is selected from the group consisting of L-glufosinate-ammonium, L-glufosinate-sodium as L-glufosinate salts, and L-glufosinate as free acid.

3. The method of claim 1, wherein compound I in the herbicidal mixture is L-glufosinate-ammonium.

4. The method of claim 1, wherein L-glufosinate in the herbicidal mixture comprises more than 80% by weight of the L-enantiomer.

5. The method of claim 1, wherein L-glufosinate comprises more than 90% by weight of the L-enantiomer.

6. The method of claim 1, wherein L-glufosinate comprises 95% by weight of the L-enantiomer.

7. The method of claim 1, wherein the weight ratio of compound I to compound II is from 500:1 to 1:250.

8. The method of claim 1, wherein the weight ratio of compound I to compound II is from 50:1 to 1:5.

9. A pesticidal mixture, comprising
a) L-glufosinate and its salts as compound I, and
b) isoxaflutole as compound II;
wherein:
L-glufosinate comprises more than 95% by weight of the L-enantiomer; and
the weight ratio of compound I to compound II is from 1000:1 to 1:10.

10. A pesticidal composition, comprising a liquid or solid carrier and the mixture of claim 9.

11. The method of claim 1, wherein;
cotton has been or will be planted at the locus; and
the cotton is a glufosinate tolerant cotton.

12. The method of claim 11, wherein the glufosinate tolerant cotton is a transgenic cotton plant.

13. The method of claim 1, wherein compounds I and II of the mixture are applied simultaneously, that is jointly or separately, or in succession.

14. The method of claim 1, comprising applying the mixture prior to planting cotton at the locus.

15. The method of claim 1, comprising applying the mixture to the undesirable vegetation or the locus thereof.

16. The method of claim 1, comprising: applying the compound I to the locus at an application rate in a range from 50 g/ha to 3000 g/ha.

17. The method of claim 1, wherein the weight ratio of compound I to compound II is from 1000:1 to 1:10.

18. The method of claim 1, wherein the weight ratio of compound I to compound II is from 1000:1 to 50:1.

19. The method of claim 3, wherein the weight ratio of compound I to compound II is from 1000:1 to 1:10.

20. The method of claim 4, wherein the weight ratio of compound I to compound II is from 1000:1 to 50:1.

* * * * *